US007316931B2

(12) United States Patent
Schneider et al.

(10) Patent No.: US 7,316,931 B2
(45) Date of Patent: Jan. 8, 2008

(54) MASS DEFECT LABELING FOR THE DETERMINATION OF OLIGOMER SEQUENCES

(75) Inventors: Luke V. Schneider, Half Moon Bay, CA (US); Michael P. Hall, San Carlos, CA (US); Robert Petesch, Newark, CA (US)

(73) Assignee: Target Discovery, Inc., Palo Alto, CA (US)

( * ) Notice: Subject to any disclaimer, the term of this patent is extended or adjusted under 35 U.S.C. 154(b) by 212 days.

(21) Appl. No.: 10/913,020

(22) Filed: Aug. 6, 2004

(65) Prior Publication Data

US 2006/0073485 A1  Apr. 6, 2006

Related U.S. Application Data

(63) Continuation of application No. 10/035,349, filed on Oct. 19, 2001, now Pat. No. 6,962,818.

(60) Provisional application No. 60/242,165, filed on Oct. 19, 2000, provisional application No. 60/242,398, filed on Oct. 19, 2000.

(51) Int. Cl.
G01N 24/00 (2006.01)
(52) U.S. Cl. .................................. 436/173; 436/15
(58) Field of Classification Search .................... None
See application file for complete search history.

(56) References Cited

U.S. PATENT DOCUMENTS

| 4,830,010 A | 5/1989 | Marshall |
| 4,842,701 A | 6/1989 | Smith et al. |
| 4,994,165 A | 2/1991 | Lee et al. |
| 5,100,778 A | 3/1992 | Rademacher et al. |
| 5,174,962 A | 12/1992 | Brennan |
| 5,306,412 A | 4/1994 | Whitehouse et al. |
| 5,386,832 A | 2/1995 | Wagner et al. |
| 5,470,753 A | 11/1995 | Sepetov et al. |
| 5,505,832 A | 4/1996 | Laukien et al. |
| 5,538,897 A | 7/1996 | Yates, III et al. |
| 5,667,984 A | 9/1997 | Parekh et al. |
| 5,691,141 A | 11/1997 | Koster |
| 5,700,642 A | 12/1997 | Monforte et al. |
| 5,827,659 A | 10/1998 | Patterson |
| 5,856,082 A | 1/1999 | Aebersold et al. |
| 5,872,010 A | 2/1999 | Karger et al. |

(Continued)

FOREIGN PATENT DOCUMENTS

JP         2004-52809        7/2004

(Continued)

OTHER PUBLICATIONS

Intregrated Publishing. Nuclear Power Fundamentals. http://www.tpub.com/content/doe/h1019v1/css/h1019v1_45.htm.*

(Continued)

Primary Examiner—Yelena G. Gakh
(74) Attorney, Agent, or Firm—Paul, Hastings, Janofsky & Walker, LLP

(57) ABSTRACT

Mass tagging methods are provided that lead to mass spectrometer detection sensitivities and molecular discriminations that are improved over other methods. In particular the methods are useful for discriminating tagged molecules and fragments of molecules from chemical noise in the mass spectrum. These mass tagging methods are useful for oligomer sequencing, determining the relative abundances of molecules from different samples, and identifying individual molecules or chemical processing steps in combinatorial chemical libraries. The methods provided are useful for the simultaneous analysis of multiple molecules and reaction mixtures by mass spectrometric methods.

19 Claims, 32 Drawing Sheets

U.S. PATENT DOCUMENTS

| | | | |
|---|---|---|---|
| 5,919,709 | A | 7/1999 | Parmelee et al. |
| 6,004,770 | A | 12/1999 | Nelson |
| 6,017,693 | A | 1/2000 | Yates, III et al. |
| 6,027,890 | A | 2/2000 | Ness et al. |
| 6,056,926 | A | 5/2000 | Sugarman et al. |
| 6,090,558 | A | 7/2000 | Butler et al. |
| 6,194,144 | B1 | 2/2001 | Koster |
| 6,277,644 | B1 | 8/2001 | Farnsworth et al. |
| 6,329,146 | B1 | 12/2001 | Crooke et al. |
| 6,335,525 | B1 | 1/2002 | Takada et al. |
| 6,359,111 | B1 | 3/2002 | Meyer et al. |
| 6,379,971 | B1 | 4/2002 | Schneider et al. |
| 6,391,649 | B1 | 5/2002 | Chait et al. |
| 2005/0147985 | A1 | 7/2005 | Pappin et al. |

FOREIGN PATENT DOCUMENTS

| | | |
|---|---|---|
| JP | 2004-203897 | 7/2004 |
| JP | 2004-519665 | 7/2004 |
| JP | 2004-520120 | 7/2004 |
| JP | 2004-520903 | 7/2004 |
| JP | 2004-521062 | 7/2004 |
| JP | 2004-521616 | 7/2004 |
| JP | 2004-522980 | 7/2004 |

OTHER PUBLICATIONS

Hughey et al. "Kendrick Mass Defect Spectrum: A Compact Visual Analysis for Ultrahigh-Resolution Broadband Mass Spectra", Anal Chem., 2001, v. 73, pp. 4676-4681.*

Graham D, et. al, "The Insulin-like Growth Factor (IGF) Blinding Site of Bovine Insulin-like Growth Factor Binding Protein-2 (bIGFBP-2) Probed by Iodination", The Journal of Biological Chemistry, Nov. 29, 1996, vol. 271, No. 48, pp. 30529-30536.

Kristina A, et. al, "Sequencing of Sulfated Oligosaccharides from Mucins by Liquid Chromatography and Electrospray Ionization Tandem Mass Spactrometry", Analytical Chemistry, Oct. 1, 2000, vol. 72, No. 19, pp. 4543-4549.

Scott A Gerber et al., "Absolute quantification of proteins and phosphoproteins from cell Iysates by tandem MS", Proceedings of the National Academy of Sciences of the United States of America, Jun. 10, 2003, vol. No. 12, pp. 6940-6945.

Steven P. Gygi et al., "Quantitative analysis of complex protein mixtures using isotope-coded affinity tags", Nature America Inc., Jul. 13, 1999, vol. 17, pp. 994-999.

Shao-En Ong et al., "Stable Isotope labeling by Amino Acids in Cell Culture, SILAC, as Simple and Accurate Approach to Expression Proteomics*", Molecular & Cellular Proteomics Jan. 5, 2002, pp. 376-386.

Olga A. Mirgorodskaya et al., "Quantitation of peptides and proteins by matrix assisted laser desorption/ionization mass spectrometry using O-labeled internal standards", Rapid Communications in Mass Spectrometry, 2000, pp. 1226-1232.

Fred E. Regnier et al., "Global internal standard technology for comparative proteomics", Journal of Chromatography A, 2002, pp. 173-184.

* cited by examiner

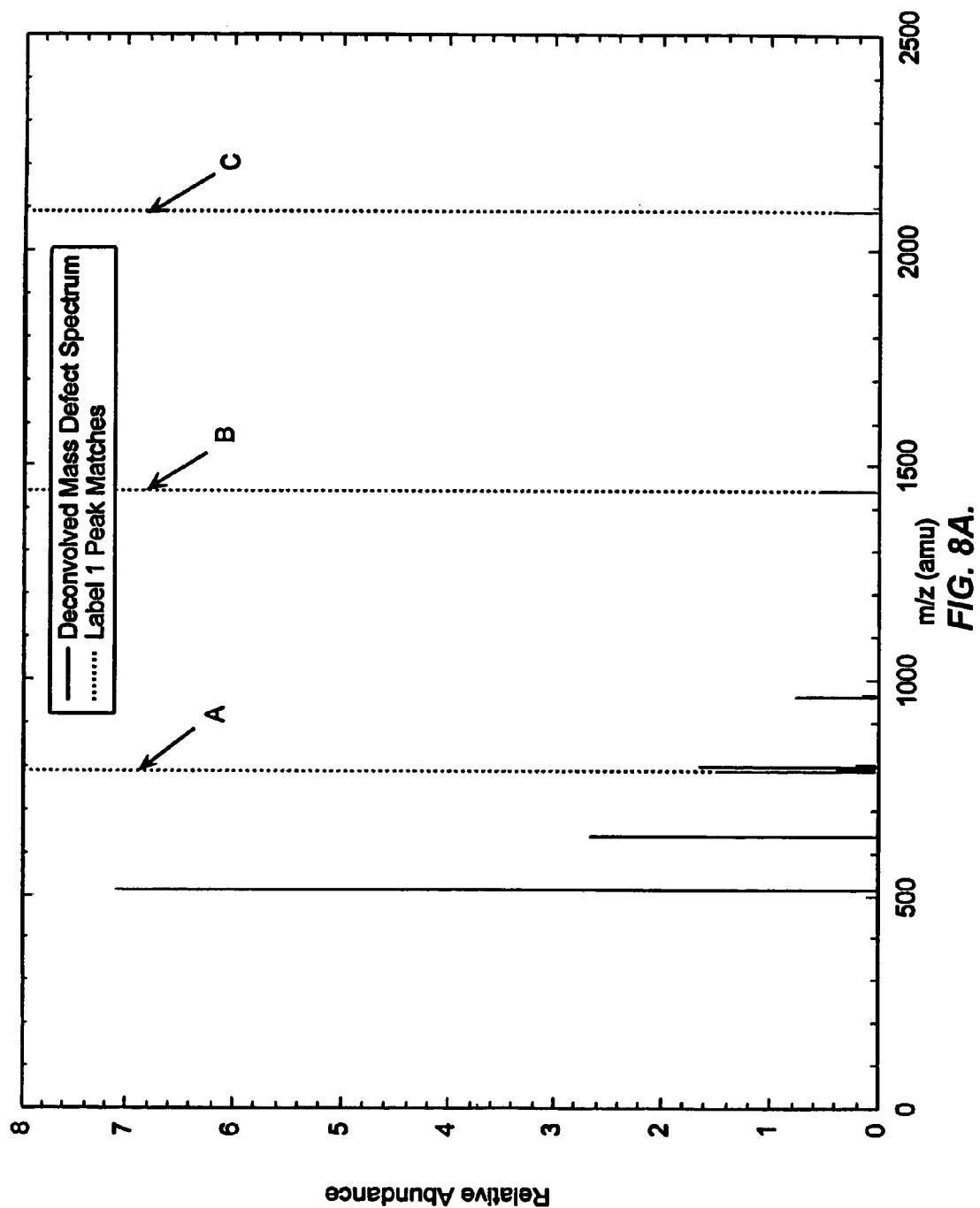

The general structure of the photocleavable mass defect tag where Br is the mass defect element that is linked through the amino acid (R) to the remainder of the tag.

ddATP* ddGTP* ddTTP* ddCTP*

SEQUENCE LISTING

```
<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:true
      N-terminal horse apomyoglobin (Myo) sequence
<220> FEATURE:
<221> NAME/KEY: MOD_RES
<222> LOCATION: (1)
<223> OTHER INFORMATION: Xaa = Gly labeled with 5-bromo-3-pyridylacetic
      acid (5-Br-3-PAA)

<400> SEQUENCE: 1

Xaa Leu Ser Asp Gly Glu
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:competing 5
      residue false sequence, top ranked sequence at
      five residues
<220> FEATURE:
<221> NAME/KEY: MOD_RES
<222> LOCATION: (1)
<223> OTHER INFORMATION: Xaa = Gly labeled with 5-bromo-3-pyridylacetic
      acid (5-Br-3-PAA)

<400> SEQUENCE: 2

Xaa Leu Ser Asp Trp
 1               5
```

```
<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:sequence
      carrying cloned unknown DNA sequence

<400> SEQUENCE: 3
tcagtgctgc tgcaacatgt tacaggaaat                                       30

<210> SEQ ID NO 4
<211> LENGTH: 18
<212> TYPE: DNA
<213> ORGANISM: Artificial Sequence
<220> FEATURE:
<221> NAME/KEY: modified_base
<222> LOCATION: (1)
<223> OTHER INFORMATION: n = ribosyl adenosine
<220> FEATURE:
<223> OTHER INFORMATION: Description of Combined DNA/RNA Molecule:M13
      origin of replication primer labeled at the 5' end
      with ribosyl adenosine
<220> FEATURE:
<223> OTHER INFORMATION: Description of Artificial Sequence:M13 origin
      of replication primer labeled at the 5' end with
      ribosyl adenosine

<400> SEQUENCE: 4
ntgttgcagc agcactga                                                    18

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence:DNA fragment
      from mass ladder produced by chain termination

<400> SEQUENCE: 5
caatgtcctt ta                                                          12

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:DNA fragment
      from mass ladder produced by chain termination

<400> SEQUENCE: 6
caatgtcctt t                                                           11

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:DNA fragment
      from mass ladder produced by chain termination

<400> SEQUENCE: 7
caatgtcctt                                                             10

<210> SEQ ID NO 8
<211> LENGTH: 5
<212> TYPE: PRT
<213> ORGANISM: Artificial Sequence
<220> FEATURE:
```

-continued

```
<223> OTHER INFORMATION: Description of Artificial Sequence:competing 5
      residue false sequence, top ranked sequence at
      five residues

<400> SEQUENCE: 8

Gly Leu Ser Asp Trp
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:true
      N-terminal horse apomyoglobin (Myo) sequence

<400> SEQUENCE: 9

Gly Leu Ser Asp Gly Glu
 1               5

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence:cloned
      unknown DNA sequence

<400> SEQUENCE: 10
gttacaggaa at                                                        12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence:sequence
      determined from mass spectral data analysis

<400> SEQUENCE: 11
atttcctgta ac                                                        12

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:true
      ubiquitin N-terminal sequence

<400> SEQUENCE: 12

Met Gln Ile Phe Val Lys
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:first ranked
      competing possibility at fifth residue

<400> SEQUENCE: 13

Met Gln Ile Phe Arg
 1               5
```

MASS DEFECT LABELING FOR THE DETERMINATION OF OLIGOMER SEQUENCES

CROSS-REFERENCES TO RELATED APPLICATIONS

This application is a continuation of U.S. patent application Ser. No. 10/035,349, filed Oct. 19, 2001 now U.S. Pat. No. 6,962,818, which claims the benefit of provisional U.S. Patent Application Ser. No. 60/242,165, filed Oct. 19, 2000 and of provisional U.S. Patent Application Ser. No. 60/242,398, filed on Oct. 19, 2000. These applications are incorporated by reference in their entirety for all purposes.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Many molecules are fragmented by chemical, electrical (electron beam or field induced collisions with neutral gas molecules), or optical (excimer lasers) means in mass spectrometers so that the masses of the resulting labeled ion fragments can be used to identify or reconstruct the original molecule. In other instances molecules may coelute from separation processes to be further distinguished by mass spectrometry. In some instances a label is attached to the parent molecule, or specific molecules in a mixture, to assist in the identification of the resulting labeled ions or ion fragments from other chemical noise in the mass spectrum. Typically, this label consists of elements, or isotopes of elements, already contained in the parent molecule. In this way two or more peaks of predetermined relative abundances can be found in the mass spectrum and used to confirm the identify of labeled fragments. However, when the label contains elements (or isotopes of these elements) already contained in the parent molecule or in other ions generated from or otherwise contaminating the sample matrix, one or more of the labeled fragment peaks may overlap with other unlabeled ion peaks in the spectrum, confounding identification of the labeled ions.

Historically, techniques such as Edman degradation have been extensively used for protein sequencing. See, Stark, in: *Methods in Enzymology*, 25:103–120 (1972); Niall, in: *Methods in Enzymology*, 27:942–1011 (1973); Gray, in: *Methods in Enzymology*, 25:121–137 (1972); Schroeder, in: *Methods in Enzymology*, 25:138–143 (1972); Creighton, *Proteins: Structures and Molecular Principles* (W.H. Freeman, NY, 1984); Niederwieser, in: *Methods in Enzymology*, 25:60–99 (1972); and Thiede, et al. *FEBS Lett.*, 357:65–69 (1995). However, sequencing by collision-induced dissociation mass spectrometry (MS) methods (MS/MS sequencing) has rapidly evolved and has proved to be faster and require less protein than Edman techniques. See, Shevchenko, A., et al., *Proc. Natl. Acad. Sci.* (*USA*), 93:14440–14445 (1996); Wilm, et al., *Nature*, 379:466–469 (1996); Mark, J., "Protein structure and identification with MS/MS," paper presented at the PE/Sciex Seminar Series, Protein Characterization and Proteomics: Automated high throughput technologies for drug discovery, Foster City, Calif. (March, 1998); and Bieman, *Methods in Enzymology*, 193:455–479 (1990).

MS sequencing is accomplished either by using higher voltages in the ionization zone of the MS to randomly fragment a single peptide isolated from a protein digest, or more typically by tandem MS using collision-induced dissociation in the ion trap. See, Bieman, ibid. Several techniques can be used to select the peptide fragment used for MS/MS sequencing, including accumulation of the parent peptide fragment ion in the quadrapole MS unit (see, Mark, J. ibid.; Mann, M., paper presented at the IBC Proteomics conference, Boston, Mass. (Nov. 10–11, 1997); and Bieman, *Methods in Enzymology*, 193:455–479 (1990)), capillary electrophoretic separation coupled to ES-TOF MS detection (see, Aebersold, R. "Proteome analysis: Biological assay or data archive?," paper presented at the IBC Proteomics conference, Coronado, Calif. (Jun. 11–12, 1998) and Smith, et al., in: *CRC Handbook of Capillary Electrophoresis: A Practical Approach*, Chp. 8, pgs 185–206 (CRC Press, Boca Raton, Fla., 1994)), or other liquid chromatographic separations (Niall, H. D., in: *Methods in Enzymology*, 27:942–1011 (1973) and Creighton, T. E., Proteins: Structures and Molecular Principles (W.H. Freeman, NY, 1984)). The amino acid sequence of the peptide is deduced from the molecular weight differences observed in the resulting MS fragmentation pattern of the peptide using the published masses associated with individual amino acid residues in the MS (Biemann, K., in: *Methods in Enzymology.*, 193:888 (1990), and has been codified into a semi-autonomous peptide sequencing algorithm (Hines, et al., *J Am Soc Mass Spectrom*, 3:326–336 (1992)).

For example, in the mass spectrum of a 1425.7 Da peptide (HSDAVFTDNYTR) isolated in an MS/MS experiment acquired in positive ion mode, the difference between the full peptide 1425.7 Da and the next largest mass fragment ($y_{11}$, 1288.7 Da) is 137 Da. This corresponds to the expected mass of an N-terminal histidine residue that is cleaved at the amide bond. For this peptide, complete sequencing is possible as a result of the generation of high-abundance fragment ions that correspond to cleavage of the peptide at almost every residue along the peptide backbone. In the above-recited peptide sequence, the generation of an essentially complete set of positively-charged fragment ions that includes either end of the peptide is a result of the basicity of both the N- and C-terminal residues. When a basic residue is located at the N-terminus and/or C-terminus, most of the ions produced in the collision induced dissociation (CID) spectrum will contain that residue (see, Zaia, J., in: *Protein and Peptide Analysis by Mass Spectrometry*, J. R. Chapman, ed., pp. 29–41, Humana Press, Totowa, N.J., 1996; and Johnson, R. S., et al., *Mass Spectrom. Ion Processes*, 86:137–154 (1988)) since positive charge is generally localized at the basic site. The presence of a basic residue typically simplifies the resulting spectrum, since a basic site directs the fragmentation into a limited series of specific daughter ions. Peptides that lack basic residues tend to fragment into a more complex mixture of fragment ions that makes sequence determination more difficult.

Nucleic acid sequencing has historically been conducted through the synthesis of nucleic acid fragments containing random numbers of bases copied from a parent nucleic acid sequence, such as the methods defined by Sanger and Colson, *Proc. Natl. Acad. Sci.* (*USA*), 74:5463–5467 (1977); and Maxam and Gilbert METHODS IN ENZYMOLOGY, 65:499–560 (1980). A variation on the method described by Sanger and Colson uses an incomplete polymerase chain reaction (PCR) method to synthesize the ladder of DNA fragments (see, Nakamaye et al., *Nuc. Acids Res.*, 16(21):9947–9959 (1988)). Mass spectrometric methods have been developed for more rapid and multiplexed separation and identification of the DNA ladders, as described by Koster, U.S. Pat. Nos.

5,691,141 and 6,194,144; Monforte et al. U.S. Pat. No. 5,700,642, and Butler, et al. U.S. Pat. No. 6,090,558. In these methods the nucleic acid fragments are introduced simultaneously into the mass spectrometer and the sequence or number of "short tandem repeats" are deduced from the mass differences between individual elements of the synthesized mass fragment ladder. As described by Koster U.S. Pat. No. 6,194,144, it is both possible and desirable to sequence several nucleic acids simultaneously in parallel by differentially labeling the nucleic acid fragments synthesized from unique nucleic acid parent templates with different tags of sufficiently unique masses. Even using labels of unique mass, care must be given to avoid subfragmentation of the elements of the sequence ladder during ionization or ion transmission in the mass spectrometer, and to purify the nucleic acid fragments from other extraneous nucleic acids and confounding matrix contaminants so that an unambiguous sequence can be obtained from the resulting mass spectrum. These references are incorporated by reference in their entirety for all purposes.

Polysaccharide sequencing sequencing methods, utilizing mass tagging methods in the mass spectrometer have also been described by Rademacher et al. U.S. Pat. No. 5,100,778 and Parekh and Prime U.S. Pat. No. 5,667,984. In these methods a unique mass tag is attached to a purified polysaccharide sample, which is subsequently divided into aliquots that are subjected to different regimes of enzymatic and/or chemolytic cleavage to produce a series of labeled oligosaccharide fragments derived from the polysaccharide parent. These fragments are simultaneously introduced into a mass spectrometer and the sequence of sugars contained in the parent polysaccharide determined from the resulting mass ladder generated in the mass spectrum from the random labeled oligosaccharide fragments. It is recognized that increased throughput may be obtained by processing several different samples simultaneously in parallel through the use of different mass tags attached to each unique purified polysaccharide parent sample. Again, care must be taken with the oligosaccharide samples to avoid subfragmentation in the mass spectrum and to purify the labeled fragments from unlabeled oligosaccharide contaminants to avoid sequencing ambiguities.

Identification of the fatty acid composition and placement in lipids can be an important indicator of the state of a cell. For example, Oliver and Stringer, *Appl. Environ. Microbiol.*, 4:461 (1984) and Hood et al., *Appl. Environ. Microbiol.*, 52:788 (1986) both report a 99.8% loss of phospholipids on starvation of *Vibrio* sp. Cronan, *J. Bacteriol.*, 95:2054 (1968) found 50% of the phosphotidyldglycerol content of *Escherchia coli* K-12 were converted to cardiolipin within two hours of the onset of phosphate starvation and that the fatty acid composition also shifted significantly. The lipid composition of the cell membrane is also of medical interest because of its potential roles in drug and metabolite uptake, anchoring transmembrane proteins, viral recognition of cell surfaces, tumor proliferation and metastasis, and arterial disease.

Similar mass tag approaches have been described for the identification of individual components of combinatorially-synthesized chemical libraries by Sugarman et al. U.S. Pat. No. 6,056,926 and Brenner et al. *Proc. Natl. Acad. Sci. (USA)*, 89:5381–5383 (1992), where a unique mass tag label is concurrently synthesized with the chemical compound of interest on a solid surface and later used to identify the various processing steps applied to the solid surface. This mass label can be identified after cleavage from the solid surface by mass spectrometry. The limitation on the size of the library that can be produced via combinatorial approaches is the number of unique mass labels that can be generated and the ability to discriminate these labels from the compounds of interest.

Ness et al. U.S. Pat. No. 6,027,890, Schmidt et al. WO 99/32501, and Aebersold et al. WO 00/11208, all describe methods for differentially labeling biological molecules obtained from different sources with a different mass tag for each source. The samples may then be combined, post labeling, and processed together through separation reactions or affinity enrichment, such that individual compounds from each sample are assured to be treated identically in the mixture. The relative concentrations of individual differentially-labeled biological compounds are then determined by the relative abundances of the individual mass tags in the mass spectrum. Limitations on these methods are that the mass labels employed must behave virtually identically with respect to any processing of the sample mixture and ionization and transport of the resulting ions in the mass spectrometer. For this reason, labels are typically chosen that are chemical analogs (e.g., stable isotope analogs or are simple derivatives of one another). A limitation of these methods is the number of samples that can be commingled for a single parallel analysis, which is limited by the number of mass tag derivatives that can be synthesized with nearly identical separation behaviors and ionization and transmission efficiencies. Another limitation of these methods is the ability to distinguish the mass labeled molecules or cleaved labels from unlabeled biomolecules and matrix contaminants that may also be present in the sample introduced into the mass spectrometer. This latter limitation often means that the labeled sample must be extensively purified prior to mass spectral analysis and that subfragmentation of the labeled molecules in the mass spectrometer must be avoided.

Schmidt et al. WO 99/32501 (Jul. 1, 1999) describe the use of fluorine in place of hydrogen as a distinguishable mass defect element in cleavable mass labels. The basis for this work is the 0.009422 amu monoisotopic mass difference between these two elements. However, this is a very small mass difference, which can only be resolved with very high mass resolution mass spectrometers and at the lowest mass ranges in these mass spectrometers. The resolution of mass spectrometers depends on the mass range and is normally quoted in parts per million. For example, typical time-of-flight detectors common in the industry have a mass resolution of about 10 amu at a mass of 1 million amu (10 ppm). Therefore, the comparatively small mass difference between F and H is impossible to resolve above a mass of about 940 amu, and from a practical perspective at an even lower m/z.

Schmidt et al. further note that the mass defect of perfluorinated hydrocarbons can be distinguished from simple hydrocarbons. For example, the monoisotopic mass of a polyfluorinated aryl tag with a maximum stoichiometry of $C_6F_5$ is exactly 166.992015 amu. The monoisotopic mass of the closest hydrocarbon is 167.179975, which corresponds to a stoichiometry of $C_{12}H_{23}$ and an easily resolvable mass difference of about 1125 ppm. The mass of the minimum polyfluorinated aliphatic tag is 68.995209 amu, which corresponds to a $CF_3$ stoichiometry. The closest monoisotopic hydrocarbon mass to this is 69.070425, corresponding to a $C_5H_9$ stoichiometry and a difference of 1089 ppm.

However, for organic molecules that include heteroatoms, such as N and O, which are typical in biological molecules, the mass defect of fluorine is not as easily distinguished. For example, any molecule that contains a stoichiometry of $C_3HO_2$ will have a monoisotopic mass that is only 35 ppm different from that of $CF_3$, making it nearly indistinguishable even at 69 amu. Similarly, any molecule that contains a monoisotopic stoichiometry of $C_7H_3O_5$ is only 36 ppm different from $C_6F_5$ at 167 amu.

When the stable isotopes of C, N, and O are included in the calculations, the mass defect of $C_6F_5$ reduces to an indistinguishable 1.4 ppm when compared to a molecule that contains a stoichiometry of $[^{12}C]_4[^{13}C]_2[^{15}N]_3[^{16}O]_2$. Similarly, the mass defect for $CF_3$ reduces to a mere 29 ppm compared to a molecule that contains $[^{12}C]_2[^{13}C][^{16}O]_2$ stoichiometry. As the overall mass of the tag increases beyond 200 amu, the mass defect introduced even with multiple fluorines rapidly becomes indistinguishable among the defects of the other heteroatoms and stable isotopes. Adding even more fluorines to the molecule is often not practical due to solubility constraints.

The general problem of deconvolving individual peaks of interest from complex mass spectral data has been previously described for complex mixtures of small molecules, (see Stein, S. E., "An integrated method for spectrum extraction and compound identification from GC/MS Data," *J Am Soc Mass Spect*, 10:770–781 (1999) and Mallard, G. W. and J. Reed, "Automated Mass Spectral Deconvolution & Identification System, AMDIS-User Guide" (US Department of Commerce, Gaithersburg, Md., 1997)) particularly when coupled to time resolved separation methods (e.g., GC/MS and LC/MS). However, these techniques have not been applied to biopolymer (e.g., protein, nucleic acid, and polysaccharide) fragmentation spectra for the purpose of sequence determination. In fact, these methods typically attempt to identify the intact chemical species and generally seek to avoid fragmenting conditions in the MS. Nor, have they been coupled to the identification of labeled biomolecule ions containing unique mass tags.

Extending the concept of simplifying the CID spectrum of a peptide by including a charge concentrating moiety on either terminus of the peptide, others have demonstrated that attaching a hard positive charge to the N-terminus directs the production of a complete series of N-terminal fragment ions from a parent peptide in CID experiments regardless of the presence or absence of a basic residue at the N-terminus. See, Johnson, R. S., et al., *Mass Spectrom. Ion Processes*, 86:137–154 (1988); Vath, J. E., et al., *Fresnius Z Anal. Chem.*, 331:248–252 (1988); Stults, J. T., et al., *Anal. Chem.*, 65:1703–1708 (1993); Zaia, J., et al., *J. Am. Soc. Mass Spectrom.*, 6:423–436 (1995); Wagner, D. S., et al., *Biol. Mass Spectrom.*, 20:419–425 (1991); and Huang, Z.-H., et al., *Anal. Biochem.*, 268:305–317 (1999). Theoretically, all fragment ions are produced by charge-remote fragmentation that is directed by the fixed-charged group. See, Tomer, K. B., et al., *J. Am. Chem. Soc.*, 105:5487–5488 (1983).

Peptides have been labeled with several classes of fixed-charge groups, including dimethylalkylammonium, substituted pyridinium, quaternary phosphonium, and sulfonium derivatives. Characteristics of useful labels include, ease of synthesis, increase in ionization efficiency of labeled peptides, and formation from a labeled peptide of a specific fragment ion series with minimal unfavorable label fragmentation. Zaia (in: *Protein and Peptide Analysis by Mass Spectrometry*, J. R. Chapman, ed., pp. 29–41, Humana Press, Totowa, N.J., 1996) reported that the labels satisfying these criteria include those of the dimethylalkylammonium class and quarternary phosphonium derivatives. Moreover, it has been reported that substituted pyridinium derivatives are useful in high-energy CID. See, Bures, E. J., et al., *Anal. Biochem.*, 224:364–372 (1995) and Aebersold, R., et al., in: *Protein Science*, pp. 494–503 (Cambridge University Press, 1992).

Despite some progress in analytical methodology, protein identification remains a major bottleneck in field of proteomics. For example, it can require up to 18 hours to generate a protein sequence tag of sufficient length to allow the identification of a single purified protein from its predicted genomic sequence (see, Shevchenko, A., et al., *Proc. Natl. Acad. Sci.* (*USA*), 93:14440–14445 (1996)). Moreover, although unambiguous protein identification can be attained by generating a protein sequence tag (PST, see Clauser, K. R., et al., *Proc. Natl. Acad. Sci.* (*USA*), 92:5072–5076 (1995) and Li, G., M., et al., *Electrophoresis*, 18:391–402 (1997)), limitations on the ionization efficiency of larger peptides and proteins restrict the intrinsic detection sensitivity of MS techniques and inhibit the use of MS for the identification of low abundance proteins. Furthermore, limitations on the mass accuracy of time of flight (TOF) detectors can also constrain the usefulness of presently utilized methods of MS/MS sequencing, requiring that proteins be digested by proteolytic and/or chemolytic means into more manageable peptides (see Ambler, R. P., in: *Methods in Enzymology*, 25:143–154 (1972) and Gross, E., in: *Methods in Enzymol.*, 11:238–255 (1967) prior to sequencing. In addition, previously described MS ladder sequencing algorithms fail on proteins because the abundance of peptide fragments generated during CID of such large molecules and inability to identify an appropriate parent ion to initiate the sequence effectively obscure the mass ladder.

Two basic strategies have been proposed for the MS identification of proteins after their separation from a protein mixture: 1) mass profile fingerprinting ('MS fingerprinting') (see, James, P., et al., *Biochem. Biophys. Res. Commun.*, 195:58–64 (1993) and Yates, J. R., et al., *Anal. Biochem.*, 214:397–408 (1993)); and 2) sequencing of one or more peptide domains by MS/MS ('MS/MS sequencing')(see Mann, M., paper presented at the IBC Proteomics conference, Boston, Mass. (Nov. 10–11, 1997); Wilm, M., et al., *Nature*, 379:466–469 (1996); and Chait, B. T, et al., *Science*, 262:89–92 (1993)). MS fingerprinting is achieved by accurately measuring the masses of several peptides generated by a proteolytic digest of the intact protein and searching a database for a known protein with that peptide mass fingerprint. MS/MS sequencing involves actual determination of one or more PSTs of the protein by generation of sequence-specific fragmentation ions in the quadrapole of an MS/MS instrument.

Clauser et al., *Proc. Natl. Acad. Sci.* (*USA*), 92:5072–5076 (1995) have suggested that proteins can only be unambiguously identified through the determination of PSTs that allow reference to the theoretical sequences determined from genomic databases. Li et al., *Electrophoresis*, 18:391–402 (1997) appear to have proven this assertion by finding that the reliable identification of individual proteins by MS fingerprinting degenerated as the size of the comparative theoretical peptide mass database increased. Li et al., ibid., also reported that they were only able to obtain peptide maps for the highest abundance proteins in the gel because of sensitivity limitations of the MS, even though their matrix assisted laser desorption MALDI methodology was demonstrated to improve the detection sensitivity over previously reported methods. Clearly, rapid and cost effective protein sequencing techniques will improve the speed and lower the cost of proteomics research. Similarly, as described by Koster, the preparation and purification of nucleic acids prior to sequencing, even by mass spectrometers, increases the time and cost of nucleic acid sequencing. Improving the discrimination ability of the mass spectrometer, such that multiple protein, nucleic acid, polysaccharide, or other sequences can be determined in parallel or specific ions can be better differentiated from unlabeled organic material, has considerable utility over existing methods.

The present invention provides such methods.

SUMMARY OF THE INVENTION

The present invention provides the application of mass defect labeling to a wide variety of molecules. Because the methods of the invention can be applied to during either "in-source" or collision induced dissociation of the oligomer in a quadrapole, the method preferentially eliminates the need for the chemical synthesis of oligomer fragments (e.g., chemolytic or enzymatic digestion, or Sanger or PCR sequencing fragment synthesis). Thus, the present methods provide oligomer sequencing times that are significantly reduced from the times obtainable using other methods. The method can also be applied as an improvement over more conventional oligomer sequencing approaches, such as MS/MS sequencing of peptides, Sanger and PCR sequencing by mass spectrometry (as described by Koster and Butler et al), and polysaccharide sequencing as described by Rademacher et al. and Parekh et al. By allowing an increased number of samples to be simultaneously processed in parallel. Increasing the ability to distinquish a larger number of tags in a single mass spectrum allows larger combinatorial libraries to be synthesized or screened. Moreover, because the oligomers being sequenced are highly fragmented using the present methods, the ionization efficiency and the volatility of the resulting fragments are higher than those of the parent oligomer, thus leading to a detection sensitivity that is improved over other methods.

In one aspect, the present invention provides a method for sequencing a terminal portion of an oligomer or polymer, comprising:

(a) contacting said oligomer with a labeling moiety to covalently attach a label to the terminus of the oligomer and form a labeled oligomer, the labeling moiety comprising at least one element having an atomic number from 17 to 77, with the proviso that said element or elements is other than sulfur or phosphorus; and the oligomer contains no elements in its structure having an atomic number between 17 and 77 with the exception of sulfur or phosphorus, (b) fragmenting the labeled oligomer using an enzymatic, chemolytic or mass spectrometric fragmentation method to produce labeled oligomer fragments; and (c) analyzing the labeled oligomer fragments using a mass spectrometric sequencing method or algorithm to determine the sequence of at least two monomeric elements near the label.

In one group of embodiments, wherein the oligomer is a protein, peptide, or nucleic acid the method further comprises:

(d) identifying the protein or gene by using the sequence of the at least two terminus residues to search predicted sequences from a database of gene sequence data.

In another aspect, the present invention provides a method for sequencing a portion of an oligomer in an oligomer mixture, the method comprising:

(a) contacting the oligomer mixture with a labeling moiety to covalently attach a label to one terminus of the oligomer and form a labeled oligomer mixture, the labeling moiety comprising at least one element having an atomic number from 17 to 77, with the proviso that said element is other than sulfur or phosphorus; and the oligomer contains no elements in its structure having an atomic number between 17 and 77 with the exception of sulfur or phosphorus, (b) separating individual labeled oligomers in the oligomer mixture; and (c) analyzing the labeled oligomers from step (b) by a mass spectrometric method to determine the sequence of at least two terminal residues.

In one group of embodiments, wherein the oligomer is a protein, the method further comprises:

(d) identifying the protein by using the sequence of at least two C-terminus or two N-terminus residues in combination with a separation coordinate of the labeled protein and the protein terminus location of the sequence to search predicted protein sequences from a database of gene sequence data.

In yet another aspect, the present invention provides a method for structure and function analysis of an oligomer having a plurality of monomers, the method comprising:

(a) contacting the oligomer with a mass defect labeling reagent to differentially label exposed monomers and unexposed monomers and produce a differentially labeled oligomer, wherein the mass defect labeling reagent comprises at least one element having an atomic number of from 17 to 77 that is other than sulfur or phosphorus; and the oligomer contains no elements in its structure having an atomic number between 17 and 77 with the exception of sulfur or phosphorus, (b) analyzing the differentially labeled oligomer by a mass spectrometric method to determine sequences of the oligomer that are exposed in the three-dimensional structure and sequences of the oligomer that are unexposed in the three-dimensional structure.

In yet another aspect, the method can be applied to quantitative determination of labeled biomolecules from mixtures, the method comprising:

(a) contacting the biomolecules obtained from one sample with a labeling moiety to covalently attach a label to the biomolecules and form a labeled biomolecule mixture, contacting a similar set of biomolecules obtained from at least one other sample with a labeling moiety to covalently attach a label to the biomolecules and form a labeled biomolecule, the first labeling moiety comprising at least one element having an atomic number from 17 to 77, and each successive labeling moiety comprising at least one additional element having an atomic number from 17 to 77; with the proviso that said elements are other than sulfur or phosphorus; and the biomolecule contains no elements in its structure having an atomic number between 17 and 77 with the exception of sulfur or phosphorus;

(b) mixing the differentially labeled biomolecule samples from each source;

(c) optionally separating the biomolecules by affinity or other means; and (c) analyzing the differentially labeled biomolecules by a mass spectrometric method to determine relative quantities of the individual labeled biomolecules or labels cleaved from said labeled biomolecules.

In yet another aspect, the method can be used to encode combinatorial libraries, the method comprising:

(a) contacting the synthetic surface with a tag monomer to identify the chemical process to which the synthetic surface is (or will be) exposed and form a labeled synthetic surface, the tag monomer comprising at least one element having an atomic number from 17 to 77, (b) optionally contacting the synthetic surface with successive tag monomers to identify subsequent chemical process steps to which the synthetic surface is (or will be) exposed and form a successively labeled synthetic surface, the tag monomers comprising at least one element having an atomic number from 17 to 77, (c) cleaving the monomer tag(s) from the synthetic surface either as a single multiply-tagged molecule, or as a set of individual tags.

(d) analyzing the composition of the tag(s) by mass spectrometric method to determine the chemical processing history of the surface.

In each of the methods above, the use of a robust algorithm for terminally-labeled oligomer sequencing of the oligomer fragments provides advantages over conventional MS/MS sequencing algorithm approaches. One particular advantage is, for example, the ability to partially sequence full length oligomers (e.g., proteins or nucleic acids such as DNA and RNA) without the need for prior digestion into smaller fragments if mass spectrometric fragmentation techniques are used to generate the fragments. Another advantage is the ability to automatically filter out chemical noise (e.g., unlabeled oligomers or molecules and organic matrix contaminants) in the mass spectrum. Another advantage is that the method is self-starting based on the known mass defect of the label and does not require any knowledge of the parent ion size or composition to determine the sequence. Another advantage is that the method can be highly automated. Still another advantage is that fewer sequence ambiguities result due to the improved absolute mass accuracy gained by working at the low end of the mass spectrum. Yet another advantage is that better ionization efficiency and corresponding detection sensitivity result from using more energetic ionization conditions and the introduction of a hard or ionizable charge on the fragments through the addition of the label. Yet another advantage of introducing a charge through the label is the ability to determine partial oligomer sequences from regions of an oligomer that may not contain ionizable residues. It is obvious to those skilled in the art that the methods of the present invention may be applied for the sequence analysis of any organic polymer or relative quantification of any organic molecule between two or more samples with the proviso that a mass defect label can be attached to the organic polymer or molecules.

BRIEF DESCRIPTION OF THE DRAWINGS

FIG. 8A shows the deconvolved mass defect spectrum for a high mannose-type oligosaccharide digest labeled with Label 1.

DESCRIPTION OF THE INVENTION

Definitions

Figure 1:
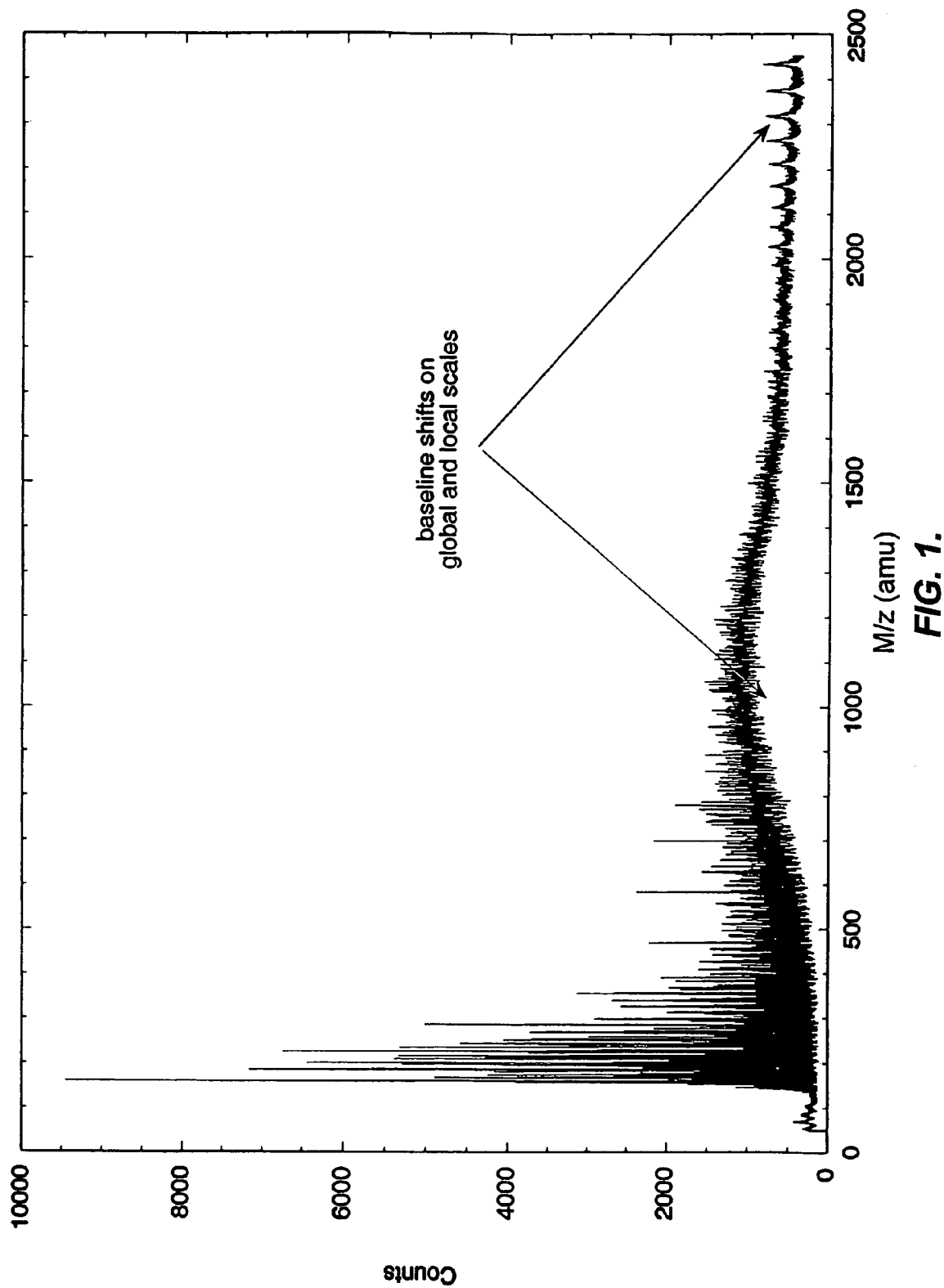
FIG. 1 shows the mass spectrum of glycogen phosphorylase taken at highly fragmenting conditions of 325V nozzle potential in a PE Biosystems Mariner mass spectrometer.

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and protein chemistry described below are those well known and commonly employed in the art. Standard techniques are used for peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., and Methods in Enzymology, Biemann, ed. 193:295–305, 351–360 and 455–479 (1993), which are incorporated herein by reference), which are provided throughout this document. The nomenclature used herein and the procedures in mathematical and statistical analysis, analytical chemistry, and organic synthesis described below are those known and employed in the art. Standard techniques, or modifications thereof, are used for chemical syntheses and chemical analyses.

The term "mass defect" or "mass defect label" refers to a portion of a label or the entire label that provides a mass sufficient and distinct to be readily identified in the mass spectrum of the sample. Accordingly, the mass defect is typically an element having an atomic number of from 17 to 77 and more specifically between 35 and 63, that is other than sulfur or phosphorus. The most effective mass defect labels for use with typical organic chemicals (even organic chemicals containing group 1 and group 2 heteroatoms), such as biomolecules, incorporate one or more elements having an atomic number of 35 to 63. Examples of the most preferred mass defects are the elements bromine, iodine, europium and yttrium.

As used herein, the term "oligomer" refers any polymer of residues wherein the residues are similar, though typically not identical. Generally, an oligomer is meant to include the naturally-occuring polymers such as proteins, oligonucleotides, nucleic acids, oligosaccharides, polysaccharides, and lipids, and the like. Oligomer may also refer to free radical, condensation, anionic, or cationic polymers of synthetic origin, such as but not limited to: acrylates, methacrylates, nylons, polyesters, polyimides, nitrile rubbers, polyolefins and block or random copolymers of different monomers in these classes of synthetic polymers. The oligomer that is subject to the analytical methods described herein will have a number of residues that is typical of their naturally occuring number. For example, an oligomer that is an oligonucleotide can have hundreds and even thousands of residues. Similarly, a protein will generally have one hundred or more residues (though the sequencing of smaller fragments, e.g., peptides, is also useful). An oligosaccharide will typically have from 3 to 100 sugar residues. A lipid will normally have 2 or 3 fatty acid residues.

As used herein, the terms protein, peptide and polypeptide refer to a polymer of amino acid residues. The terms also apply to amino acid polymers in which one or more amino acids are chemical analogues of corresponding naturally-occurring amino acids, including amino acids which are modified by post-translational processes (e.g., glycosylation and phosphorylation).

"Protein", as used herein, means any protein, including, but not limited to peptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. The amino acids may be either the D- or L-isomer. The L-isomers are generally preferred. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Protein sequencing tag," as used herein, refers to a contiguous series of at least two amino acids representing a partial sequence of a protein. A preferred PST includes a label of the invention or a fragment of a label of the invention or an ionized derivative of a label of the invention.

The term "nuclear binding energy" refers to the mass disparity between the calculated and actual nuclear masses of the elements. It is defined as the mass equivalent (according to the theory of relativity) of the energy needed to tear a nucleus apart into its constituent isolated nucleons. See Bueche, F., "Principles of Physics" (McGraw-Hill, NY, 1977).

The term "deconvolution" broadly defines mathematical procedures and algorithms for recovering information of interest from data that contains both random and periodic noise, or which has been otherwise obscured by the interaction with electronic or physical collection methods.

The term "alkyl" is used herein to refer to a branched or unbranched, saturated or unsaturated, monovalent hydrocarbon radical, generally having from about 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as, for example, lower alkyl, aryl, acyl, halogen (i.e., haloalkyl, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "lanthanide series" refers to the elements in the periodic table with atomic numbers between 57 and 71.

The term "hydroxy" is used herein to refer to the group —OH.

The term "amino" is used to designate —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another group.

"Substituted heteroaryl" refers to heteroaryl as just described wherein the heteroaryl nucleus is substituted with one or more functional groups such as lower alkyl, acyl, halogen, haloalkyl (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, haloalkyl (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

The term "chelate" refers to the strongly associative binding of a metallic element or metal ion to a substantially organic molecule through non-covalent means. These are alternately known as organometallic molecules.

General

The present invention resides in a mass spectrometric method for improved discrimination of labeled and unlabeled molecules or fragments of molecules in the mass spectrometer. This method can be used for oligomer sequence determination and for increased combinatorial complexity that can be discriminated in the mass spectrum. The present method is practiced by labeling the terminus of a molecule or an oligomer with a labeling reagent that incorporates a mass defect, and discriminating the resulting mass defect labeled molecules from other unlabeled molecules or unlabeled oligomer fragments in the mass spectrum.

In one embodiment, labeled oligomers may be sequenced with the intact labeled oligomer fragmented in either the ionization zone of a mass spectrometer (e.g., in-source fragmentation) or in the collision cell of a MS/MS instrument, and using a mathematical algorithm to determine the terminal sequence of the oligomer from the labeled end. In another embodiment, labeled oligomers may be synthesized from a parent template or chemolytically or enzymatically digested to form fragments that comprise a sequencing ladder of labeled fragments that are algorithmically identified in the mass spectrum from the differential mass defect of the label. Labeled oligomers and oligomer fragments are differentiated from unlabeled oligomers and fragments by their unique mass signatures in the resulting mass spectrum and are deconvoluted from non-labeled oligomer fragments and peaks associated with the ionization matrix and contaminating oligomers and fragments by their relative abundance and/or unique mass signatures (due to the mass defect). A cumulative ranking system is used by the algorithm to strengthen the certainty of the sequence determined at successive residues of the mass ladder. In some embodiments, this process is accomplished in less than 1 min for a purified labeled protein, yielding a 500 to 1000-fold more rapid method than current MS/MS protein sequencing techniques.

In one embodiment, the labeled oligomers are highly fragmented in the MS by collision induced dissociation (CID). CID can be accomplished in the ionization zone (e.g., in-source) or in a collision cell through high energy impact with non-oligomer gases introduced to the collision zone. Preferred labels lead to increased ionization efficiency and enhanced volatility of the resulting labeled oligomer fragment ions, relative to the parent oligomer, thus improving the overall detection sensitivity. Preferred labels impart a unique mass signature to the fragments to which they are attached. In a particularly preferred embodiment, the unique mass signature may consist of one or more elements incorporated into the label that contain a nuclear binding energy that substantially differs from those of the elements associated with the oligomer residues (e.g., C, H, O, N, P and S). In another embodiment, a mixture of isotopically distinct versions of a label may be used concurrently with the relative abundance of the resulting isotopic pairs to deconvolute peaks of interest in the mass spectrum. In another embodiment, label analogs that differ by addition of one or more methyl or methylene units and/or isotopically pure analogs (e.g., D vs. H or Cl) may be used to uniquely distinguish peaks of interest in the mass spectrum. In still another embodiment, peaks associated with labeled oligomers, fragments or ions may be deconvolved from unlabeled oligomers or fragments by their masss shift. The sequence of the oligomer or sequence tag is preferably constructed from the low molecular weight end of the mass spectrum, providing advantages over prior methods, such as greater absolute mass accuracy and more facile sequencing. In the case of proteins, this advantage will include resolution of Q and K residues, from the resulting labeled peptide fragments.

The selection of an appropriate label for this technique requires consideration of several criteria. First, the label is preferably robust enough to survive the fragmentation conditions of the MS. Second, the label preferably also creates a unique mass/charge (m/z) signature (e.g., a mass defect) that is distinguishable from any unlabeled oligomer fragments generated from internal scissions of the oligomer backbone or from other unlabeled organic molecules that may be present in the sample. Third, the label may also carry an ionizable or permanently ionized group to ensure that fragmentation produces high-abundance ions that include even uncharged terminal residues.

In contrast to the limited utility of F as a mass defect element (Schmidt et al. WO 99/32501 (Jul. 1, 1999)), the present invention uses mass defect elements that present a much greater mass difference and thus broader utility. For example, a single iodine substitution on an aryl group creates a mass defect of 0.1033 amu more than a 5 fold improvement over that of 5 aryl F substitutions. A single I on an aryl ring ($C_6H_4I$) exhibits a monoisotopic mass of 202.935777 amu. This is 192 ppm different from the nearest combination of stable isotope and heteroatom-containing organic molecule ($[^{12}C]_9[^{15}N][^{16}O]_5$) at 202.974687 amu. Therefore, a single substitution of any of the elements that exhibit a mass defect similar to that of I (i.e., atomic numbers between 35 and 63) will yield a discernable mass defect (at the 10 ppm level) to a total mass of 3,891 amu for any combination of organic heteroatoms. Two such elements will exhibit a discernable mass defect to a total mass of 7,782 amu. Three such elements will exhibit a discernable mass defect to a total mass of 11,673 amu. Alternatively, single, double, and triple additions of I (or an equivalent mass defect element) can be discriminated from each other to a total mass of 4,970 amu in a mass spectrum with 10 ppm mass resolution.

The present invention incorporates a robust algorithm for the identification of mass defect labeled molecules or fragments and determination of the oligomer sequence from labeled oligomer fragments in the mass spectrum. This algorithm searches the spectral data for all possible oligomer sequences starting only from the mass of the label, which is known. The algorithm uses both the mass to charge ratio of the labeled oligomer fragments and the relative abundance of the resulting MS peaks to rank all possible oligomer sequences. A cumulative (forward-looking) ranking is used to eliminate sequences as successive numbers of certain residues are found in the mass spectrum. In a preferred embodiment, chemical noise is selectively deconvolved from the mass spectrum prior to the application of the sequencing algorithm. Unlike previous sequencing algorithms, the current algorithm is robust because it can be implemented without human intervention either to define a starting or parent ion, or to identify or qualify prospective sequence peaks in the mass spectrum. In another embodiment the highest ranked sequence possibilities can be further qualified by their existence in a database of possible oligomer sequences predicted from sequence data, particularly one limited to the organism from which the oligomer was obtained. In another embodiment, the highest ranked sequence possibilities can be further qualified by the separation coordinates of the parent oligomer (e.g., isoelectric point and molecular weight of a protein) and/or its monomer composition.

The current invention incorporates one or more elements into the label that have a nuclear binding energy (often referred to as a mass defect) that moves the mass of the label to a unique mass position in the spectrum that no other stochiometric combination of the other elements may have. In this way, labeled fragments are more easily distinguished from chemical noise and may be detected with more accuracy, when present in lower relative abundances, and when present in more complex sample mixtures. In addition, the method can be used to help identify lower abundance labeled fragments produced by various ionization methods (e.g., d-, and w-ions produced by protein and peptide fragmentation).

The use of mass defects can also be applied to the quantification of the relative abundances of the same molecule obtained from two or more sources in a mass spectrometer (see, for example, WO 00/11208, EP1042345A1, and EP979305A1). Using this particular methodology, a label can be attached to an oligomer that differs from the other labels by the replacement of one element with a stable isotope of that element are added to the molecules from each source. The sources are mixed subsequent to labeling and the relative abundance of molecules or the labels from each source are quantified in the mass spectrum. The different isotopes are used to uniquely differentiate the peaks arising for the same molecule from each source. Modification of this method to incorporate one or more mass defect elements into the label can improve this quantification because the resulting labeled molecules or labels will be displaced from any chemical noise in the resulting mass spectrum.

The invention can be used in conduction with protein sequencing methods, such as inverted mass ladder sequencing (see, PCT publication WO 00/11208) and other MS protein sequencing, quantification, and identification methods, such as are outlined in U.S. Pat. No. 6,027,890, and PCT publications WO 99/32501 and WO 00/11208. Mass defect labeling as described herein, can also be applied to DNA sequencing methods by MS outlined in U.S. Pat. Nos. 5,700,642, 5,691,141, 6,090,558 and 6,194,144. Still further, mass defect labeling as described herein can be used to determine the sequence of polysaccharides (such as the glycosylation pattern of a protein). See general methods provided in U.S. Pat. Nos. 5,100,778 and 5,667,984.

More broadly, the method can be used to improve the identification (sequence determination) or quantification of any polymer from different sources, whether natural or synthetic, providing that a mass defect label can be covalently attached to a terminus of the polymer.

The invention may also be used for the structural identification or relative quantification of nonpolymeric chemical species from different sources, providing labels can be covalently attached to these molecules. Examples include: differential (diseased vs. healthy tissues) amino acid analysis; differential nucleotide analysis; differential saccharide analysis; differential fatty acid analysis and structure determination of unsaturated and branched fatty acids; lipid analysis and structural determination; and nutrient quality control applications, and combinatorial library tags (as outlined in U.S. Pat. No. 6,056,926 and by Brenner, S. and R. A. Lerner, "Encoded combinatorial chemistry," *Proc. Natl. Acad. Sci. (USA)*, 89:5381–5383 (1992)).

Turning first to the mass defect labeling of nucleic acids (e.g., DNA or RNA), each of U.S. Pat. Nos. 6,090,558 and 6,194,144 describe how DNA can be sequenced from synthesized fragments incorporating a unique mass label in the primer sequence. In contrast, the present invention provides that labeling is carried out using only labels having a mass defect, to distinguish the labeled fragments from unlabeled fragment and provide a more robust, yet sensitive method. Another advantage of the use of mass defect labels is the increased number of different nucleic acids that can be sequenced in parallel in this manner. The advantages of mass defect labeling (rather than a more general labeling process) were not disclosed in the earlier work.

Similarly, WO 00/11208, EP1042345A1, EP979305A1, and U.S. Pat. No. 6,027,890, describe the use of unique mass labels for differential analysis and quantification of protein and DNA molecules between different sources. However, each of these references fail to anticipate or identify the advantages of incorporating a mass defect element into the unique mass label.

Turning next to oligosaccharide labeling, EP 698218B1 describes the use of labeled carbohydrates and their use in assays and U.S. Pat. Nos. 5,100,778 and 5,667,984 describe the use of mass labels to determine the oligosaccharide sequence by MS. While the techniques disclosed therein might be applicable to labeling with unique mass tags, the incorporation of a mass defect in the label for the purposes of shifting MS peaks to non-interferring regions of the spectra are not disclosed or appreciated. Thus, application of the mass defect labeling methodology described herein provides methods to identify the sugar sequence of a complex carbohydrate by labeling the carbohydrate as described in the prior art (with suitable modification for the incorporation of a mass defect in the label) or by any other method available to those skilled in the art and identifying the mass defect labeled fragments in the mass spectrometer. The carbohydrate structure can be determined in whole or in part by mass addition from the smallest labeled fragments similar to the DNA and MS/MS protein sequencing methods described above. Again, incorporation of a mass defect element into the label has utility for isolating the labeled fragments from the chemical noise.

Turning next to lipids, the fatty acid composition and sequence can be determined by labeling the fatty acids enzymatically digested from the glycidol backbone, where different mass defect labels are applied as tags for different enzyme digestions that are sequence specific.

In each of the applications noted, the amino acids, lipids, and nucleotides can be derivatized by methods generally available to those skilled in the art. If isotopically-distinct labels are used for such derivatization of these molecules obtained or extracted from different samples, then differential quantification analysis may be performed by MS. However, in each instance, the incorporation of a mass defect element into the label improves the ability to isolate the labeled molecules from other chemical noise in the spectrum and obtain more accurate relative abundance measurements. However, unanticipated in the prior art is the incorporation of different numbers of mass defect elements into the labels to increase the number of samples that can be simultaneously discriminated in the resulting mass spectrum. This methodology can also be applied to improve the isolation and identification of metabolites in biological samples (see, for example, U.S. Ser. No. 09/553,424, filed Apr. 19, 2000), where a mixture of isotopically-enriched metabolites obtained from a source are subsequently derivatized with a label containing a mass defect to facilitate the identification and quantification of the isotopically-enriched metabolite from the non-enriched form.

In addition to sequencing and identification of oligomers, mass defect labeling can be used to probe the structure and function of biologically active macromolecules (e.g., oligomers such as proteins, nucleic acids and oligosaccharides).

Deuterium exchange methodology (see, Andersen, et al., *J. Biol. Chem.* 276(17):14204–11 (2001)) has been used to probe secondary and higher-order protein structure and regions involved in ligand binding. Moieties that are exposed to solvent and are not buried or hidden by bound ligands will exchange hydrogen for deuterium at a much faster rate in the presence of deuterated water. Subsequent proteolysis of the protein and mass spectral analysis of the deuterated and nondeuterated proteolytic fragments can elicit information about which moieties are involved in specific higher-order structural elements or in binding epitopes.

Improved methods are provided herein, in which mass defect elements are used to label an oligomer or other macromolecule, in lieu of deuterium. By using small molecules incorporating elements with mass defects that can target specific reactive groups and analyzing fragmentation patterns of, for example, intact or proteolyzed protein samples, information about structure or function can be obtained by searching for products that are labeled singly or multiply or unlabeled with the mass defect label. This information is obtained more readily and unequivocally by the reduction of chemical noise that the mass defect label provides. Specifically, an active protein can be exposed to a mass defect label such as bromine or iodine gas, which targets protein tyrosine residues. Tyrosine residues are labeled differentially depending on their geometric loci (i.e., surface vs. buried) and their participation in ligand binding. The protein can be fragmented, with or without prior proteolysis, and the tyrosine labeling pattern probed easily in the mass spectrometer by searching for peaks arising from incorporation of bromine or iodine atoms.

Another area in which mass defect labels have beneficial use is in combinatorial analysis of both small molecules and macromolecules that do not already contain elements with mass defects (e.g., most biologically derived materials). In this application, a complex mixture of entities (e.g., proteins and peptides, including antibodies and enzymes, polysaccharides, polynucleotides, pharmaceuticals, or catalysts)

generated as a combinatorial library can be probed for activity and identified by incorporating tagging elements as described in U.S. Pat. No. 6,056,926 and by Brenner, S. and R. A. Lerner, Encoded combinatorial chemistry, *Proc. Natl. Acad. Sci.*, 89:5381–5383 (1992). By increasing the number of tags, and using tags that incorporate a mass defect element, a larger combinatorial library can be evaluated. Those entities which have desired binding characteristics will display a shift in mass equal to the mass defect label. Even in a very complex mixture, it is straightforward to identify the shifted peaks as a result of the mass defect.

DESCRIPTION OF THE EMBODIMENTS

Sequencing Terminal Portions of Oligomers

In view of the above, the present invention provides in one aspect, a method for sequencing a terminal portion of an oligomer, comprising:

(a) contacting said oligomer with a labeling moiety to covalently attach a label to the terminus of the oligomer and form a labeled oligomer, the labeling moiety comprising at least one element having an atomic number from 17 to 77, with the proviso that said element is other than sulfur or phosphorus;

(b) fragmenting the oligomer by enzymatic, chemolytic, or a mass spectrometric fragmentation method, and (c) analyzing the fragmented labeled oligomer using a mass spectrometric fragmentation method to determine the sequence of at least two terminal residues.

In this aspect of the invention the oligomer can be obtained from essentially any source (e.g., tissues samples, biopsies, cell extracts, and the like). Preferably, the oligomer is isolated and purified to be free of interfering components. The isolated oligomer can be contacted with a labeling moiety to covalently attach a label to the terminus of the oligomer to form a labeled oligomer, suitable for analysis by mass spectrometric fragmentation methods. Specific methods and conditions for labeling an oligomer can be carried out according to established methods depending on the functional groups present in the oligomer and the reactive groups present in the labeling agent. Typically, covalent attachment can be made through, for example, the formation of amide, ester, urea, thiourea, dissulfide, phosphodiester, sulfonate, imine and hydrazide linkages between the label and the oligomer. A more complete discussion of attachment chemistry is provided is sections below.

Fragmentation of the resultant labeled oligomer can be accomplished via chemolytic, enzymatic or mass spectrometric methods. Alternatively, fragments may be generated by incomplete replication of the parent molecule (e.g., sequencing of nucleic acids).

Following the fragmentation of the labeled oligomer sample, the fragments are analyzed using a mass spectrometric method to determine the sequence of at least two, more preferably three, still more preferably four, five or six terminal residues. In some embodiments the sequence of seven or more terminal residues is determined. A preferred mass spectrometric method is described in the Examples below.

In one group of preferred embodiments, the labeling moiety comprises at least one element having an atomic number of 35 to 63, still more preferably 39 to 58. In a group of particularly preferred embodiments, the moiety comprises at least one element selected from bromine, iodine, europium and yttrium. Still more preferably, the labeling moiety has from one to three bromine or iodine atoms.

Preferred oligomers to be sequenced in this aspect of the invention include a protein (or peptide), an oligonucleotide, an oligosaccharide and a lipid. More preferably, the oligomer is a protein (or peptide) or an oligosaccharide.

In a related aspect, the invention provides a method for sequencing a portion of an oligomer in an oligomer mixture, the method comprising:

(a) contacting the oligomer mixture with a labeling moiety to covalently attach a label to one terminus of the oligomer and form a labeled oligomer mixture, the labeling moiety comprising at least one element having an atomic number from 17 to 77, with the proviso that said element is other than sulfur or phosphorus;

(b) separating individual labeled oligomers in said oligomer mixture; and (c) analyzing the labeled oligomers from step (b) by a mass spectrometric method to determine the sequence of at least two terminal residues.

The oligomer mixture in this aspect of the invention can be a mixture of proteins, a mixture of oligonucleotides, a mixture of oligosaccharides, a mixture of lipids and the like, and is typically obtained from a biological source, such as a cell lysate. Alternatively, samples can be obtained from animal tissues (diseased or healthy), plant extracts, bacterial sources, viral sources, and the like. Preferably, the oligomer mixture has been purified to reduce the amount of potentially interferring components using methods known in the art.

Labeling of the oligomers in the oligomer mixture can generally be carried out as described above for a single oligomer, using the labels described in more detail below. Separating of the labeled oligomers in the oligomer mixture can be accomplished using methods such as capillary electrophoresis, high performance liquid chromatography (HPLC), gel electrophoresis (in all its forms), chromatography (e.g., size exclusion, ion exchange, etc.), or gas chromatography, to name a few. The separated individual labeled oligomers obtained from the separation process can then be analyzed using the mass spectrometric methods described herein to determine the sequence of at least two terminal residues. Preferably, the mass spectometic method is ESI-TOF MS.

In one group of preferred embodiments, the labeling moiety comprises at least one element having an atomic number of 35 to 63, still more preferably 39 to 58. In a group of particularly preferred embodiments, the moiety comprises at least one element selected from bromine, iodine, europium and yttrium. Still more preferably, the labeling moiety has from one to three bromine or iodine atoms.

In one related aspect, the invention provides a method for sequencing the terminal portion of an oligomer, comprising:

(a) contacting a first oligomer sample with a labeling moiety to covalently attach a label to the terminus of the oligomer and form a labeled oligomer, the labeling moiety having one element with an atomic number from 17 to 77, with the proviso that the element is other than sulfur or phosphorus;

(b) contacting a second oligomer sample with a labeling moiety to covalently attach a label to the terminus of the oligomer and form a second labeled oligomer, the labeling moiety having two elements with an atomic number from 17 to 77, with the proviso that the elements can be the same or different but are other than sulfur or phosphorus;

(c) optionally, repeating step (b) from one to three times with additional oligomer samples, wherein the labeling moieties have three, four or five elements, respectively, with an atomic number from 17 to 77, with the proviso that the elements are other than sulfur or phsophorus;

(d) mixing the labeled oligomers from steps (a) through (c);

(e) fragmenting the labeled oligomers using an enzymatic, chemolytic or mass spectrometric fragmentation method to produce labeled oligomer fragments; and (f) analyzing the labeled oligomer fragments using a mass spectrometric fragmentation method to determine the sequence of at least two terminal residues.

In yet another related aspect, the present invention provides a method of sequencing a portion of an oligomer, comprising:

(a) fragmenting aliquots of the oligomer using one or more specific enzymatic or chemolytic fragmentation methods to produce oligomer fragments, wherein a different fragmentation method is applied to each aliquot;

(b) contacting a first aliquot of oligomer fragments with a first labeling moiety to covalently attach the first labeling moiety to the terminus of the oligomer fragments and form labeled oligomer fragments, the first labeling moiety having one element with an atomic number from 17 to 77, with the proviso that the element is other than sulfur or phosphorus;

(c) optionally contacting the other aliquots of oligomer fragments with other distinct labeling moieties to covalently attach the distinct labeling moieties to the termini of the oligomer fragments and form labeled oligomer fragments, the distinct labeling moieties having two or more elements with an atomic number from 17 to 77, with the proviso that the elements are other than sulfur or phosphorus;

(d) optionally mixing the aliquots of labeled oligomer fragments; and (e) analyzing the labeled oligomer fragments using a mass spectrometric fragmentation method to determine the sequence of at least two residues of the oligomer.

In certain preferred embodiments, the fragmented labeled oligomers are reallocated and subjected to additional steps of labeling and fragmentation.

In still another related aspect, the invention provides a method for sequencing a portion of an oligomer, comprising:

(a) preparing several aliquots of an oligomer sample (b) contacting the oligomer in each aliquot with a labeling moiety to covalently attach a label to one terminus of the oligomer and form a labeled oligomer mixture, wherein each aliquot is labeled with a label containing a different number of elements having an atomic number from 17 to 77, with the proviso that said elements are other than sulfur or phosphorus, (c) fragmenting the labeled oligomer in each aliquot by a different enzymatic or chemolytic method, (d) mixing the reaction products from each aliquot (e) analyzing the fragmented labeled oligomer mixture using a mass spectrometric fragmentation method to determine the sequence of at least two terminal residues.

In a related variation, the invention provides a method for simultaneously analyzing multiple reaction products for determining sequences of an oligomer sample, the method comprising:

(a) preparing several aliquots of an oligomer sample;

(b) fragmenting the oligomer in each aliquot by a different enzymatic or chemolytic method;

(c) contacting the reaction products in each aliquot with a labeling moiety to covalently attach a label to one terminus of the reaction products to form a labeled reaction product mixture, wherein each aliquot is labeled with a label containing a different number of elements having an atomic number from 17 to 77, with the proviso that said elements are other than sulfur or phosphorus;

(d) mixing the labeled reaction product mixtures from each aliquot; and (e) analyzing the combined labeled reaction product mixtures of step (d) using a mass spectrometric method to determine the sequence of at least two monomers in the oligomer.

In another variation, the invention provides a method for sequencing a plurality of oligonucleotides in a sample, the method comprising:

(a) labeling synthetic primers by contacting each primer with a labeling moiety to covalently attach a label to one terminus of each primer to form a labeled primer mixture, wherein each primer is labeled with a label containing a different number of elements having an atomic number from 17 to 77, with the proviso that the elements are other than sulfur or phosphorus;

(b) adding a sample template to the labeled primer mixture;

(c) synthezing a plurality of labeled oligomers from the sample template by enzymatic or chemical methods, and (d) analyzing the labeled oligomers synthesized in step (c) using a mass spectrometric method to determine the sequence of the sample template.

In each of these latter aspects and variations, preferred labels are those containing elements having atomic numbers of from 35 to 63, more preferably, 39 to 58 as described above for earlier aspects of the invention. Other preferred embodiments are also the same as have been described above.

Labeled Proteins

The labeling of proteins with various agents in an aqueous or mixed aqueous/organic solvent milieu is known in the art and a wide range of labeling reagents and techniques useful in practicing the present invention are readily available to those of skill in the art. See, for example, Means et al., CHEMICAL MODIFICATION OF PROTEINS, Holden-Day, San Francisco, 1971; Feeney et al., MODIFICATION OF PROTEINS: FOOD, NUTRITIONAL AND PHARMACOLOGICAL ASPECTS, Advances in Chemistry Series, Vol. 198, American Chemical Society, Washington, D.C., 1982; Feeney et al., FOOD PROTEINS: IMPROVEMENT THROUGH CHEMICAL AND ENZYMATIC MODIFICATION, Advances in Chemistry Series, Vol. 160, American Chemical Society, Washington, D.C., 1977; and Hermanson, BIOCONJUGATE TECHNIQUES, Academic Press, San Diego, 1996.

Labeling can be conducted and PSTs determined from either the N- or C-terminal end of the protein. About 59–90% of eukaryotic proteins are N-terminal acetylated (see, Creighton, T. E., Proteins: Structures and Molecular Principles (W.H. Freeman, NY, 1984) and are thus refractory to N-terminus labeling. However, the natural N-acetyl group of such proteins can sometimes be used as a label for purposes of this invention, but only where one or more of the amino acids within 4 residues of the N-terminus is ionizable (e.g., is a lysine, arginine, histidine, aspartic acid, or glutamic acid residue) or can be derivatized to be ionizable (e.g., tyrosine, serine, and cysteine residues). Accordingly, strategies to label either the N- or C-termini are provided to afford the greatest degree of sequencing ability for any given protein. Once a label is selected, a deconvolution algorithm can be modified to search for masses that correspond to any modified residues.

Characteristics of the Fragmentation Spectra

The mass spectrum (FIG. 1) is basically the number of ions (Counts) that strike a detector plate. The time at which the ions strike the detector plate determines the mass to charge (m/z) ratio of the ion striking the plate. The detector plate is calibrated with known m/z molecules. Each scanning time bin on the detector plate is then assigned an average m/z value and collects ions with m/z ratios of a defined range which is based on the particular design configuration of the instrument. Generally, the size range covered by each detector bin varies as the square root of the m/z value of the bin. This means that the absolute mass precision decreases with increasing m/z in the mass spectrometer. Noise in a mass spectrometer is always positive. Therefore, the signal is always greater than or equal to zero in each bin.

Several features of the mass spectrum of fragmented proteins can inhibit the ability to identify or properly rank the true protein sequence, depending on the relative signal strength of the labeled peptides and are deconvolved by the algorithm of the invention. Relative signal strength being defined as the labeled peptide fragment ion abundance relative to the abundance of other ions and noise in the mass spectrum. The first feature is striking the detector first may charge the detector causing a baseline shift and increasing abundance in the region above about 500 amu. This is observed as an apparent baseline shift in the mass spectrum (FIG. 1). The multiple charge states of the parent protein may also contribute to local baseline variations in the same way at m/z positions above about 1000 amu. This is more clearly observed in FIG. 1 at m/z positions above about 2000 amu.

Figure 2:
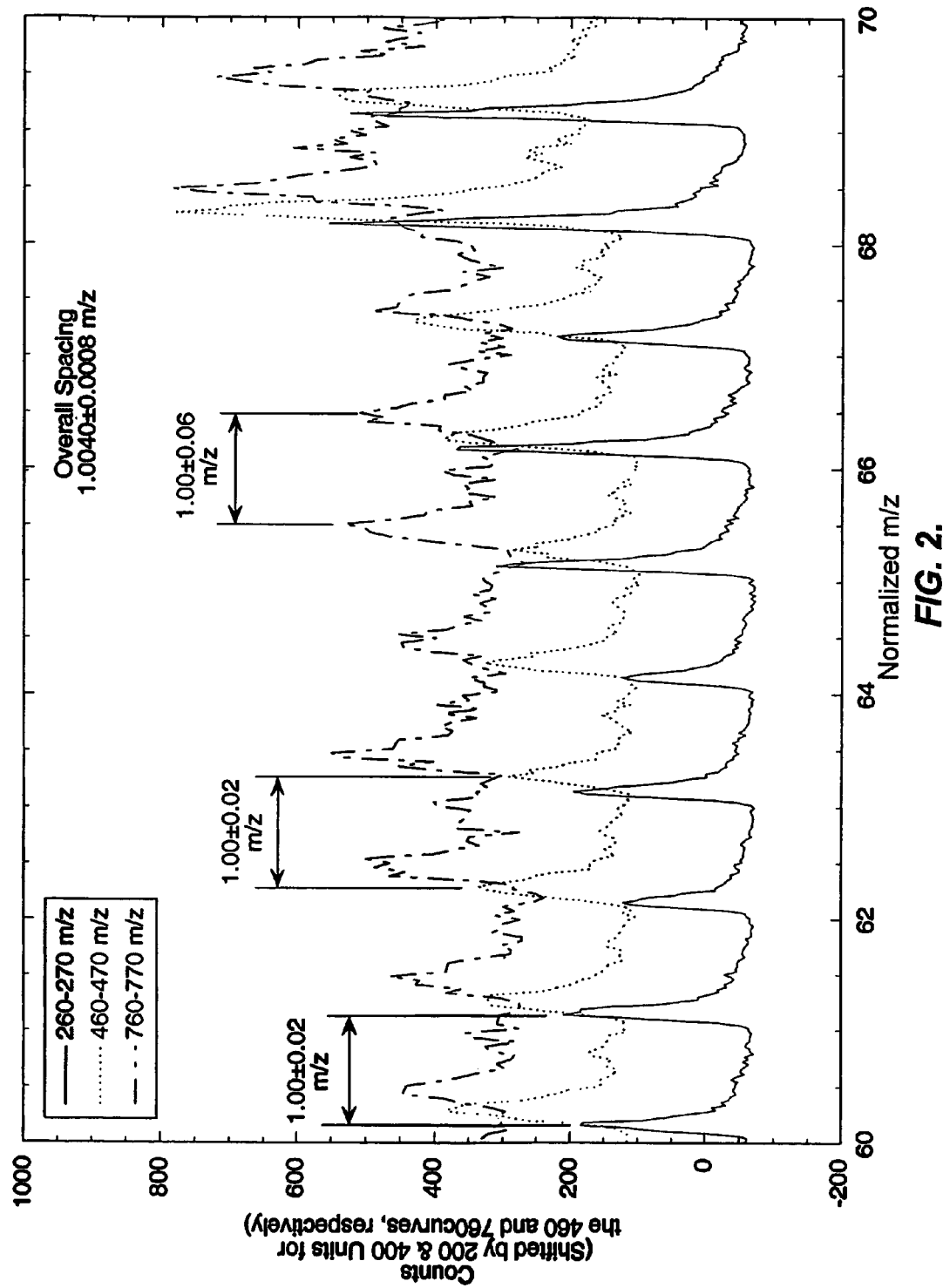
FIG. 2 shows the periodic peak pattern observed at about a 1 amu spacing over several 20 amu sections of the mass spectrum of glycogen phosphorylase (FIG. 1).

The second feature observed is (FIG. 2) that highly fragmenting conditions (e.g., high nozzle potentials for in-source fragmentation) result in an increased abundance of fragment ions at periodic mass to charge positions in the mass spectrometer. On a mass calibration scale of $^{12}C$ defined as 12.000000, these protein fragments form a characteristic pattern of peaks spaced about 1 amu apart. At highly efficient fragmentation conditions a peak appears at nearly every 1 amu spacing in the mass spectrum. The average peak to peak spacing is observed to vary slightly with the particular protein being fragmented. This is believed to be due to slight differences in the elemental composition of the protein or of the fragments represented by the peaks at each amu.

Figure 3:
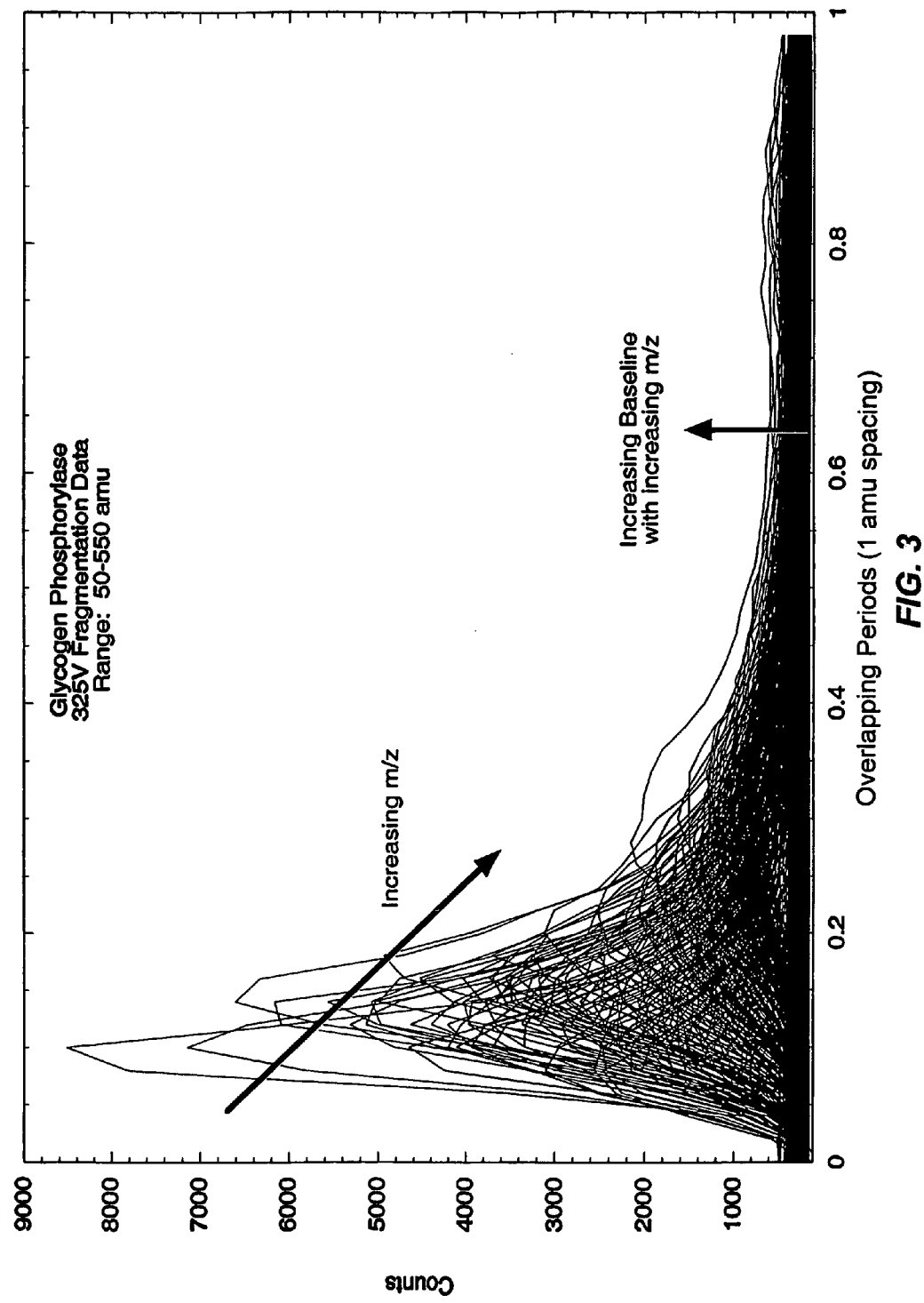
FIG. 3 shows the overlay of all the MS peaks on a 1 amu spacing for glycogen phosphorylase fragmentation data at 325V in the range of 50–550 amu.

At highly fragmenting conditions virtually all the peaks in the mass spectrum overlay this nearly 1 amu pattern (FIG. 3). It is this observation that enables the key aspects of the current invention. First, since most of the peaks overlay this pattern (or a multiple charge state analog of this pattern) it is possible to easily distinguish the signal peaks from labeled fragments that lie off this periodic spacing, such as labeled fragments wherein the label contains one or more elements with an unusual nuclear binding energy. Second, the periodicity allows for the determination of local minima and maxima in the mass spectrum, such that the spectrum can be corrected for local noise, allowing for a better determination of the actual abundance of counts at each mass-to-charge position in the mass spectrum. Third, an average or characteristic peak shape can be determined for the unwanted spectral noise at highly fragmenting conditions and this noise deconvolved or subtracted from the rest of the mass spectrum, thus reducing its contribution to the ranking algorithm and improving the confidence of the sequence determination produced by the algorithm of the invention. One of skill in the art will appreciate that other larger periodicity patterns may also be found in the data and similarly applied to assist in sequence deconvolution in addition to this major pattern shown.

Labels

As noted above, the following considerations are relevant to the selection of a labeling agent:

i) the mass of the label is preferably unique and preferably shifts the fragment masses to regions of the spectrum with low background;

ii) the label preferably contains fixed positive or negative charges to direct remote charge fragmentation at the N- or C-terminus;

iii) the label is preferably robust under the fragmentation conditions and does not undergo unfavorable fragmentation;

iv) the labeling chemistry is preferably efficient under a range of conditions, particularly denaturing conditions, thereby reproducibly and uniformly labeling the N- or C-terminus;

v) the labeled protein preferably remains soluble in the MS buffer system of choice;

vi) the label preferably increases the ionization efficiency of the oligomer, or at least does not suppress it; and vii) the label may contain a mixture of two or more isotopically distinct species to generate a unique mass spectrometric pattern at each labeled fragment position.

In view of the label selection criteria, preferred labeling moieties are those that have a detection enhancement component, an ion mass signature component and a reactive functional group, preferably one that reacts with the C- or N-terminus of a protein. The reactive group can be directly attached to either or both of the other two label components.

In one embodiment, labels are used in pairs to further increase the ability to identify the mass ladder from other peaks in the mass spectrum. The use of mixed isotope labels is particularly suited for further deconvolution of the labeled fragment peaks, since abundant isotope pairs will only exist for labeled fragments in the mass spectrum and the isotopes typically exhibit similar ionization and fragmentation efficiencies. Analogs of a label that differ by one or more methyl or methylene groups, or charge state can also be used. Even two chemically distinct molecules can be used in dual labeling situations to enhance the identification of the labeled fragment mass ladder. In one embodiment, a single sample is labeled simultaneously with dual labels and the combined mass spectrum generated. In a preferred embodiment, duplicate samples are labeled independently and mixed in roughly similar proportions prior to fragmentation on the MS. One advantage to this latter embodiment resides in minimizing the possibility of signal dilution when side residues are also labeled. In another embodiment duplicate samples are labeled with separate labels, fragmented separately on the MS, and the mass spectra added together to form a virtual dual labeled spectrum.

In still another embodiment, the reactive functional group is separated from one or both of the detection enhancement component and the ion mass signature component by a linker. The linker is preferably designed such that it is chemically stable and inert, and such that it allows efficient separation of the reactive group and at least one of the other two components of the tag. Within a preferred embodiment of the invention, the linker is composed of a hydrocarbon chain or, most preferably, of a hydrocarbon chain linked to an aryl or heteroaryl ring and preferably provides additional separation between the ionizable group and the linking group.

As will be understood by one of ordinary skill in the art, a variety of hydrocarbon chains and modified hydrocarbon chains may be utilized within the present invention. Preferred hydrocarbon chains which are attached to the phenyl ring may be found in the family of alkanes, with particularly preferred linkers ranging from 2 carbon atoms to about 20 carbon atoms in length. Within a preferred embodiment of the invention, the linker is a phenethyl, aliphatic amide, or secondary amine group.

Detection Enhancement Components

A detection enhancement component, as used herein, refers to a portion of the labeling moiety that facilitates detection of the protein fragments in the mass spectrometer. Accordingly, the detection enhancement component can provide a positively charged ionic species under fragmentation conditions in a mass spectrometer ionization chamber, or the component can provide a negatively charged ionic species under fragmentation conditions in a mass spectrometer ionization chamber. For many of the detection enhancement components, the amount of ionized species present will depend on the medium used to solubilize the protein. Preferred detection enhancement components (i.e., species that can generate a positive or negative charge) can be classified into three categories: 1) components that carry "hard" charge, 2) components that carry "soft" charge, and 3) components that provide no charge but are in close proximity to protein residues that carry "soft" charge.

Components that carry "hard" charge are arrangements of atoms that are substantially ionized under all conditions, regardless of medium pH. "Hard" positively-charged detection enhancement components include, but are not limited to, tetraalkyl or tetraaryl ammonium groups, tetraalkyl or tetraaryl phosphonium groups, and N-alkylated or N-acylated heterocyclyl and heteroaryl (e.g., pyridinium) groups. "Hard" negatively-charged detection components include, but are not limited to, tetraalkyl or tetraacyl borate groups.

Components that carry "soft" charge are arrangements of atoms that are ionized at a pH above or below their pKa, respectively (i.e., bases and acids). Within the context of the current invention, "soft" positive charges include those bases with a pKa of greater than 8, preferably greater than 10, and most preferably greater than 12. Within the context of the current invention, "soft" negative charges include those acids with a pKa of less than 4.5, and preferably less than 2, and most preferably less than 1. At the extremes of pKa, the "soft" charges approach classification as "hard" charges. "Soft" positively-charged detection enhancement components include, but are not limited to, 1°, 2°, and 3° alkyl or aryl ammonium groups, substituted and unsubstituted heterocyclyl and heteroaryl (e.g., pyridinium) groups, alkyl or aryl Schiff base or imine groups, and guanidino groups. "Soft" negatively-charged detection enhancement components include, but are not limited to, alkyl or aryl carboxylate groups, alkyl or aryl sulfonate groups, and alkyl or aryl phosphonate or phosphate groups.

For both "hard" and "soft" charged groups, as will be understood by one of ordinary skill in the art, the groups will be accompanied by counterions of opposite charge. For example, within various embodiments, the counterions for positively-charged groups include oxyanions of lower alkyl organic acids (e.g., acetate), halogenated organic acids (e.g., trifluoroacetate), and organosulfonates (e.g., N-morpholinoethane sulfonate). The counterions for negatively-charged groups include, for example, ammonium cations, alkyl or aryl ammonium cations, and alkyl or aryl sulfonium cations.

Components that are neutral but are in close proximity to protein residues that carry "soft" charge (e.g. lysine, histidine, arginine, glutamic acid, or aspartic acid) can be used as detection enhancement components. In this case, the label carries no ionized or ionizable groups, and the detection enhancement is provided by a nearby protein residue that carries charge. Within the context of the present invention, close proximity is defined as within about 4 residues from the labeled terminus of the protein, and more preferably within about 2 residues of the labeled terminus of the protein.

The detection enhancement component of the label can also be multiply charged or capable of becoming multiply charged. For example, a label with multiple negative charges can incorporate one or singly charged species (e.g. carboxylate) or it can incorporate one or more multiply charged species (e.g., phosphate). In a representative example of this embodiment of the invention a species bearing multiple carboxylates, such as, for example a polyaminocarboxylate chelating agent (e.g., EDTP, DTPA) is attached to the protein. Methods of attaching polyaminocarboxylates to proteins and other species are well known in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370–387; Kasina et al., *Bioconjugate Chem.*, 9: 108–117 (1998); Song et al., *Bioconjugate Chem.*, 8: 249–255 (1997).

In a similar manner, labels having multiple positive charges can be purchased or prepared using methods accessible to those of skill in the art. For example, a labeling moiety bearing two positive charges can be rapidly and easily prepared from a diamine (e.g., ethylenediamine). In a representative synthetic route, the diamine is monoprotected using methods known in the art and the non-protected amine moiety is subsequently dialkylated with a species bearing one or more positive charges (e.g., (2-bromoethyl)trimethylammonium bromide) (Aldrich)). Deprotection using art-recognized methods provides a reactive labeling species bearing at least two positive charges. Many such simple synthetic routes to multiply charged labeling species will be apparent to one of skill in the art.

Ion Mass Signature Component

The ion mass signature component is the portion of the labeling moiety which preferably exhibits a unique ion mass signature in mass spectrometric analyses. The ion mass signature component includes moieties that do not efficiently ionize under conditions in which proteins ionize (e.g., aromatic carbon compounds) as well as molecules that readily ionize under protein ionizing conditions to generate multiply charged ionic species. Both types of chemical entities can be used to shift the ion/mass signature of the amino acids and peptides attached to the label (after fragmentation of the labeled protein) in the mass spectrum. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

Figure 4:
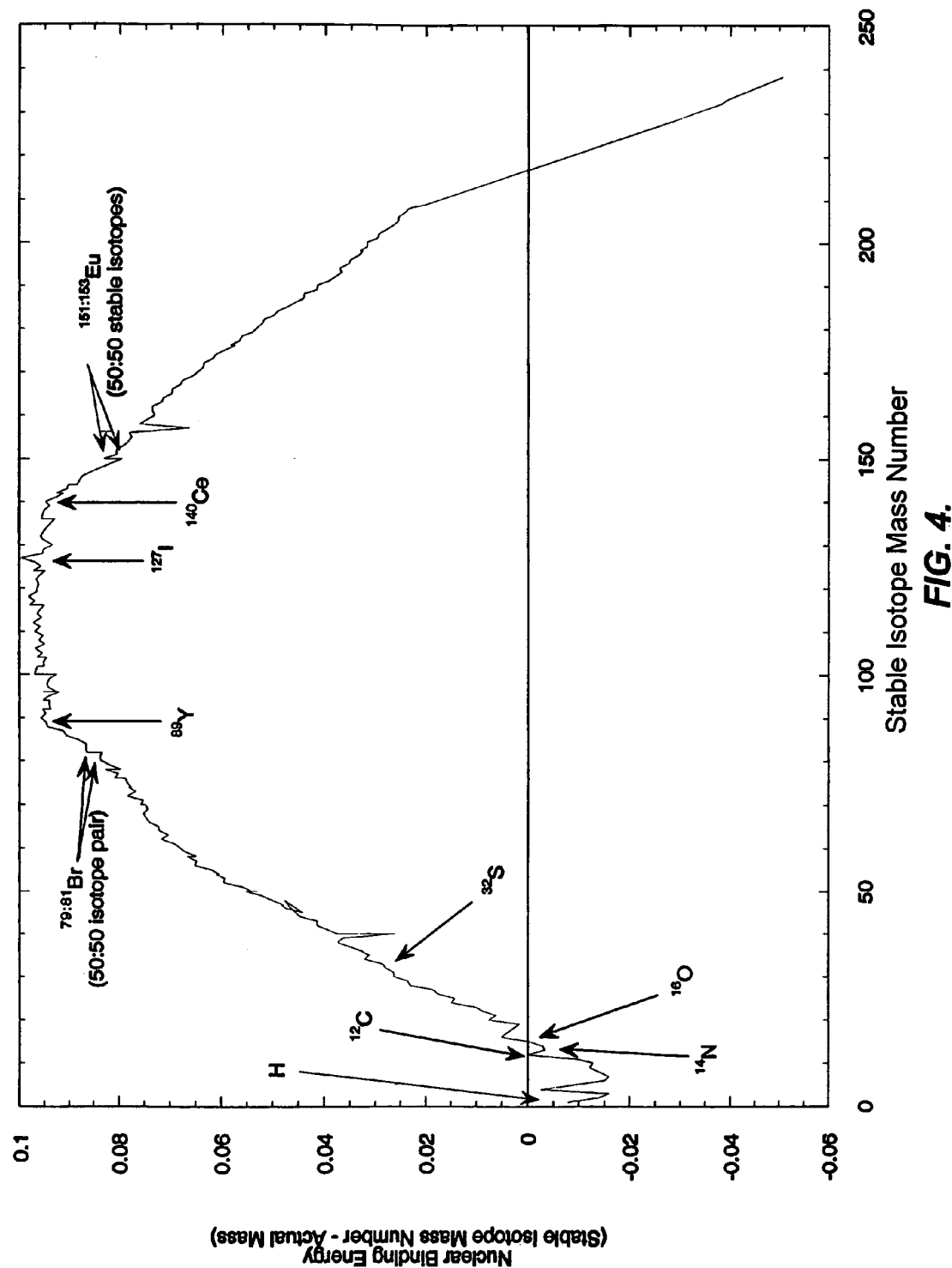
FIG. 4 illustrates the nuclear binding energy for the elements of the periodic table as a function of isotope mass number.

In a most preferred embodiment, the ion mass signature component is any element that exhibits a nuclear binding energy different from the major constituents of proteins. The major constituents of proteins are: C, H, N, O, and S. Defining nuclear binding energies in terms of the $^{12}C=12.000000$ mass standard (FIG. 4), preferred elements with unique ion mass signatures are those elements in the periodic table with atomic numbers between 17 (Cl) and 77 (Ir). Particularly preferred elements for use as ion mass signature components of the label include elements with atomic numbers between 35 (Br) and 63 (Eu). The most preferred elements for use as ion mass signature components are those with atomic numbers between 39 (Y) and 58 (Ce). Br and Eu are also particularly preferred components of the label as each of these elements exhibit two stable isotopes of roughly equal proportions and nuclear binding energies that differ significantly from the periodic peak pattern observed for proteins fragmented in the mass spectrometer. The elements I and Y are also particularly preferred ion mass signature components as they exhibit the greatest difference in nuclear binding energy from the periodic protein fragment peak in the mass spectrum and because they are readily incorporated into labels. Transition metals are within the preferred and most preferred lists of unique ion mass signature elements and can often be incorporated into labels as chelates, similar to the known Y (Lewis, et al., *Bioconjugate Chemistry* 5:565–576 (1994)) and Eu (Zarling, et al., U.S. Pat. No. 5,891,656) chelates.

In another embodiment, a unique ion mass signature component may be created by using a multiply charged label. Such a multiply charged label can incorporate an element with a different nuclear binding energy or can consist solely of elements similar in nuclear binding energies to that of the major protein constituents. Such charge states may be formed with "hard" or "soft" or a combination of "hard" and "soft" charges incorporated into the label. Multiple "hard" charge states between 2 and 4 are preferred. A multiple "hard" charge state of 3 is most preferred when the label consists solely of elements with nuclear binding energies similar to C, H, N, O, and S. A multiple "hard" charge state of 2 is most preferred when the label contains at least one element exhibiting a nuclear binding energy different from C, H, N, O, and S.

As will be understood by one of skill in the art, spurious mass spectral peaks can arise not only from the fragmentation of unlabeled amino acids and peptides but also from impurities in the sample and/or matrix. In order to further increase the uniqueness of the ion mass signature of the label and to be able to identify desired labeled fragment peaks from "noise," it is preferable to shift the labeled fragments to regions of less spectral noise by optimizing the mass of the label. For example, it is preferred that the label mass generate an ion greater than 100 amu and less than 700 amu. The upper limit on the mass of the label, being determined by the mass resolution of the mass spectrometer used. This may be done by increasing the molecular weight of a low molecular weight label or by increasing the number of charges on a high molecular weight label.

An alternative method for providing a more unique mass signature to a labeling moiety is to incorporate stable isotopes in the label (see, for example, Gygi et al., *Nature Biotechnol.* 17: 994–999 (1999)). For example, by incorporating eight deuterium atoms into a labeling moiety and labeling the protein with a 50:50 mixture of the deuterated and nondeuterated label, the resulting singly-charged fragments that include the label are easily identified as equally intense doublets; one at the mass corresponding to the species with the nondeuterated label and the other at the mass corresponding to the species with the deuterated label with a spacing of 8 amu. In a preferred embodiment, the mass difference is more than about 1 amu at the single charge state. In the most preferred embodiment the mass difference is from about 4 to about 10 amu at the single charge state. The incorporation of multiple isotopes of elements that exhibit nuclear binding energies significantly different from C, H, N, O, and S is preferred. Br and Eu elements are most preferred because the exhibit two natural isotopic abundances of about 50:50.

Another method for providing a more unique mass signature to a labeling moiety is to incorporate a mixture of alkyl and/or aryl substitutions onto the label, such that the corresponding set of fragment peaks is easily recognizable in the mass spectrum. For example, the protein can be labeled with a mixture of a label that contains a trimethyl ammonium group and the same label that contains a dimethylethylammonium group in place of the trimethyl ammonium group. This labeling moiety produces two fragment ion peaks for each amino acid in the sequence that differ by 14 amu from each other. It will be apparent to those skilled in the art that many such combinations can be derived.

Reactive Groups

A third component of the labeling moiety is a functional group which is reactive with the N-terminus amino group, the C-terminus amino group or another constituent of the N- or C-terminus amino acid.

The reactive functional group can be located at any position on the tag. For example, the reactive group can be located on an aryl nucleus or on a chain, such as an alkyl chain, attached to an aryl nucleus. When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions are those which proceed under relatively mild conditions in an aqueous or mixed aqueous/organic solvent milieu.

Particularly preferred chemistries that target the primary amino groups in proteins (including the N-terminus) include, for example: aryl fluorides (see, Sanger, F., *Biochem. J.*, 39:507 (1945); Creighton, T. E., *Proteins: Structures and Molecular Principles* (W.H. Freeman, NY, 1984); Niederwieser, A., in: *Methods in Enzymology*, 25:60–99 (1972); and Hirs, C. H. W., et al., *Arch. Biochem. Biophys.*, 111:209–222 (1965), sulfonyl chlorides (Gray, W. R., in: *Methods in Enzymology*, 25:121–137 (1972)), cyanates (Stark, G. R., in: *Methods in Enzymology*, 25:103–120 (1972)), isothiocyanates (Niall, H. D., in: *Methods in Enzymology*, 27:942–1011 (1973)), imidoesters (Galella, G., et al., *Can. J. Biochem.*, 60:71–80 (1982)), N-hydroxysuccinimidyl esters (Lomant, A. J., et al., *J. Mol. Biol.*, 104: 243–261 (1976)), O-acylisoureas (Lomant, A. J., et al., *J. Mol. Biol.*, 104:243–261 (1976)), chlorocarbonates and carbonylazides (Solomons, T. W. G, Organic Chemistry (John Wiley & Sons, NY, 1976), aldehydes (Novotny et al., *Anal. Chem.*, 63:408 (1991) and Novotny et al., *J. Chromatography*, 499:579 (1990)), and alkylhalides and activated alkenes (Wagner, D. S., et al., *Biol Mass Spectrometry*, 20:419–425 (1991)). Preferred examples of chemical constituents that react with the carboxyl groups of proteins are benzyl halides (Solomons, T. W. G, Organic Chemistry (John Wiley & Sons, NY, 1976); Merrifield, B., *Science*, 232:341–347 (1986); and Horton, H. R., et al., *Methods in Enzymology*, 25:468 (1972)) and carbodiimide (Yamada, H., et al., *Biochem.*, 20:4836–4842)), particularly if stabilized using N-hydroxysuccinimide (see, Grabarek, Z., et al., *Anal. Biochem.* 185:131–135 (1990). Both of these carboxyl labeling approaches are expected to label carboxyl containing amino acid residues (e.g., aspartate and glutamate) along with that of the C-terminus. These and other useful reactions are discussed in, for example, March, ADVANCED ORGANIC CHEMISTRY, 3$^{rd}$ Ed., John Wiley & Sons, New York, 1985; Hermanson, BIOCONJUGATE TECHNIQUES, Academic Press, San Diego, 1996; and Feeney et al., MODIFICATION OF PROTEINS;

Advances in Chemistry Series, Vol. 198, American Chemical Society, Washington, D.C., 1982.

The reactive functional groups can be chosen such that they do not participate in, or interfere with, the reactions necessary to assemble the tag. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Figure 5:
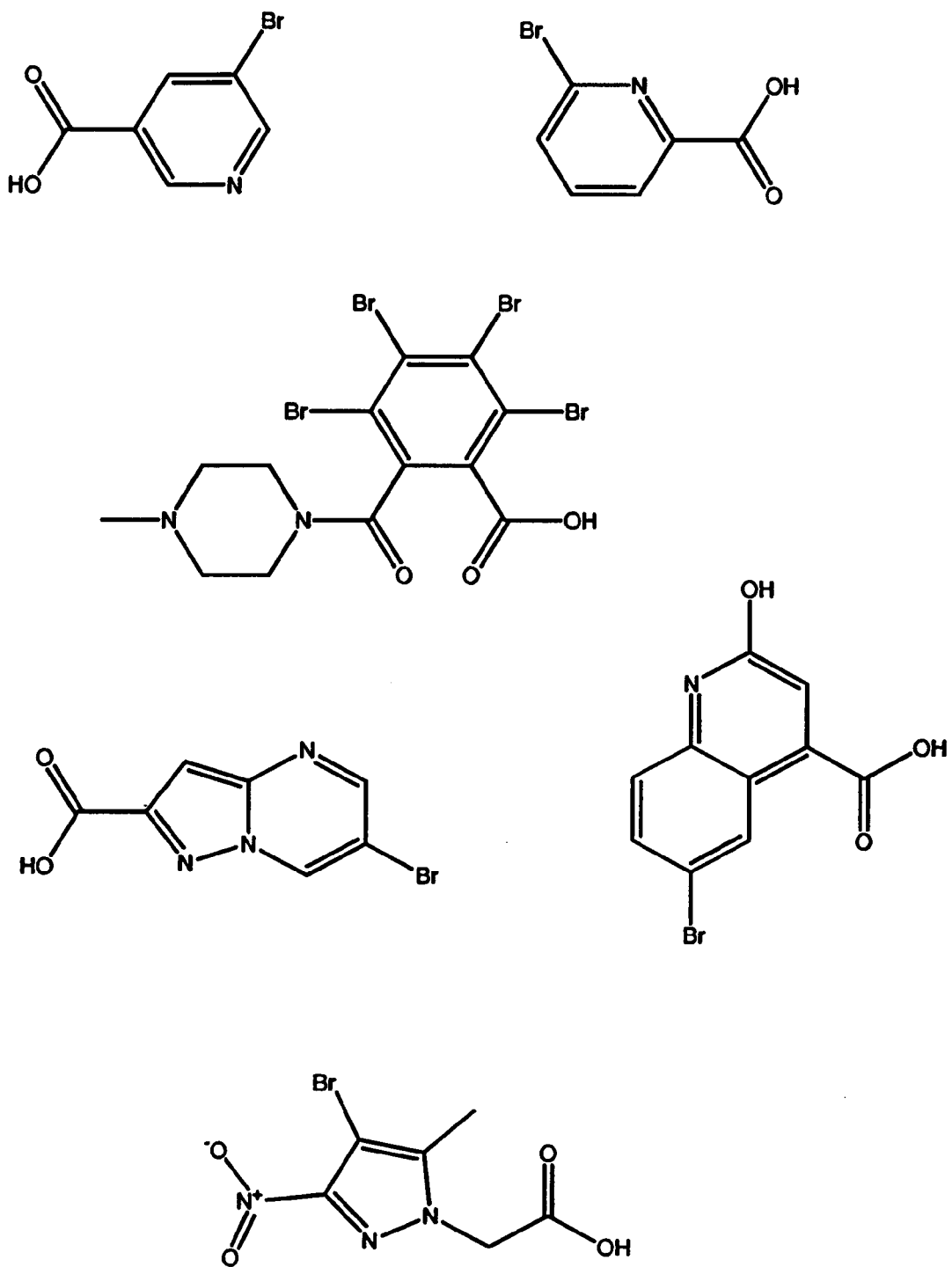
FIG. 5 illustrates the structures of a number of labeling moieties having at least one bromine substituent.
Figure 6:
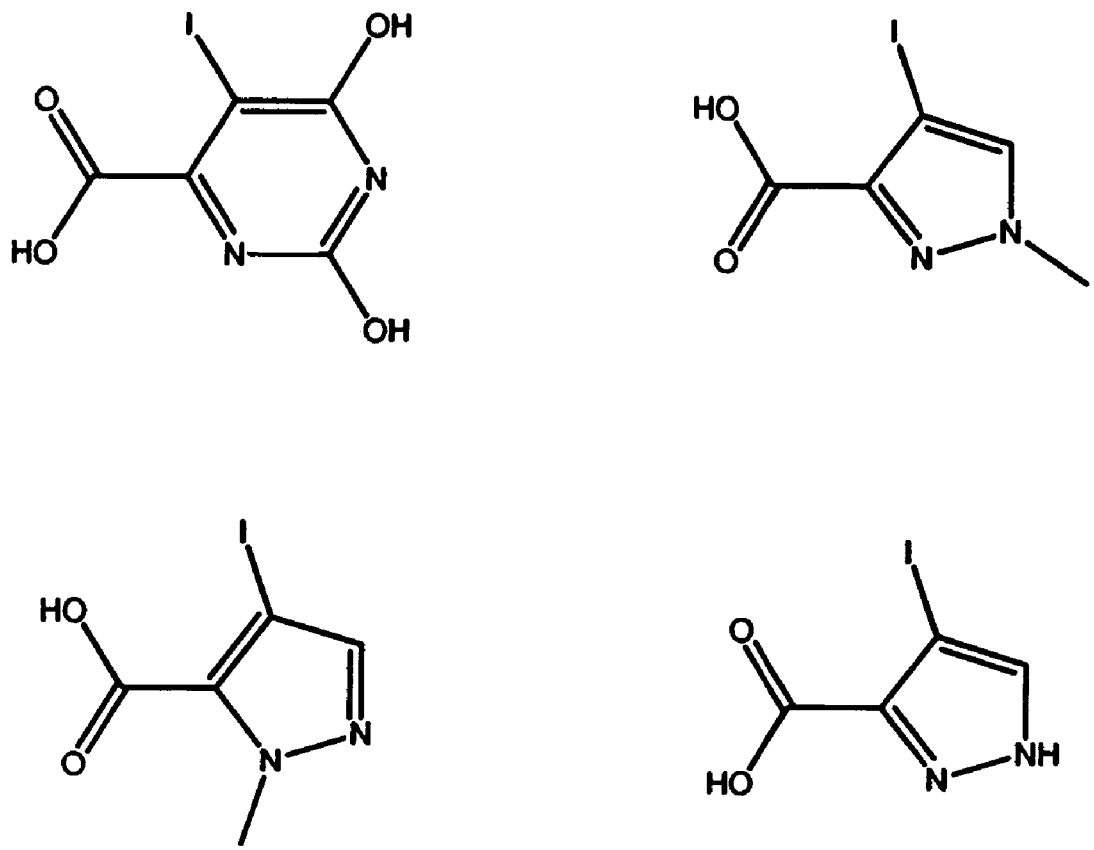
FIG. 6 illustrates the structures of a number of labeling moieties having at least one iodine substituent.

FIGS. 5 and 6 provide the structures of a variety of labeling moieties having one or more bromine (FIG. 5) or iodine (FIG. 6) atoms. Suitable labels include 5-bromonicotinic acid, 6-bromo-2-hydroxy-quinoline-4-carboxylic acid (BHQC), 6-bromopicolinic acid, 4-bromobenzaldehyde, as well as other commercially available bromine substituted aryl carboxylic acids. Still other labels can be suitably prepared via bromination or iodination of an aryl carboxylic acid or a protected form thereof. Methods for bromination and iodination of aromatic compounds are well known to those of skill in the art and references for their preparation can be found in general texts such as March, ADVANCED ORGANIC CHEMISTRY, 4$^{th}$ Ed., John Wiley & Sons. One of skill in the art will further appreciate that the carboxylic acid residues are typically activated (e.g., as a NHS ester) prior to contacting a protein. Additionally, examination of the labeling residues indicates that the majority have an ionizable nitrogen atom (present as an ammonium group at pH below the p$K_a$ of the ammonium ion.

Table 1 provides a non-limiting description of labeling moieties useful in the labels of the present.

TABLE 1

Generic Mass Defect Label
A moieties carry charge (positive or negative) for MS ionization.
B moieties are mass defect elements.
C moieties are reactive groups for linkage to biomolecules.
A, B, and C moieties are located on a variety of aromatic/aliphatic frameworks.

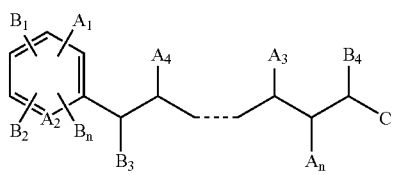

1A. Exemplary $A_n$ Moieties:

----NRR'    R,R' = H, alkyl, aromatic

R = H, alkyl, aromatic, OH, OR', NO$_2$, Cl, F ...
X = N or other basic heterocycle TABLE 1-continued $\overset{N-R'}{\underset{R}{\diagup\!\!\diagdown}}$    R,R' = H, alkyl, aromatic $----\overset{O}{\underset{O}{\overset{\|}{S}}}-OH,\quad ----O\overset{O}{\underset{O}{\overset{\|}{S}}}-OH$ $\overset{NR'''}{\underset{R}{\diagup\!\!\diagdown}}-NR'R''$    R,R',R'',R''' = H, alkyl, aromatic $----\overset{O}{\underset{OH}{\overset{\|}{P}}}-OH,\quad ----O\overset{O}{\underset{OH}{\overset{\|}{P}}}-OH$ ----PRR'    R,R' = H, alkyl, aromatic ----NRR'R''$^{\oplus}$    R,R',R'' = alkyl, aromatic (pyridinium ring)—R'    R = H, alkyl, aromatic, OH, OR'', NO$_2$, Cl, F ...
R' = alkyl, aromatic
X = N—, S—, O— containing heterocycle ----BRR'R''$^{\ominus}$    R,R',R'' = alkyl, aromatic ----SRR'$^{\oplus}$    R,R' = alkyl, aromatic (phenyl ring)—OH    R = H, alkyl, aromatic, NO$_2$, Cl, F ...

----ORR'$^{\oplus}$    R,R' = alkyl, aromatic

1B. Exemplary $B_n$ Moieties:

(pyridinium-like ring with X, Z, R)
(Z = Br, I)
(R = H, alkyl, aromatic, OH, OR', $_2$, Cl, F ...)
(X = C, N, S, ----CH=CH—Z,  ----CZ$_3$   (Z = Br, I)

(metal chelate structure)
metal chelates
(M = Y, La, Ce, Eu ... ; -5)
(X = N, O, S)
(R, R', R'', R''' = alkyl, aromatic)
(Note: The chelating framework can be any size geometry with any number of coordinating atoms TABLE 1-continued 1C. Exemplary C Moieties:

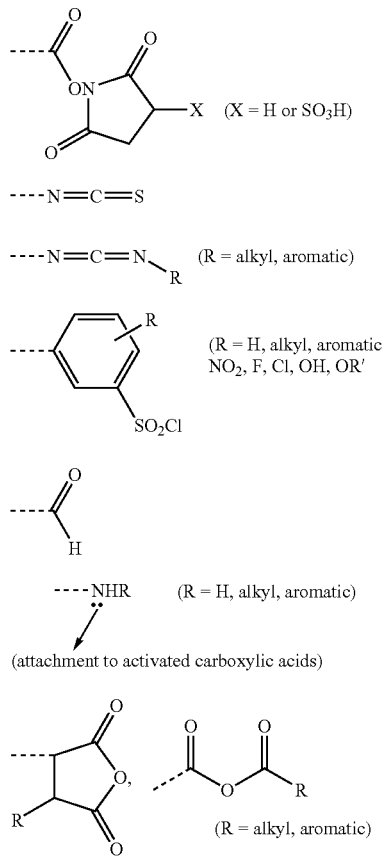

(attachment to activated carboxylic acids)

Synthesis

Once the reactive group, linker, and ionizable groups or ion mass signature components have been selected, the final compound is synthesized utilizing standard organic chemistry reactions. A preferred compound for use within the present invention is the NHS ester of 5-bromo-3-pyridylacetic acid (5-Br-3-PAA) or an analogous agent.

With the selection of a suitable labeling moiety, conditions for attaching the label to the protein should ensure that the N- or C-terminus of the protein is uniformly labeled and that the labeled protein remains soluble in appropriate MS buffer systems. Typically, labeling will be carried out under denaturing conditions (e.g., surfactants or 8M urea). Surfactants and urea both suppress MS ionization and methods that provide rapid clean up and transfer of the labeled protein sample to a suitable MS buffer should also be employed.

Detectable Moieties

In another preferred embodiment, the protein is labeled with a moiety that enhances its detectability in, for example, protein purification and separation processes (e.g., electrophoresis). The detectable moiety can be detected by, for example, spectroscopy (e.g., UV/Vis, fluorescence, electron spin resonance (ESR), nuclear magnetic resonance (NMR) and the like), detection of radioactive isotopes, etc. When the protein is detected by UV/Vis, it is generally desirable to attach a chromophoric label to the protein (e.g., phenyl, napthyl, etc.). Similarly, for detection by fluorescence spectroscopy, a fluorophore is preferably attached to the protein. For example, Quantum Dye™ is a fluorescent Eu chelate and 5-carboxy-2',4',5',7'-tetrabromosulfonefluorescein succinimidyl ester is an N-terminal reactive, bromine-containing fluorophore (commercially available from Research Organics, catalog #0723Q and Molecular Probes, catalog #C-6166, respectively). For ESR, the detectable moiety can be a free radical, such as a moiety including a nitroxide group. When the protein is detected by an NMR method, the detectable moiety can be enriched with an NMR accessible nuclei, such as fluorine, $^{13}C$, and the like.

In a presently preferred embodiment, the detectable moiety is a fluorophore. Many reactive fluorescent labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and PE-Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

There is a great deal of practical guidance available in the literature for selecting an appropriate fluorophore for a particular tag, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, $2^{nd}$ Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In addition to fluorophores that are attached directly to a protein, the fluorophores can also be attached by indirect means. In an exemplary embodiment, a ligand molecule (e.g., biotin) is preferably covalently bound to the protein. The ligand then binds to another molecule (e.g., streptavidin), which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Useful fluorescent detectable moieties can be made to fluoresce by exciting them in any manner known in the art, including, for example, with light or electrochemical energy (see, for example, Kulmala et al, *Analytica Chimica Acta* 386: 1 (1999)). Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

The fewer the processing steps between any separation technique and MS sequencing method, the faster that proteins can be identified, and the lower the cost of proteomic research. Typical electrophoresis buffers (e.g., Hochstrasser et al. *Anal Biochem.*, 173:424 (1988). and O'Farrel, *J. Biol. Chem.*, 250:4007 (1975)) contain components (e.g., tris (hydroxymethyl)aminomethane buffers and sodium dodecyl sulfate, that supress the ionization of proteins in the mass spectrometer. These components may be replaced with other more volatile components (e.g., morpholinoalkylsulfonate buffers and ephemeral surfactants) that do not suppress ionization in the MS. In another embodiment, the samples are diluted with ammonium bicarbonate or ammonium acetate buffer to provide a volatile proton source for the mass spectrometer. Wilm, M. et al., *Anal. Chem.*, 68:1–8 (1996). In another embodiment, a buffer exchange is conducted through by chromatographic or tangential flow dialysis as the sample is transported from the outlet of the separation process to the inlet of the MS.

Labeling Procedure

In some instances, salts (e.g., TRIS and SDS) and urea present in electrophoresis buffers can suppress ionization of the labeled proteins and can generate small mass/charge ions that potentially confuse sequence analysis. Accordingly, spin dialysis procedures can be employed to rapidly exchange buffer systems prior to MS analysis. Alternatively, desalting columns (e.g., the ZipTip™ tip sold by Millipore) can be used for sample clean up and buffer exchange. Desalted samples can be resuspended in 0.1M ammonium bicarbonate as described by Wilm and Mann (see, Wilm, et al., ibid.) with minimal addition of methanol, or in 0.01M ammonium acetate buffer (with 0.1% formic acid) with minimal addition of acetonitrile as described by Mark (see "Protein structure and identification with MS/MS," paper presented at the PE/Sciex Seminar Series, Protein Characterization and Proteomics: Automated high throughput technologies for drug discovery, Foster City, Calif. (March, 1998)).

The coupling rates of the compound may be tested to ensure that the compound is suitable for sequencing polypeptides. In general, the faster the coupling rate the more preferred the compound. Coupling rates of between 2 and 10 minutes at 50° C. to 70° C. are particularly preferred. Similarly, fast reaction rates are also preferred, because exposure to the reaction mixture over an extended period of time might hydrolyze the peptide bonds, or lead to inefficient and irreproducible side reactions with the polypeptide residues, which could complicate mass spectral deconvolution.

In another preferred embodiment, one or more of the components of a protein mixture is reversibly attached to a solid support prior to the label being attached to a polypeptide. Various materials may be used as solid supports, including, for example, numerous resins, membranes or papers. These supports may additionally be derivatized to incorporate a cleavable functionality. A number of cleavable groups that may be used for this purpose include disulfides (—S—S—), glycol (—CH[OH]—CH[OH]—), azo (—N=N—), sulfone (—$SO_2$—), and ester (—COO—) linkages (see, Tae, *Methods in Enzymology*, 91:580 (1983)). Supports which are particularly preferred include membranes such as Sequelon™ (Milligen/Biosearch, Burlington, Mass.). Representative materials for the construction of these supports include, among others, polystyrene, porous glass, polyvinylidinefluoride and polyacrylamide. In particular, polystyrene supports include, among others: (1) a (2-aminoethyl) aminomethyl polystyrene (see, Laursen, *J. Am. Chem. Soc.* 88: 5344 (1966)); (2) a polystyrene similar to number (1) with an aryl amino group (see, Laursen, *Eur. J. Biochem.* 20: 89 (1971)); (3) amino polystyrene (see, Laursen et al., *FEBS Lett.* 21: 67 (1972)); and (4) triethylenetetramine polystyrene (see, Horn et al., *FEBS Lett.* 36:285 (1973)). Porous glass supports include: (1) 3-aminopropyl glass (see, Wachter et al., *FEBS Lett.* 35: 97 (1973)); and (2) N-(2-aminoethyl)-3-aminopropyl glass (see, Bridgen, *FEBS Lett.* 50: 159 (1975)). Reaction of these derivatized porous glass supports with p-phenylene diisothiocyanate leads to activated isothiocyanato glasses (see, Wachter et al., supra). Polyacrylamide-based supports are also useful, including a cross-linked β-alanylhexamethylenediamine polydimethylacrylamide (see, Atherton et al., *FEBS Lett.* 64: 173 (1976)), and an N-aminoethyl polyacrylamide (see, Cavadore et al., *FEBS Lett.* 66: 155 (1976)).

One of ordinary skill in the art will readily utilize appropriate chemistry to couple the polypeptide to the solid supports described above (see, generally Machleidt and Wachter, Methods in Enzymology: [29] New Supports in Solid-Phase Sequencing 263–277 (1974). Preferred supports and coupling methods include the use of aminophenyl glass fiber paper with EDC coupling (see, Aebersold et al., *Anal. Biochem.* 187: 56–65 (1990)); DITC glass filters (see, Aebersold et al., *Biochem.* 27: 6860–6867 (1988) and the membrane polyvinylidinefluoride (PVDF) (Immobilon P™, Milligen/Biosearch, Burlington, Mass.), along with SequeNet™ chemistry (see, Pappin et al., Current Research in Protein Chemistry, Villafranca J. (ed.), pp. 191–202, Academic Press, San Diego, 1990)).

In the practice of the present invention, attachment of the polypeptide to the solid support may occur by either covalent or non-covalent interaction between the polypeptide and solid support. For non-covalent attachment of the polypeptide to the solid support, the solid support is chosen such that the polypeptide attaches to the solid support by non-covalent interactions. For example, a glass fiber solid support may be coated with polybrene, a polymeric quaternary ammonium salt (see, Tarr et al., *Anal. Biochem.*, 84:622 (1978)), to provide a solid support surface which will non-covalently attach the polypeptide. Other suitable adsorptive solid phases are commercially available. For example, polypeptides in solution may be immobilized on synthetic polymers such as polyvinylidine difluoride (PVDF, Immobilon, Millipore Corp., Bedford, Mass.) or PVDF coated with a cationic surface (Immobilon CD, Millipore Corp., Bedford, Mass.). These supports may be used with or without polybrene. Alternatively, polypeptide samples can be prepared for sequencing by extraction of the polypeptide directly from polyacrylamide by a process called electroblotting. The electroblotting process eliminates the isolation of polypeptide from other peptides which may be present in solution. Suitable electroblotting membranes include. Immobilon and Immobilon CD (Millipore Corp., Bedford, Mass.).

More recently, automated methods have been developed that allow chemistries to be performed on polypeptides immobilized on solid supports by non-covalent, hydrophobic interaction. In this approach, the samples in aqueous buffers, which may contain salts and denaturants, are pressure-loaded onto columns containing a solid support. The bound polypeptide is then pressure-rinsed to remove interfering components, leaving the bound polypeptide ready for labeling (see, Hewlett-Packard Product Brochure 23-5091-5168E (November, 1992) and Horn, U.S. Pat. No. 5,918,273 (Jun. 29, 1999).

The bound polypeptide is reacted under conditions and for a time sufficient for coupling to occur between the terminal amino acids of the polypeptide and the labeling moiety. The physical properties of the support may be selected to optimize the reaction conditions for a specific labeling moiety. Preferably, coupling with the amino groups of the polypeptide occurs under basic conditions, for example, in the presence of an organic base such as trimethylamine, or N-ethylmorpholine. In a preferred embodiment, the label is allowed to react with the bound peptide in the presence of 5% N-ethylmorpholine in methanol:water (75:25 v/v). Because of the mode of attachment, excess of reagent, coupling base and reaction by-products can be removed by very polar washing solvents prior to removal and sequencing of the labeled polypeptide by mass spectrometry. Various reagents are suitable as washing solvents, including, for example, methanol, water, mixtures of methanol and water, or acetone.

When the labeling reaction is conducted entirely in solution phase, the reaction mixture is preferably submitted to a purification cycle, such as dialysis, gel permeation chromatography, and the like.

Sequencing a Portion of a Protein

In another aspect, the present invention provides a method for sequencing a portion of a protein in a protein mixture, the method comprising:

(a) contacting the protein mixture with a C-terminus or N-terminus labeling moiety to covalently attach a label to the C- or N-terminus of the protein and form a labeled protein mixture, the C-terminus or N-terminus labeling moiety comprising at least one element having an atomic number from 17 to 77, more preferably from 35 to 63, with the proviso that said element is other than sulfur;

(b) separating individual labeled proteins in said protein mixture; and (c) analyzing the labeled proteins from step (b) by a mass spectrometric method to determine the sequence of at least two C-terminus or two N-terminus residues.

In one group of embodiments, the method further comprises:

(d) identifying the protein by using the sequence of at least two C-terminus or two N-terminus residues in combination with a separation coordinate of the labeled protein and the protein terminus location of the sequence to search predicted protein sequences from a database of gene sequence data.

Preferred embodiments are those that have been described above for other aspects of the invention.

Separation

In a preferred embodiment, the tagging procedure is performed on a mixture of proteins. Following the tagging procedure the mixture of proteins is submitted to a separation process, which preferably, allows the separation of the protein mixture into discrete fractions. Each fraction is preferably substantially enriched in only one labeled protein of the protein mixture.

The methods of the present invention are utilized in order to determine the sequence of a polypeptide. Within preferred embodiments of the invention, the labeled polypeptide is "substantially pure," which means that the polypeptide is about 80% homogeneous, and preferably about 99% or greater homogeneous. Many methods well known to those of ordinary skill in the art may be utilized to purify the polypeptide prior to determining its amino acid sequence. Representative examples include HPLC, Reverse Phase-High Pressure Liquid Chromatography (RP-HPLC), gel electrophoresis, chromatography, or any of a number of peptide purification methods (see, generally the series of volumes entitled METHODS IN PROTEIN SEQUENCE ANALYSIS).

Even more preferred is the use of capillary electrophoresis and particularly, multi-dimensional capillary electrophoresis, such as that described in the commonly assigned copending U.S. patent application Ser. No. 09/513,486, titled "Protein Separation via Multidimensional Electrophoresis," and filed on Feb. 25, 2000.

Although substantially pure labeled polypeptides are preferably utilized within the methods described herein, it is also possible to determine the sequence of polypeptide mixtures containing the same label. Briefly, in one embodiment, an algorithm is utilized in order to determine all of the hypothetical sequences with a calculated mass equal to the observed mass of one of the peptides in the mixture. See, Johnson et al., *Protein Science* 1:1083–1091 (1992). These sequences are then assigned figures of merit according to how well each of them accounts for the fragment ions in the tandem mass spectrum of the peptide utilizing such algorithms, the sequence of polypeptides within the mixture may be readily determined. Mixtures of oligomers analyzed simultaneously are preferentially labeled with labels incorporating different numbers of mass defect elements.

As described above, the methods herein are particularly useful for identifying proteins from a healthy or diseased tissue sample. In one group of embodiments, the methods are applied to both a mixture of proteins from a healthy tissue sample and a mixture of proteins from a diseased tissue sample. Accordingly, the protein mixtures used in this aspect of the invention can be obtained from essentially any source. Methods of isolating proteins from tissue samples are well known.

Within the present invention, the polypeptide with a derivatized terminal amino acid is sequenced by a mass spectrometer. Various mass spectrometers may be used within the present invention. Representative examples include, triple quadrupole mass spectrometers, magnetic sector instruments (magnetic tandem mass spectrometer, JEOL, Peabody, Mass.); ion-spray mass spectrometers, Bruins et al., *Anal. Chem.* 59: 2642–2647 (1987); electrospray mass spectrometers, Fenn et al., *Science* 246: 64–71 (1989); laser desorption time-of-flight mass spectrometers, Karas et al., *Anal. Chem.* 60: 2299–2301 (1988), and a Fourier Transform Ion Cyclotron Resonance Mass Spectrometer (Extrel Corp., Pittsburgh, Mass.). Within a preferred embodiment, an electrospray mass spectrometer (Mariner™ model, PE Biosystems, Foster City, Calif.) is utilized to fragment the derivatized terminal polypeptide, and a time-of-flight detector with better than 50 ppm mass accuracy is used to determine the sequence from the masses of the labeled fragments.

One of skill in the art will appreciate that the sequence information obtained using the methods of the invention can be combined with other characteristics of the protein under analysis to even further reduce the number possible identities of the protein. Thus, in a preferred embodiment, the method of the invention combines information from a protein sequence tag with one or more other protein characteristics to identify the protein. Data that is useful to supplement the sequence data includes, but is not limited to, amino acid composition, the number and identity of specific residues (e.g. cysteine), cleavage information, proteolytic (e.g., tryptic) and or chemolytic peptide mass, subcellular location, and separation coordinates (e.g., retention time, pI, 2-D electrophoresis coordinates, etc.). Other forms of data characteristic of a particular protein or class of proteins that can be combined with information from the PSTs of the invention to identify a protein will be apparent to those of skill in the art. As the body of data characteristic of a particular protein becomes more comprehensive, proteins under analysis can be identified using shorter protein sequence tags.

Thus, in a further preferred embodiment, information regarding one or more characteristics of a protein is combined with information from a PST of about 4 amino acids in length, more preferably about 3 amino acids in length, more preferably still, about 2 amino acids in length is used to identify the protein.

Sequencing Algorithm

The present invention will, in some embodiments, include the use of a mathematical algorithm for determining the protein sequence tag directly from mass spectra of fragmented labeled proteins. The algorithm can be used to determine a protein sequence tag from either terminus of the protein, providing that a unique mass tag label is attached to the terminus being sequenced. The starting mass spectra for use in the algorithm may be produced by any mass spectrometer in which a labeled protein or peptide can be fragmented. Time-of-flight mass spectra are preferred because of their improved mass accuracy over other mass spectrometer detection systems. However, other less accurate mass spectrometer detection systems may be used, particularly if an internal mass standard, such as fragmented label with no peptide attached, is used to improve the mass accuracy of the resulting mass spectrum. Protein fragmentation can be conducted either by CID in the collision cell of a tandem mass spectrometer or by in-source fragmentation in an electrospray or MALDI ionization source.

The algorithm requires the use of both the mass to charge position of a signal and its relative abundance. In one embodiment, the relative abundance of the signal is compared to that of immediately adjacent mass to charge positions and used to quantify the relative probability that a peak is present at the mass to charge position of interest. In this embodiment, the relative probabilities that a peak is present are compared among all competing sequences. In another embodiment the signal at each mass to charge position of interest is directly compared to that at the mass to charge positions of all competing sequences. The latter method is described further for clarity. One of skill in the art that will appreciate that this method can be adapted in many ways to provide a similar system for ranking competing sequences based on the relative abundance of the signal at the mass to charge positions correlated with each competing sequence.

The algorithm further consists of a cumulative sequence ranking system, in which the relative abundance of the ions predicted to result from each possible sequence are combined by product or summation with the relative abundances of ions predicted to result from subsequent residues (Equation 1). In this way sequence-specific differences in the ionization or fragmentation efficiency and adventitious matrix or overlapping noise peaks that confound the correct sequence assignment at each residue position in the polypeptide chain may be eliminated. The probability of an erroneous sequence assignment at any given residue position propagating forward to subsequent residue positions is lower than that associated with the true sequence. The overall rank for each possible sequence j can then determined by:

$$R_{j,n} = \prod_{i=1}^{n} p_{i,j} \text{ or } \sum_{i=1}^{n} p_{i,j} \tag{1}$$

where $R_{j,n}$ is the cumulative ranking given to any given sequence j at residue length n, and $p_{i,j}$ is the relative rank assigned to the sequence amongst its j peers at residue length i. It is apparent to those skilled in the art that many methods can be used to assign a relative rank (p) to each sequence j at any residue length i, consistent with comparison of the relative abundances of the signals at each competing mass to charge position (in supra). In a preferred embodiment, the relative ranking (p) of competing sequence possibilities at each residue length (i) may be determined by autoscaling the possibilities. In a particular variation of this method, the ranking (p) may be assigned based on an assumed or demonstrated probability distribution, such as the normal (Gaussian) probability distribution or the log normal (Poisson) probability distribution, such that the relative rank for each sequence will vary between 0 and 1. For example, $$p_i = NORMDIST\left[\frac{(C_{i,j} - \overline{C}_i)}{\sigma_i}\right] \text{ where;} \tag{2}$$

$$\overline{C}_i = \frac{\sum_{j=1}^{19^i} C_{i,j}}{19^i} \text{ and} \tag{3}$$

$$\sigma_i = \sqrt{\frac{\sum_{j=1}^{19^i} C_{i,j}^2 - \frac{\left(\sum_{j=1}^{19^i} C_{i,j}\right)^2}{19^i}}{(19^i - 1)}} \tag{4}$$

One of skill in the art will appreciate that the signal ($C_{i,j}$) corresponding to any sequence j containing i amino acid residues may be determined by any method which relates this signal back to the relative signal abundance in the mass spectrum. Collision induced fragmentation in the mass spectrometer may result in the production of more than one type of ion. CID methods in a tandem mass spectrometer commonly result in a, b, and c ion types from the N-terminus and x, y, and z ions from the C-terminus. In addition, the label and certain amino acid residues may contain "soft" charges that may lead to the production of labeled peptide fragments at more than one mass to charge position in the spectrum, depending on the number of such "soft" charges. In a variation of the method, the signals associated with each ion type and possible charge state may be combined to produce a cumulative signal associated with any given sequence j:

$$C_{i,j} = \sum_{k=\text{min charge states}}^{\text{max charge states}} \sum_{l=1}^{\text{max ion types}} c_{i,j,k,l} \quad (5)$$

where c is determined by calculating the (m/z) of the each ion type (k) and charge state (l) and looking up the corresponding counts ($c_{i,j,k,l}$) in the mass spectral data.

$$c_{i,j,k,l} = \text{LOOKUP}[(m/z)_{i,j,k,l}] \quad (6)$$

The mass to charge ratio calculation for any residue length i, sequence j, charge state k, and ion type l, is be determined from the stoichiometry and possible charge states of the amino acids and any attached labels in the sequence by methods previously described (see, Methods in Enzymology, Biemann, ed. 193:295–305, 351–360 and 455–479 (1993)).

A number of variations can be made to the basic sequencing method described. For example, in a preferred embodiment, the number of charge states and ion types that are used for determination of the total signal associated with any given sequence may be restricted to particular subsets empirically found to be most often associated with the fragmentation method. CID fragmentation in a tandem mass spectrometer preferentially yields b ions and y ions in the most abundance and c and x ions in the least abundance. In source fragmentation is found to yield only a, b, and y ions in significant abundance. In these cases, the algorithm may be preferentially adapted to ignore c and x ions or c, x, and z ions. Ion abundance also appears to diminish for the higher possible charge states of peptide fragments in both CID and in source fragmentation. This phenomenon may also be sequence specific with arginine and other imino "soft" charge species having a higher likelihood of retaining a charge than other amines (e.g., lysine or histidine residues). In another variation the mass to charge positions associated with higher numbers of charge states may be ignored on a sequence specific basis when determining the total signal associated with any sequence j.

In a variation, multiple labels (both isotopic and nonisotopic) can be incorporated into the algorithm using a dual sequencing approach. In this approach we define two residue tables, one for each label type (an any labeled residues). The sequencing algorithm is then applied using each residue table independently, such that the counts associated with the first label ($c_{i,j,k,l}$) are determined independently from those of a second label ($d_{i,j,k,l}$).

$$c_{i,j,k,l} = \text{LOOKUP}\big[(m/z)_{i,j,k,l}\big|_{Label1}\big] \quad (7)$$

$$d_{i,j,k,l} = \text{LOOKUP}\big[(m/z)_{i,j,k,l}\big|_{Label2}\big] \quad (8)$$

All the equations 1–6 apply to both c and d, and we can define:

$$q_i = \text{NORMDIST} = \left[\frac{(D_{i,j} - \overline{D}_i)}{\sigma_i^{label2}}\right] \quad (9)$$

-continued $$\overline{D}_i = \frac{\sum_{j=1}^{19^i} D_{i,j}}{19^i} \quad (10)$$

$$\sigma_i^{label2} = \sqrt{\frac{\sum_{j=1}^{19^i} D_{i,j}^2 - \frac{\left(\sum_{j=1}^{19^i} D_{i,j}\right)^2}{19^i}}{(19^i - 1)}} \quad (11)$$

$$D_{i,j} = \sum_{k=\text{min charge states}}^{\text{max charge states}} \sum_{l=1}^{\text{max ion types}} d_{i,j,k,l} \quad (12)$$

By multiplying the relative probability of each sequence j obtained with each label, we can get then obtain a composite ranking for the sequence.

$$R_{j,n} = \prod_{i=1}^{n} (p_i q_i) \text{ or } \sum_{i=1}^{n} (p_i q_i) \quad (9)$$

This variation can be further extended to more than one label. The mass spectrometer files used in this multiple labeling approach can be created by simultaneous fragmentation of a protein sample containing a known mixture of two or more labels. Moreover, mass spectrometer data from separate single label protein fragmentations can be added together to create a virtual multiple label mass spectrometer file for analysis by this method. This variation can be used with any type of multiple labeling strategies (supra).

In another preferred embodiment for isotopic labels, either natural isotopic abundances or with multiple labels of known relative isotopic abundances, the algorithm may be adapted to qualify or rank the peaks of competing sequences by their conformance to the expected abundances of the isotopic series. For example, where two isotopically distinct labels are employed of a known relative abundance, β, the mass to charge ratio of each sequence can be determined for both label isotopes, the corresponding count values determined from the mass spectral data, and a rank or probability of match to the expected abundance (β) determined.

Labeled Oligomers

While the invention is described above with reference to labeled proteins, one of skill in the art will recognize that the labels and labeling methods used are adaptable to the preparation of other labeled oligomers (e.g., labeled oligonucleotides, labeled oligosaccharides, and the like).

Nucleic acids may be sequenced by the invention through modification of the methods described by Butler et al., U.S. Pat. No. 6,090,558; Moforte et al., U.S. Pat. No. 5,700,642; and Koster, U.S. Pat. Nos. 6,194,144 and 5,691,141. Preferably, the methods herein use Sanger sequencing or polymerase chain reaction primers with "mass defect" labels either in the primer sequence, in the elongator sequence, or in the terminator sequence. The "mass defect" labels are those labels incorporating one or more elements having an atomic number from 17 to 77, more preferably from 35 to 63, with the proviso that said elements are other than sulfur or phosphorus. Preferably, either the primer or terminus is labeled to control the number of the "mass defect" elements incorporated into the nucleic acid oligomers so produced. Alternatively, the 3' or 5' ends of a nucleic acid may be labeled with a "mass defect" label and the nucleic acid fragmented by the method described by Maxam and Gilbert, *Proc. Natl. Acad. Sci.* (*USA*) 74:560–564 (1977) to yield a series of labeled fragments.

Oligosaccharides may be sequenced by the invention through modification of the methods described by Parekh et al., U.S. Pat. No. 5,667,984 and Rademacher et al., U.S. Pat. No. 5,100,778. Preferably, "mass defect" labels reactive with the reducing sugar end are used. More preferably, such labels would include pyridylamino functionalities wherein the pyridinyl ring is substituted with from one to three Br and/or I. Labeling may be conducted prior to selective enzymatic hydrolysis of the oligosaccharide or post enzymatic hydrolysis. Preferably, an oligosaccharide is labeled with a "mass defect" label before enzymatic hydrolysis and a different "mass defect" Label, after enzymatic hydrolysis to differentiate the original terminal reducing sugar.

Mass Tags for Simultaneous Analysis

While the invention is described above with reference to oligomers, one of skill in the art will recognize that the labels and labeling methods used are adaptable to the preparation of unique mass "tags" for other samples (e.g., tags for combinatorial chemistry libraries, tags for metabolites obtained from different samples, and the like). Such methods allow the simultaneous analysis and comparison of several samples by mass spectrometry.

Methods for Structure and Function Analysis

In yet another aspect, the present invention provides a method for structure and function analysis of an oligomer having a plurality of residues, the method comprising:

(a) contacting the oligomer with a mass defect labeling reagent to differentially label exposed residues and unexposed residues and produce a differentially labeled oligomer, wherein the mass defect labeling reagent comprises at least one element having an atomic number of from 17 to 77 that is other than sulfur or phosphorus;

(b) analyzing the differentially labeled oligomer by a mass spectrometric method to determine sequences of the oligomer that are exposed in the three-dimensional structure and sequences of the oligomer that are unexposed in the three-dimensional structure.

As with the methods above, relating to sequencing, this aspect fo the invention can be applied to essentially any oligomer (e.g., poteins, nucleic acids, oligosaccharides) for with some indication of three-dimensional structure and/or function of exposed residues is sought. The method finds particular use in the analysis of proteins.

Also, as above, the mass defect labeling reagent with typically contain at least one element having an atomic number of from 17 to 77, but exlusive of sulfur or phosphorus. For those applications in which protein structure information is desired, the mass defect labeling reagent can contain a phosphorus atom as this element is not present in proteins (with the exception, of course, of phosphorylated proteins). Preferably, the mass defect labeling reagent comprises an element having an atomic number of from 35 to 63, more preferably 39 to 58, exclusive of phosphorus or sulfur.

In one group of particularly preferred embodiments, the oligomer is a protein and the labeling reagent comprises either a bromine or an iodine atom. More preferably, the labeling reagent is bromine gas which is capable of labeling, for example, exposed tyrosine residues in a folded protein.

In other preferred embodiments, the mass spectrometric method employed uses ESI-TOF MS.

Other preferred embodiments and conditions for carrying out this aspect of the invention are as described above for labeling and sequencing of oligomers in general, and proteins, in particular.

Methods for Comparing the Relative Abundances of Analytes

In yet another aspect, the present invention provides a method for comparing the relative abundances of analytes from two or more samples, comprising:

(a) contacting the analytes of a first sample with with a labeling moiety to covalently attach a label to the analytes and form labeled analytes, the labeling moiety having one element with an atomic number from 17 to 77, with the proviso that the element is other than sulfur or phosphorus;

(b) contacting the analytes of subsequent samples with labeling moieties to covalently attach labels to the analytes in each sample, wherein the labeling moieties used for each subsequent sample contain an additional element with an atomic number from 17 to 77, with the proviso that the elements are other than sulfur or phosphorus;

(c) mixing the aliquots of labeled analytes; and (d) analyzing the labeled analytes using a mass spectrometric fragmentation method to determine the relative abundances of one or more of the analytes between the samples.

Preferred labeling moieties are those described throughout the specification, more preferably those having elements with atomic numbers of from 35 to 63, still more preferably from 39 to 58. The samples can be essentially any biological sample from animal tissue, plants or plant extracts, bacterial samples, viral samples, and the like.

Methods for Labeling Components of a Chemical Library

Another application of the mass defect labels is as tags for combinatorial chemical libraries. An exemplary use would be the creation of a mass defect tag concurrently with the synthesis of a combinatorial library. A typical synthesis involves building the combinatorial library tethered to a bead or well surface by sequencially adding different combinations or chemicals to wells. As described by Brenner and Lerner (*Proc. Natl. Acad. Sci* (*USA*), 89:5381–5383 (1992)) and Sugarman et al. (U.S. Pat. No. 6,056,926, issued May 2, 2000), it is also possible to concurrently synthesize a mass tag specific to the treatment steps or chemical composition of the specific chemical during the synthesis of the chemical library. Such tags may be created by the serial addition of different reactive groups onto a root tag. Such a root tag might be a primary amine. In which case one reactive group could be added to the root to create a secondary amine, where the mass of the reactive group would be changed to represent the chemical specific chemical identity or processing step to which the chemical entity from the library was exposed. In a subsequent step a second reactive group would be added to the secondary amine on the root tag to create a tertiary amine. This mass of this second group would represent a second chemical processing step or change in identity of the specific chemical in the combinatorial library. A similar approach, that allows more root tag combinations, would be the serial addition of various monomer units to an oligomeric root tag (e.g., Merrifield peptide synthesis).

However, this approach is limited by the number of possible tag combinations such that the additive masses of subsequent reactive group additions don't overlap when the final tag is analyzed by mass spectrometry. The present invention avoids this problem by adding additional mass defect elements to the growing root tag at each step. An additional problem solved by this invention is the ability to distinguish the tag created to identify the specific chemical in a combinatorial library from the mass of the chemical itself or the mass of any other component that may be present during an activity screen or assay of the specific chemical from the library. Use of mass defects in the tag allows the tag to be uniquely identified in a mass spectrum of either the chemical or library of chemicals and any matrix contaminants originating from the screening assay.

In view of the above, the present invention provides methods for using mass defect labels to indicate the synthetic sequence to which a chemical library member has been exposed during the course of synthesis.

In particular, the present invention provides a method for tagging the elements of chemical libraries, either during synthesis or screening, comprising;

(a) contacting a root tag with a labeling moiety to covalently attach a label to the root tag and form a labeled tag, said labeling moiety having one element with an atomic number from 17 to 77, with the proviso that said element is other than sulfur or phosphorus;

(b) optionally, contacting a root with additional labeling moieties to covalently attach additional labels to the root tag and form a multiply labeled tag, said labeling moiety having one element with an atomic number from 17 to 77, with the proviso that said element is other than sulfur or phosphorus; and (c) analyzing the labeled tag by mass spectrometric methods to determine both its mass and the number of elements with an atomic number from 17 to 77, such that the mass and number of elements identifies the chemical processes to which the specific chemical of the library has been exposed and the identity of the chemical from the library.

Preferred elements (e.g., mass defect elements) are as described for other aspects of the invention above.

The materials, methods and devices of the present invention are further illustrated by the examples which follow. These examples are offered to illustrate, but not to limit the claimed invention.

EXAMPLES

Example 1

Figure 7:
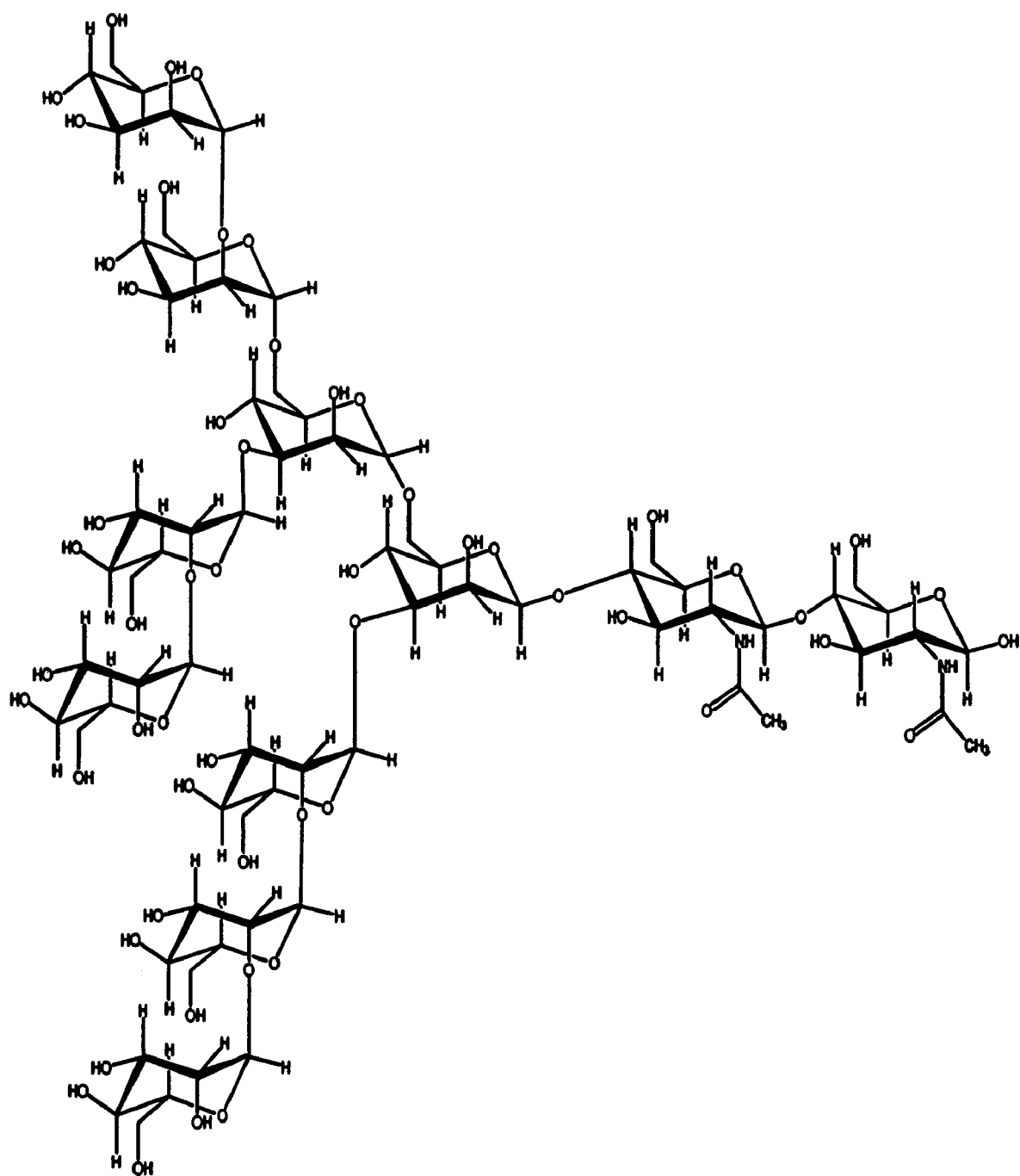
FIG. 7 provides the structure of a high mannose-type oligosaccharide that can be sequenced using the methods provided in Example 1.

In this example, a high mannose-type oligosaccharide (FIG. 7) is labeled and sequenced. The oligosaccharide is labeled using methods similar to those described in Parekh, et al., U.S. Pat. No. 5,667,984. Briefly, a mass defect label (2-amino-6-iodo-pyridine (Label 1)) is covalently attached to the reducing terminus of the oligosaccharide in the presence of sodium cyanoborohydride (NaBH$_3$CN). This incorporates a single mass defect element (iodine) into the parent oligosaccharide. The addition of the mass defect element allows the labeled oligosaccharide fragments to be distinguished from unlabeled fragments and matrix ions in the mass spectrum.

The Label 1-conjugated oligosaccharide is then aliquoted to reaction tubes containing different saccharases (see Tables 1.1 and 1.2) in appropriate reaction buffers. The reactions are allowed to proceed to completion and the resultant reaction products are conjugated at the newly formed reducing ends of the fragments by reaction with the mass defect labels shown for each enzyme (see Table 1.2), again in the presence of sodium cyanoborohydride. Each of Labels 2 and 3 contain different numbers of mass defect elements, allowing the digest fragments to be distinguished from the terminal fragment of the original oligosaccharide.

TABLE 1.1

Oligosaccharase Enzymes

| Enzyme # | Species | Enzyme |
|---|---|---|
| 1 | Aspergillus saitoi | α-mannosidase I |
| 2 | Jack bean | α-mannosidase |
| 3 | Achatina saitoi | α-mannosidase II |
| 4 | Jack bean | β-hexosaniinidase |
| 5 | Prevotella sp. | β-hexosaminidase |
| 6 | Achatina fulica | β-mannosidase |
| 7 | Streptococcus pneumonae | N-acetyl β-hexosaminidase |
| 8 | Helix pomatia | β-mannosidase |

TABLE 1.2

Reaction and Label Combinations

| Enzyme* | Action | Mass Defect Label Used |
|---|---|---|
| None | None | 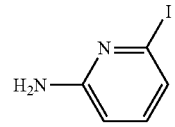 Label 1 |
| 1 | Cleaves 1 α 2 mannoses at any site | 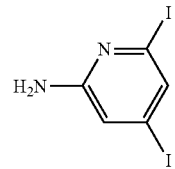 Label 2 |
| 3 | Cleaves 1 α 3, 6 mannoses to any site Cleaves 1 α 3 mannoses when linked to a branched sugar | 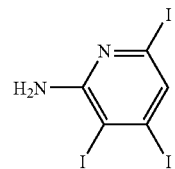 Label 3 |

*Enzyme number corresponds to the description in Table 1.1

An aliquot of the Label 3-conjugated reaction mixture (i.e., digested with Enzyme #3) is further digested with Enzyme 1. The reducing sugar termini generated by this reaction are subsequently conjugated to Label 2 as previously described.

Aliquots from all these reactions are then mixed, acidified by the addition of a 50% v/v mixture of 2% acetic acid in methanol and subjected to mass spectral analysis. Because of the low stability of the acetal conjugate in acid solutions mass spectral analysis is conducted immediately after acidification. Alternatively, a different label series that incorporates a hard charge (e.g., an N-alkyl-iodo-pyridinium series) may be subjected to mass spectral analysis without acidification. The resulting mass spectrum is deconvolved to remove all chemical noise that does not contain a mass defect labeled peak by the methods of this invention. The resulting deconvolved mass defect spectrum is then algorithmically searched by the methods of this invention by predicting all the possible oligosaccharide sequences that could be attached to each mass defect label used.

Figure 8B:
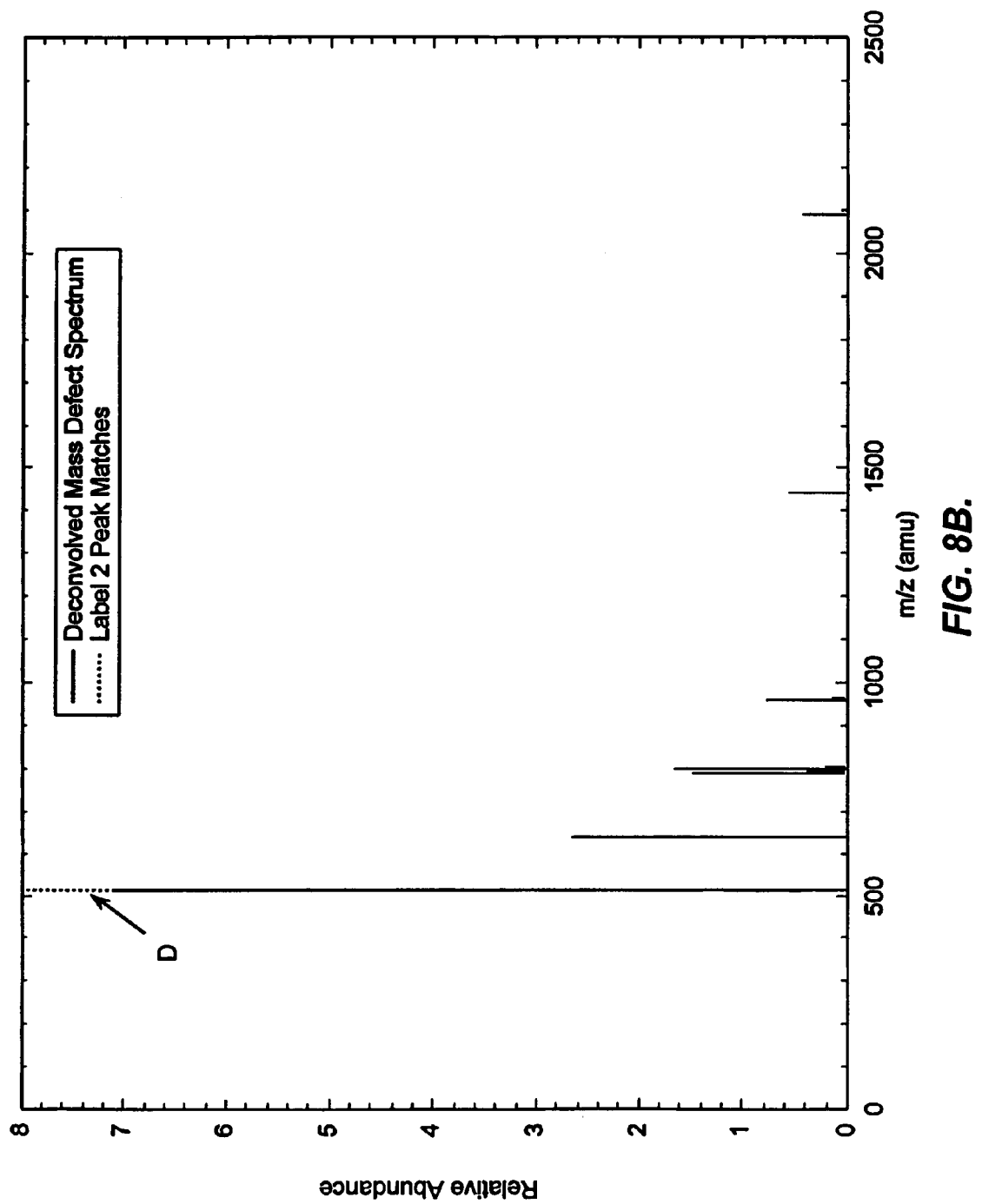
FIG. 8B shows the deconvolved mass defect spectrum for a high mannose-type oligosaccharide digest labeled with Label 2.
Figure 8C:
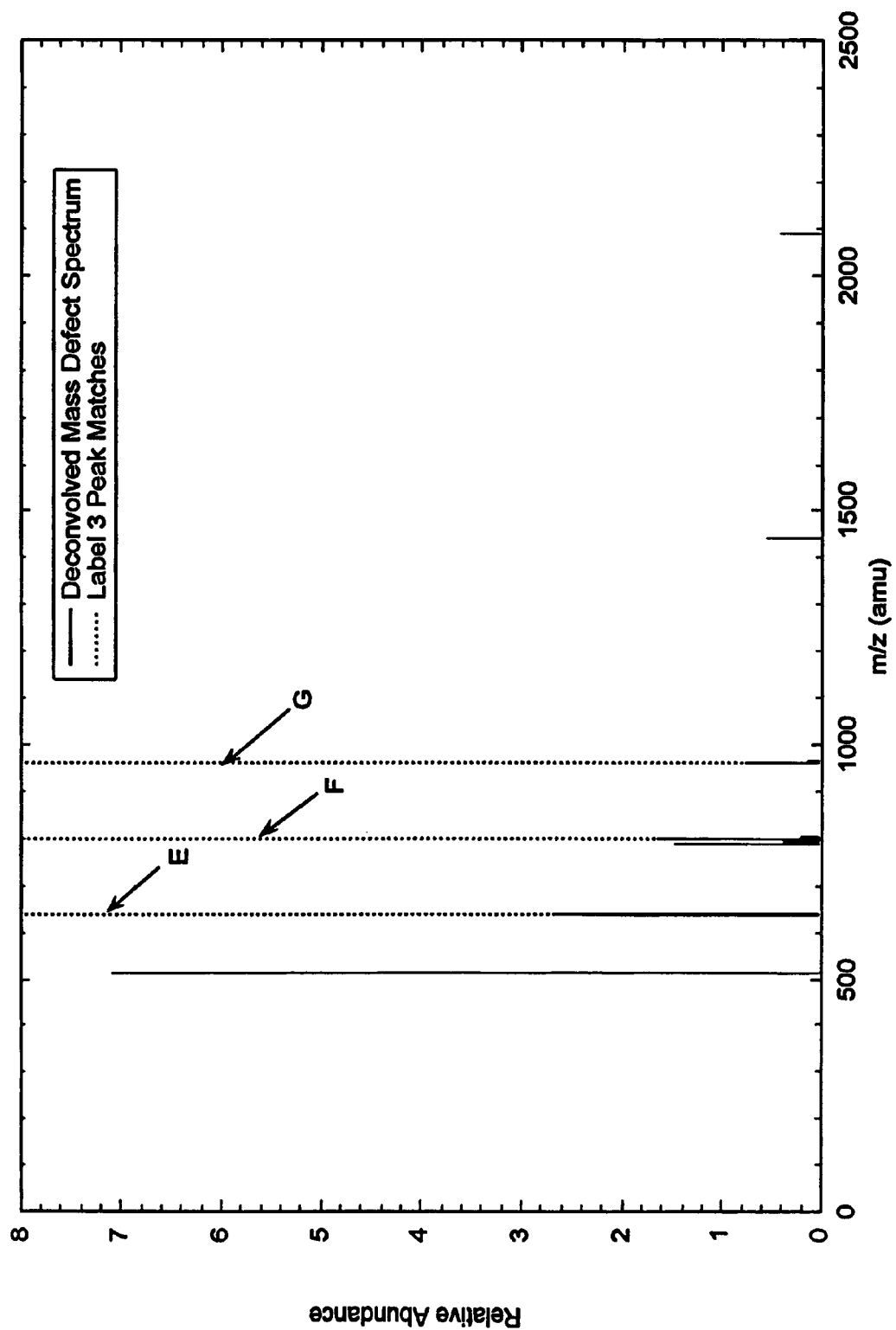
FIG. 8C shows the deconvolved mass defect spectrum for a high mannose-type oligosaccharide digest labeled with Label 3.

The search algorithm calculates the mass for every branch combination of hexose (Hex) and N-acetylaminohexose (HexNAC). Each Hex monomer unit adds a monoisotopic mass unit of 179.055565 amu to the weight of the estimated fragment mass. Each HexNAC monomer unit adds a monoisotopic mass of 220.082114 amu to the estimated fragment mass. There is a net loss of (n−1) times 17.00274 amu for each sugar (n) contained in the fragment. The oligosaccharide composition of the peaks matching the search criteria for Labels 1, 2, and 3 are shown in FIGS. 8A, 8B, and 8C, respectively. The number of hexoses and N-acetylaminohexoses corresponding to these peaks are shown in Table 1.3.

TABLE 1.3

Number and Type of Hexoses
Corresponding the FIG. 1 (A, B, and C) Peaks

| Peak | HexNAC | Composition Hex |
|---|---|---|
| A | 2 | 1 |
| B | 2 | 5 |
| C | 2 | 9 |
| D |   | 1 |
| E |   | 1 |
| F |   | 2 |
| G |   | 3 |

The mass ladder formed from the fragments conjugated to Label 1 indicate that the outermost sugars are be hexoses. The highest mass fragment conjugated to Label 1 corresponds to the parent oligosaccharide. As a result, the four hexose mass difference between the first Label 1-conjugated fragment and the parent indicates the presence of four α-mannoses since both enzyme 1 and enzyme 3 only cleave α-mannoses. Since peak D is the only label 2 conjugate match in FIG. 8B, four of the outermost sugars from the reducing terminus must be 1α2 linked mannoses and there can be no internal 1α2 mannoses.

The next fragment in the Label 1 mass ladder (Peak A) differs by an additional 4 hexoses from the previous fragment. This must correspond to a sample digested with enzyme 3. The only matching Label 3-conjugated fragments (FIG. 8C) are E (a 1 hexose fragment), F (a 2 hexose fragment) and G (a 3 hexose fragment). Since peaks F and G total 5 hexoses, at least one of these fragments must contain a 1α2 linked mannose. Since enzyme 3 only cleaves 1α3 and 1α6 linkages, therefore, there must be at least two separate 1α3 and/or 1α6 linked mannoses in the structure and these mannoses must be interior to the 4 1α2 linked mannoses. From this information the following partial sequence can be derived:

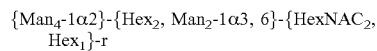
{Man$_4$-1α2}-{Hex$_2$, Man$_2$-1α3, 6}-{HexNAC$_2$, Hex$_1$}-r where r indicates the reducing end of the oligosaccharide.

This process is repeated with different enzymes from Table 1.1 until the complete sequence is determined. For example, digestion with enzyme 3 followed by enzyme 8 allows the determination that the initial sequence is:

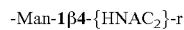
-Man-1β4-{HNAC$_2$}-r

The full sequence of the reducing end of the oligosaccharide is determined by reaction with enzyme 3 followed by enzyme 7.

Example 2

In this example a mass defect label is used for the identification of the fatty acid composition and arrangement in lipids, or "lipid sequencing." This example utilizes phosphatyidylcholine; however, one of skill in the art will appreciate that these methods in combination with alternative separation methods, spot, and lipase selections can be applied to any of the saponifiable lipids as defined by Lehninger (see, BIOCHEMISTRY (Worth, N.Y., 1975)).

A lipid extract is prepared via ether extraction of an *E. coli* K-12 cell pellet using the method of Hanson and Phillips (see, MANUAL OF METHODS FOR GENERAL BACTERIOLOGY, p. 328, Amer. Soc. Microbiol., Washington, D.C., 1981). Ether was removed from the extract by evaporation and the lipid pellet was resuspended in a 65:25:5 methanol:chloroform:formic acid solvent system (containing 0.1% butylated hydroxytoluene to inhibit oxidation). Half the volume was spotted in each of two lanes of a scribed silica HL plate (Altech, Deerfield, Ill.) and allowed to dry. The lipids were separated using a solvent system described by Waters and Huestis, AMPHIPATHIC INTERACTIONS WITH ERYTHROCYTES AND PLATELETS, DOCTORAL DISSERTATION (Stanford University, Stanford, Calif., Dept. of Chemistry, 1992). This process separates the lipids by head groups. One lane was removed and exposed to iodine vapor to determine the relative positions of each of the lipid fractions. The silica matrix was scraped from the region in the undeveloped lane corresponding to the phosphatidylcholine spot and was placed into a microfuge tube.

The silica pellet was resuspended in 100 μl of phospholipase reaction buffer (100 μl) as described by Cottrell, METH. ENZYMOLOGY, 71:698 (1981) and vortexed vigorously. An aliquot (50 μl) of the silica suspension was removed to a second microfuge tube. The first aliquot was treated by the addition of 1 IU of phospholipase A2 from *Apis mellifera* (Sigma-Aldrich, St. Louis, Mo.), which selectively hydrolyzes the C2 fatty acids. The second aliquot was treated by the addition of 1 IU of Novozyme 871 (Sigma-Aldrich, St. Louis, Mo.), which selectively hydrolyzes the C3 fatty acids of phosphoglycerides. Both reaction mixtures were incubated at room temperature overnight.

The reaction mixtures were evaporated to dryness under vacuum, and resuspended in approximately 25 μl of dichloromethane. Mass defect Label 1 (2-amino-5-iodo-pyridine) was added (20 μl of a 1 M solution in dichloromethane) to the phosphorylase A2 reaction mixture. Mass defect Label 2 (2-amino-3,5-diiodo-pyridine) was added (20 μl of a 1 M solution in dichloromethane) to the Novozyme 871 reaction mixture. An aliquot (20 μl of a 1 M solution of 1,3-dicyclohexylcarbodiimide) was then added to both tubes and incubated for 2 hours. The carbodiimide catalyzed the conjugation of the enzyme liberated fatty acids to the mass defect labels. The reaction mixtures were acidified by addition of 1% formic acid (v/v) and mixed immediately prior to mass spectrometric analysis by microspray on an ABI Mariner MS.

Figure 9:
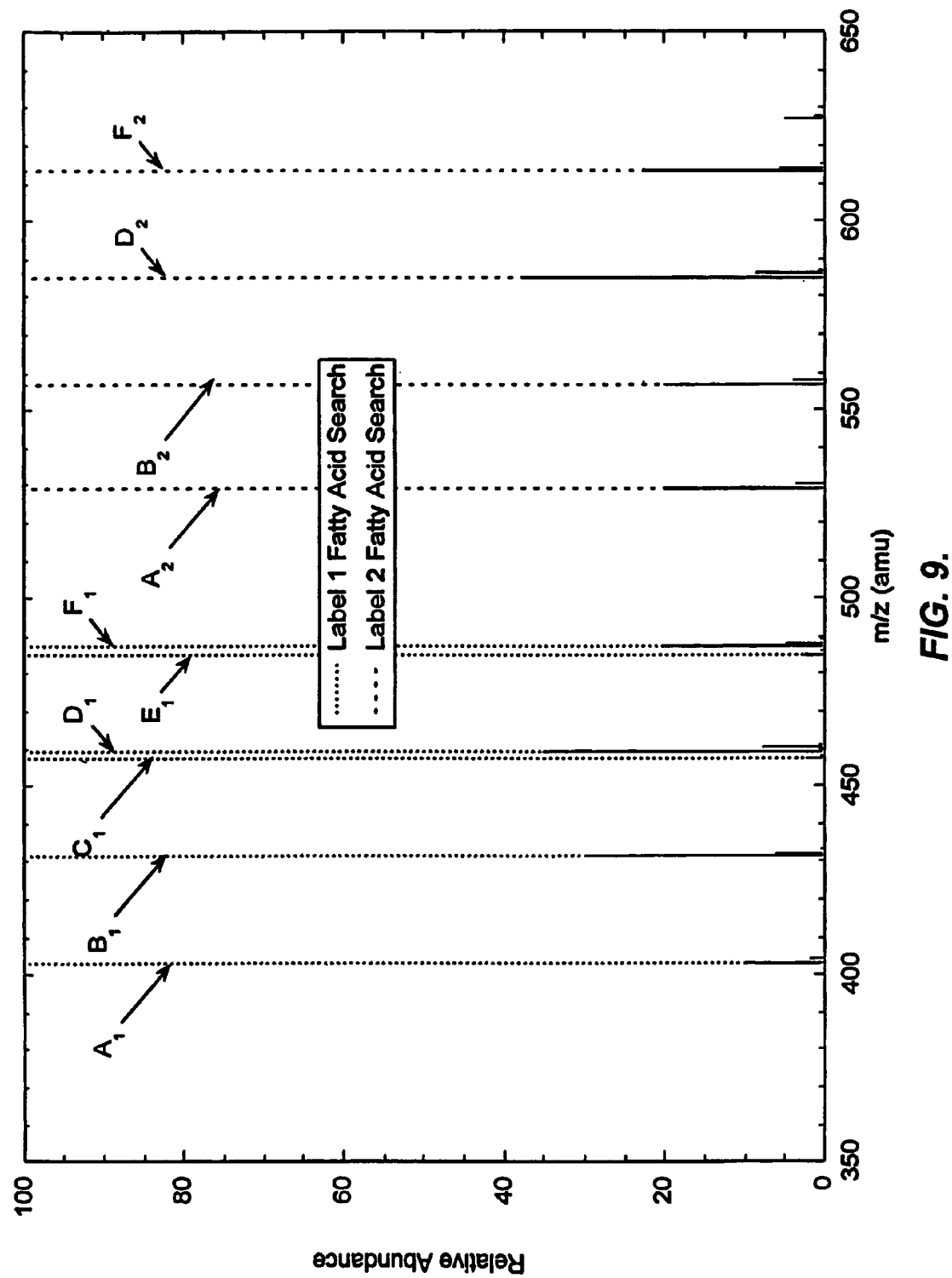
FIG. 9 shows the deconvolved mass defect spectrum for a lipid labeled with Label 1 and Label 2 (see Example 2).

The chemical noise was deconvolved from the resulting mass spectrum by the algorithms of the present invention, leaving the deconvolved mass spectra shown in FIG. 9. The identities and relative abundances of the various fatty acids at C2 and C3 on the phosphatidylcholine lipid backbone were determined by mass addition to each label. The lengths of the natural fatty acid tails occur in multiples of either —CH$_2$CH$_2$— (28.031300 amu) or —CH═CH— (26.015650) units. The mass of one H (1.007825 amu) is added to each predicted chain length to complete the stoichiometry of the terminal methyl group. Branched fatty acids cannot be distinguished from single chain analogs because the loss of one hydrogen from the mass at a branch point is recovered by the extra H needed to complete the stoichiometry at the terminus of the new branch.

The relative abundance of the various fatty acids at the C2 position can be estimated from the monoisotopic peak heights for the various Label 1-conjugated peaks (A$_1$→F$_1$, FIG. 9). The relative abundance of the various fatty acids at the C3 position of phosphatidylcholine can be estimated from the monoisotopic peak heights for the various Label 2-conjugated peaks ($A_2 \rightarrow F_2$, FIG. 9). Therefore, the average sequence of the phosphatidylcholine of *E. coli* is shown in Table 2.1.

Further lipid sequence resolution can be obtained through the use of a second thin layer chromatography dimension or other separation method in which the hydrophobicity of the fatty acids is used to resolve the lipids (see, for example, Morris, *J. Lipid Res.*, 7:717–732 (1966)).

TABLE 2.1

*E. Coli* Phoshatidylcholine Sequence Composition

| | | Approximate Abundance (%) | |
|---|---|---|---|
| Peak | Fatty Acid | C3 (Label 2) | C2 (Label 1) |
| A | n-dodecanoic | 20 | 10 |
| B | n-tetradecanoic | 20 | 30 |
| C | palmitoleic | — | 2 |
| D | n-hexadecanoic | 37 | 35 |
| E | oleic | — | 2 |
| F | n-octadecanoic | 22 | 20 |

Example 3

This example describes the preparation of photocleavable mass defect labels having bromine or iodine substituents. These labels are useful for quantifying the relative abundances of biomolecules (e.g., nucleic acids, proteins, or metabolites) that may otherwise exhibit low ionization or detection efficiencies in the mass spectrometer. The mass defect label serves as a surrogate marker for its conjugate biomolecule in the mass spectrometer. Variations of the terminal chemistry provide means for attachment to primary amine, sulfhydryl, and carboxylic acid containing biomolecules. The inclusion of the mass defect element in the label allows the label to be unambiguously resolved from overlapping chemical noise that may be present in the sample and two samples from one another when different numbers of mass defect elements are incorporated into two labels (see also Example 1).

Briefly, 4-(tert-butyldimethylsilyl)-phenylborate ether (FT106), prepared as described by Schmidt et al. WO 99/32501 (Jul. 1, 1999) is mixed with one of the corresponding commercially-available bromo- or iodo-phenols shown in Table 3.1 to form the corresponding brominated or iodinated mass defect label precursors using methods as described in Schmidt et al. WO 99/32501 (Jul. 1, 1999). Additional aryl ether linkages can be inserted between FT106 and the terminal mass defect-containing aryl group through the incorporation of a commercially-available hydroquinone or 4,4'-dihyroxydiphenyl ether. To accomplish this, the terminal phenol is reactivated using a phenylboronic acid terminus by the same method used to create FT106. Similarly, branched aryl ethers can be created by addition and reactivation of the commercially-available 1,2,4-benzenetriol.

The tert-butyl-dimethyl silane protecting group of the mass defect label precursor (MDP1 through MDP5, Table 3.1) is removed with a molar excess of trimethylsulfonium fluoride in methylene chloride or other suitable means generally known in the art. The corresponding deprotected phenol is further coupled to an appropriately-blocked amino linker (see, for example GB 98/15163.2 (Jul. 13, 1998)) which is subsequenctly converted to the primary amine as described by Schmidt et al. ibid. The amine can be further reacted with any appropriate phenyl vinyl sulfone. Examples of appropriate phenyl vinyl sulfones include, but are not limited to, those with blocked primary amine (or a nitro group that can subsequently be reduced to an aniline), carboxylic acid (e.g., trifluoroacetate ester), or thiol (e.g., a disulfide linkage) substitution on the phenyl ring. The 2° amino group of the linker is then reacted with trifluroacetic anhydride or methane sulphonyl chloride to render the label photocleavable. Finally, the blocking agent is removed by methods generally recognized in the art and the photocleavable mass tag is conjugated to molecule or macromolecule through the free amine, carboxylic acid, or thiol group by any suitable, generally recognized, conjugation methods to yield a photocleavable mass defect tag conjugated molecule.

TABLE 3.1

Commercially-Available Bromo- and Iodo-Phenols

| Substitued Phenol | Code | Mass Defect Label Precursor |
|---|---|---|
| 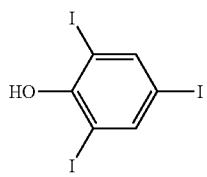<br>2,4,6-Triiodo-phenol | MDP1 | 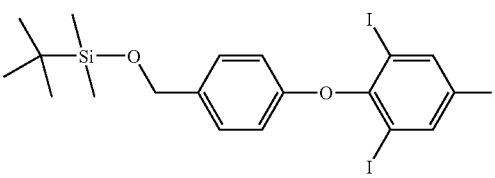<br>tert-Butyl-dimethyl-[4-(2,4,6-triiodo-phenoxy)-benzyloxy]-silane |
| 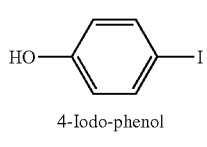<br>4-Iodo-phenol | MDP2 | 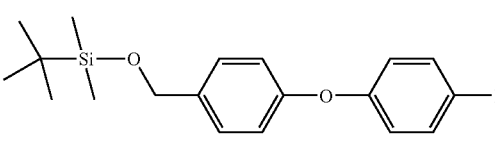<br>tert-Butyl-[4-(4-iodo-phenoxy)-benzyloxy]-dimethyl-silane |

TABLE 3.1-continued

Commercially-Available Bromo- and Iodo-Phenols

| Substitued Phenol | Code | Mass Defect Label Precursor |
|---|---|---|
| 3-Bromo-phenol | MDP3 | [4-(3-Bromo-phenoxy)-benzyloxy]-tert-butyl-dimethyl-silane |
| 2,6-Dibromo-4-nitrophenol | MDP4 | [4-nitro-(2,6-dibromo-phenoxy)-benzyloxy]-tert-butyl-dimethylsilane |
| 4-Bromo-2-nitrophenol | DMP5 | [2-nitro-(4-bromo-phenoxy)-benzyloxy]-tert-butyl-dimethylsilane |

Example 4

This example illustrates the use of affinity-coupled mass labels for the rapid and quantitative analysis of affinity purified mass defect labeled compounds obtained from different samples. In this example, proteins are used, but one of skill in the art will appreciate that this method can be applied to the analysis for comparison of any molecules co-purified from different samples.

Preparation of the label starts with any suitable heterobifunctional aryl bromide or iodide (such as the commercially-available examples shown in Table 4.1). MDP4 and MDP5 (Table 3.1) are also useful. Each of these anilines can be reacted with a stoichiometric excess of an N-hydroxysuccimide (NHS) ester of an affinity reagent, such as the commercially-available NHS-iminobiotin or biotin molecules in anhydrous acetonitrile. The reaction mixture is incubated for at least 2 h before the addition of water to hydrolyze any unreacted NHS-ester. The solvent is evaporated to dryness.

The nitro group is then reduced to a primary amine using standard methods, such as dilute HCl with $SnCl_2$ added as a catalyst. The reaction product (see compound 4.1 below) is purified by affinity chromatography and evaporated to dryness. The amino group (produced by reduction of the nitro group) is then reacted with another suitable crosslinker (e.g., iodoacetic anhydride) or may be used directly for linkage to carboxylic acid containing target molecules using carbodiimide chemistry. Alternative linkage chemistries suitable for reaction with primary amines can also be used.

Optionally, the amino group (or second aniline terminus) can be extended by reaction with hydrogenated and perdeuterated polyethylene glycols, as described by Aebersold et al. (WO 00/11208 (Mar. 2, 2000)) to produce a series of isotopically-distinct mass defect tags for differential labeling. Similarly, isotopically pure aryl bromide or iodide starting materials may be used to generate isotope-coupled affinity tags directly.

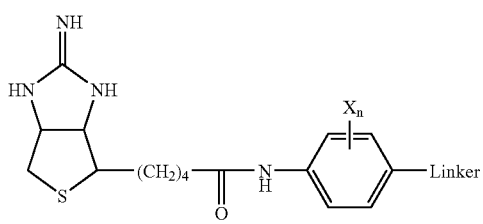

4.1

Compound 4.1 illustrates a mass defect labeled iminobiotin affinity tag where X represents a mass defect element (e.g., bromine or iodine) and n represents the number of mass defect elements. The Linker is any linkage chemistry that can be used to attach the mass defect affinity-coupled tag to a target molecule. Examples include aniline (which can be linked to carboxylic acids through carbodiimide chemistry), iodoacetamide (formed by reaction of aniline with iodoacetic anhydride), or azide formed by reaction with nitric acid.

TABLE 4.1

Examples of Affinity-Coupled Mass Defect Labels

| Heterobifunctional aryl bromide or Iodide | Code | Affinity-Coupled Mass Defect Label |
|---|---|---|
| 2-bromo-4-nitroaniline | MDA1 | (biotin)-(CH$_2$)$_4$-C(O)-NH-(2-bromo-4-aminophenyl) |
| 2,6-dibromo-4-nitroaniline | MDA2 | (biotin)-(CH$_2$)$_4$-C(O)-NH-(2,6-dibromo-4-aminophenyl) |
| 2,6-diiodo-4-nitroaniline | MDA3 | (biotin)-(CH$_2$)$_4$-C(O)-NH-(2,6-diiodo-4-aminophenyl) |

To illustrate the use of such tags, blood plasma samples (1 ml) are obtained from each of two patients and placed into separate microfuge tubes. Each tube is treated as follows. The macromolecules are precipitated by the addition of trichloroacetic acid to a final concentration of about 10% w/v and the tubes are incubated on ice for 20 min. The precipitate is pelleted by centrifugation (14,000 g) and the supernatant is removed. The pellet is dried under vacuum. The dried pellet is resuspended in 100 microliters of a suitable tryptic digestion buffer containing 100 IU of trypsin and 0.1% w/v tris(2-carboxyethyl) phosphine hydrochloride. The solution is incubated overnight at 37 C.

Isotopically pure aliquots of MDA1 (mass defect affinity label 1) are prepared with an iodoacetamide linker. An aliquot (50 microliters) of the tryptic digest of sample 1 is added to a microfuge tube containing 10 mg of [$^{79}$Br]-MDA1. A similar 50 microliter aliquot of the tryptic digest of sample 2 is added to a microfuge tube containing 10 mg of [$^{81}$Br]-MDA1. Both tubes are incubated for 3 h prior to mixing the contents together. The affinity-labeled molecules are purified by chromatography through a streptavidin-agarose affinity column (Sigma-Aldrich, St. Louis, Mo.) following the manufacturer's recommended procedure. The recovered tagged peptide mixture is analyzed by mass spectrometer with the mass defect peaks deconvolved from the chemical noise generated from unlabeled peptides by the methods of the present invention. All remaining isotopically-distinct pairs of peaks were quantified for their relative abundance.

Example 5

This example illustrates the use of photocleavable mass tags in sequencing methods.

Using the methods of the present invention mass defect elements such as bromine and europium were specifically incorporated into the weight range adjuster component of a photocleavable component described by Ness et al., U.S. Pat. No. 6,027,890. The mass defect provided by these elements allows fragments containing the mass defect labels to be deconvolved from the chemical noise generated from other organic molecules that may be present in the sample. In addition, this example shows how the use of peak pairing deconvolution algorithms, described herein, allows qualification of low signal peaks in the spectrum when mass defect elements with high natural abundances of stable isotopes are used.

The synthesis proceed as described in Example 5 of Ness et al. ibid., with the exception that the R$_{1-36}$ compounds added at step H consist of bromophenylamide derivatives of amino acids with varying chain lengths. The bromophenylamide derivatives are prepared as follows:

About 5 g of 3-bromobenzoic acid and 5 g of 1,3-dicyclohexylcarbodiimide is dissolved in 100 ml of dry toluene. About 10 ml of this solution is aliquoted into each of 10 reaction vials. To each 10 ml aliquot, a stoichiometric quantity of one of the tert-butyl esters of the amino acids in Table 5.1 is added relative to the bromobenzoic acid. A different amino acid tert-butyl ester (prepared by standard methods) is added to each tube. The reaction is allowed to proceed overnight at room temperature and unreacted tert-butyl ester is removed by the addition of trifluoroacetic acid. Solvent is then removed by evaporation and the bromophenylamide derivatives are purified by preparative reverse phase HPLC using reverse-phase chromatography with gradient elution.

The bromophenylamide derivatives are dissolved and chromatographed using a YMC brand $C_8$ or $C_{18}$ stationary phase (dimensions ~25 cm×6 mm I.D., 5–15 µm, 120–150 Å) and a gradient mobile phase consisting initially of a mixture of acetonitrile and/or methanol with water in a 50/50 ratio; flow rate and gradient are adjusted by the analyst for the specific bromophenylamide derivative. The water phase may optionally be modified to contain 0.1 molar ammonium acetate, diethylamine, triethylamine, or ammonium hydroxide to aid in solubility of the analyte in the mobile phase in cases where extreme tailing or peak broadening has occurred. The organic portion may optionally be modified in strength via adding 1–10% (by volume) of isopropyl alcohol, diisopropyl alcohol, or tetrahydrofuran to effect changes in selectivity between the constituents in the analyte mixture and enable the isolation of the desired bromophenylamide label material from its impurities. The gradient is implemented by changing the total solvent strength from ~50% organic (by volume) to around 90–100% organic over the course of 10 to 20 minutes. Refinement of the mobile phase constituents, flow rate, initial and final solvent strengths, and gradient velocity are made for each derivative as would normally be done by one skilled in the art. Isolated fractions of the desired bromophenylamide material are combined and evaporated prior to incorporation into the mass tag.

Figure 10:
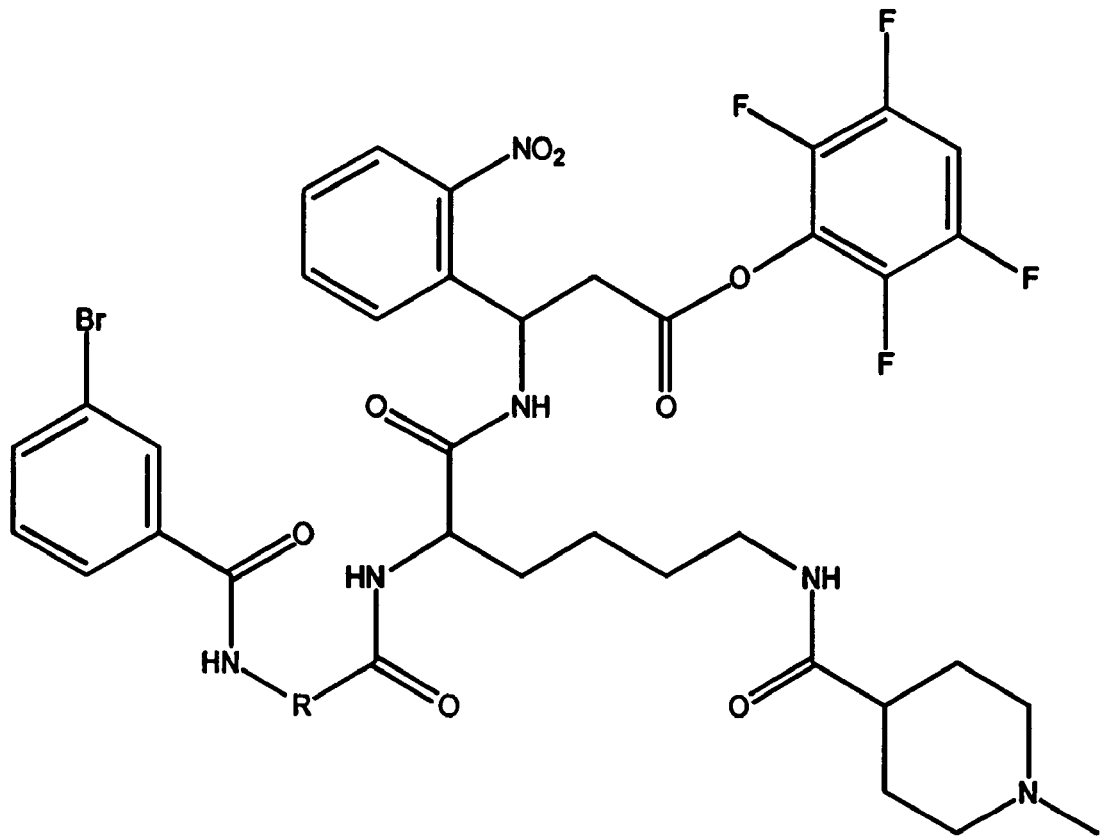
FIG. 10 illustrates a general structure for a photocleavable mass defect label where Br is the mass defect element that is linked through the amino acid (R) to the remainder of the label (or tag).

This procedure generates a series of labels with the general composition shown in FIG. 10, which can be reacted with any primary amine containing target molecule(s) through the tetrafluorophenyl-blocked acid moiety.

TABLE 5.1

Amino Acids for Use in Preparation of Group VI
Variable Weight Components for Mass Tags Glycine; alanine; 4-aminobutyric acid Leucine or Isoleucine; 2-Aminooctanoic acid; Asparagine TABLE 5.1-continued Amino Acids for Use in Preparation of Group VI
Variable Weight Components for Mass Tags Glutamine; Phenylalanine; 2-aminoheptanoic acid 2-Aminodecanoic acid; Valine; 2-Aminopelargonic acid Example 6

This example illustrates the use of a photocleavable mass defect label generated in Example 5, above, in sequence determination of bradykinin.

In this example the 3-bromobenzoic acid and alanine conjugate mass tag label is attached to the N-terminus of the peptide bradykinin using methods generally recognized in the art. The labeled peptide is diluted to about 1 ng per microliter into a 50:50:1 by volume acetonitrile:water:triethylamine solution. The solution was injected at about 1 microliter per minute into an Applied Biosystems Mariner ESI-TOF mass spectrometer equipped with the standard microspray head and run in negative ion mode. The spray and mass spectrometer settings were optimized for the highest relative abundance of the 3-charge state of the oligonucleotide $dT_6$ that could be achieved with a peak resolution greater than 5000. An Ar-pumped standing wave dye laser (Coherent), which was tuned to 350 nm, was directed at the gap between the spray tip and the nozzle of the mass spectrometer, such that the sample spray would be fully exposed to the laser light to cleave the mass tag.

Figure 11A:
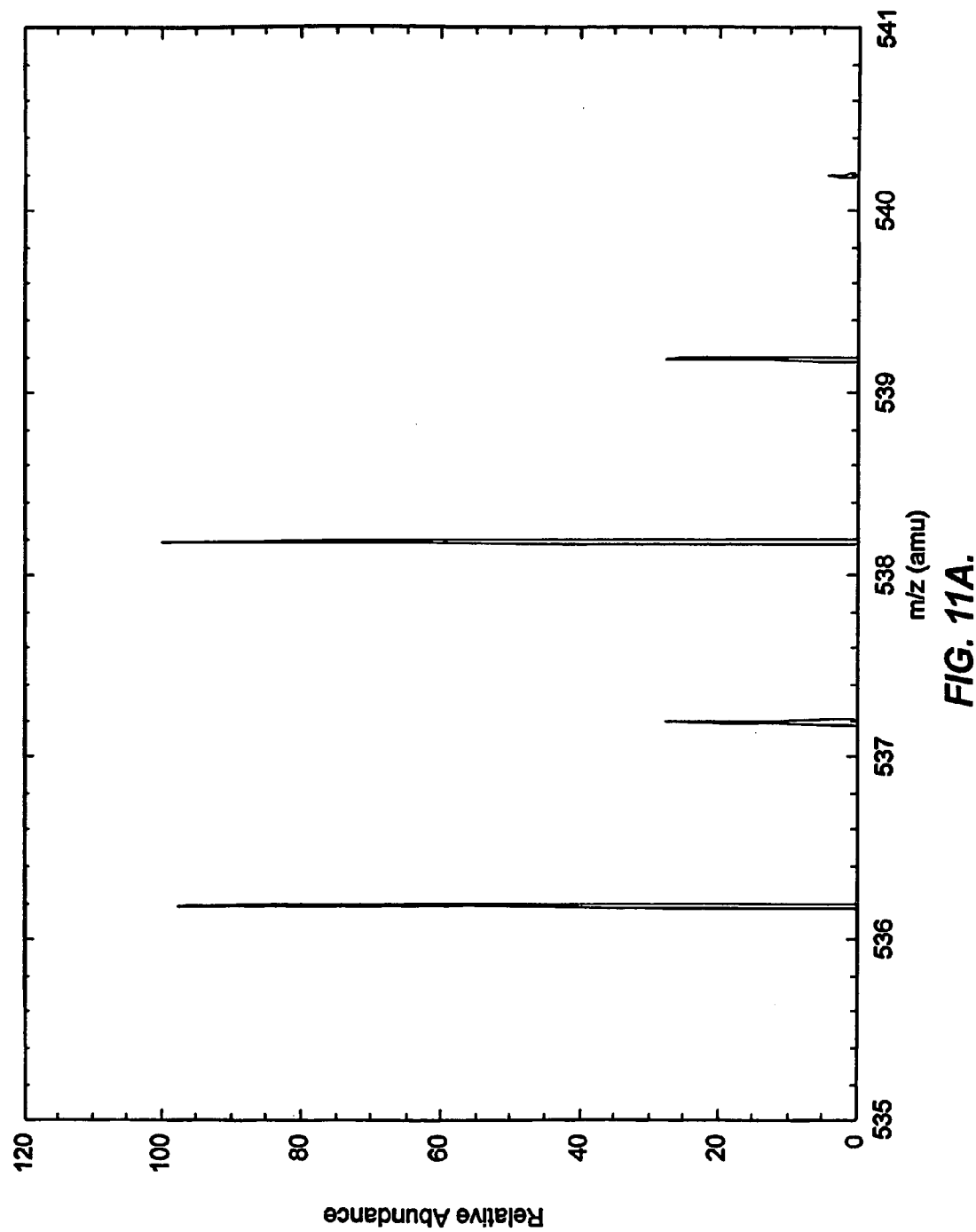
FIG. 11A shows the deconvolved mass spectrum of the photo cleared mass defect.

The mass tag labeled sample was analyzed by accumulating 30 scans of 3 seconds duration. The chemical noise in the mass spectrum was deconvolved using the algorithms of the current invention, leaving the mass defect label peaks (FIG. 11A).

These deconvolved peaks were further qualified by the relative abundances of their isotope pairs using the algorithm:

$$\beta = \left( \frac{(Counts_{[79_{Br}]} + Counts_{[81_{Br}]})}{2} \right) \left[ 1 - \frac{|Counts_{[79_{Br}]} - Counts_{[81_{Br}]}|}{(Counts_{[79_{Br}]} + Counts_{[81_{Br}]})} \right]$$

Figure 11B:
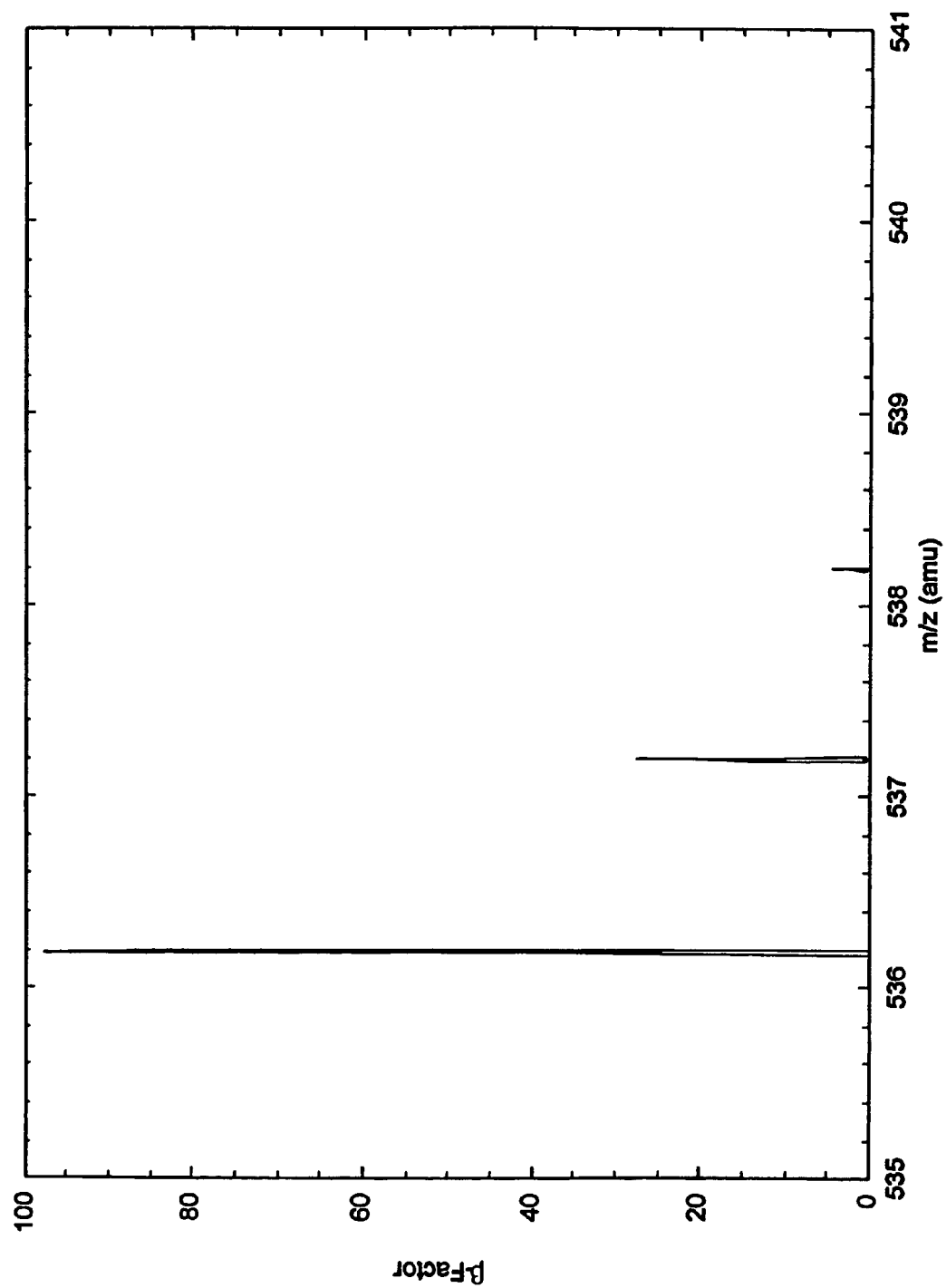
FIG. 11B shows the tag bromine isotope resolved spectrum of the photo cleared mono-isotopic mass defects tag.
Figure 11C:
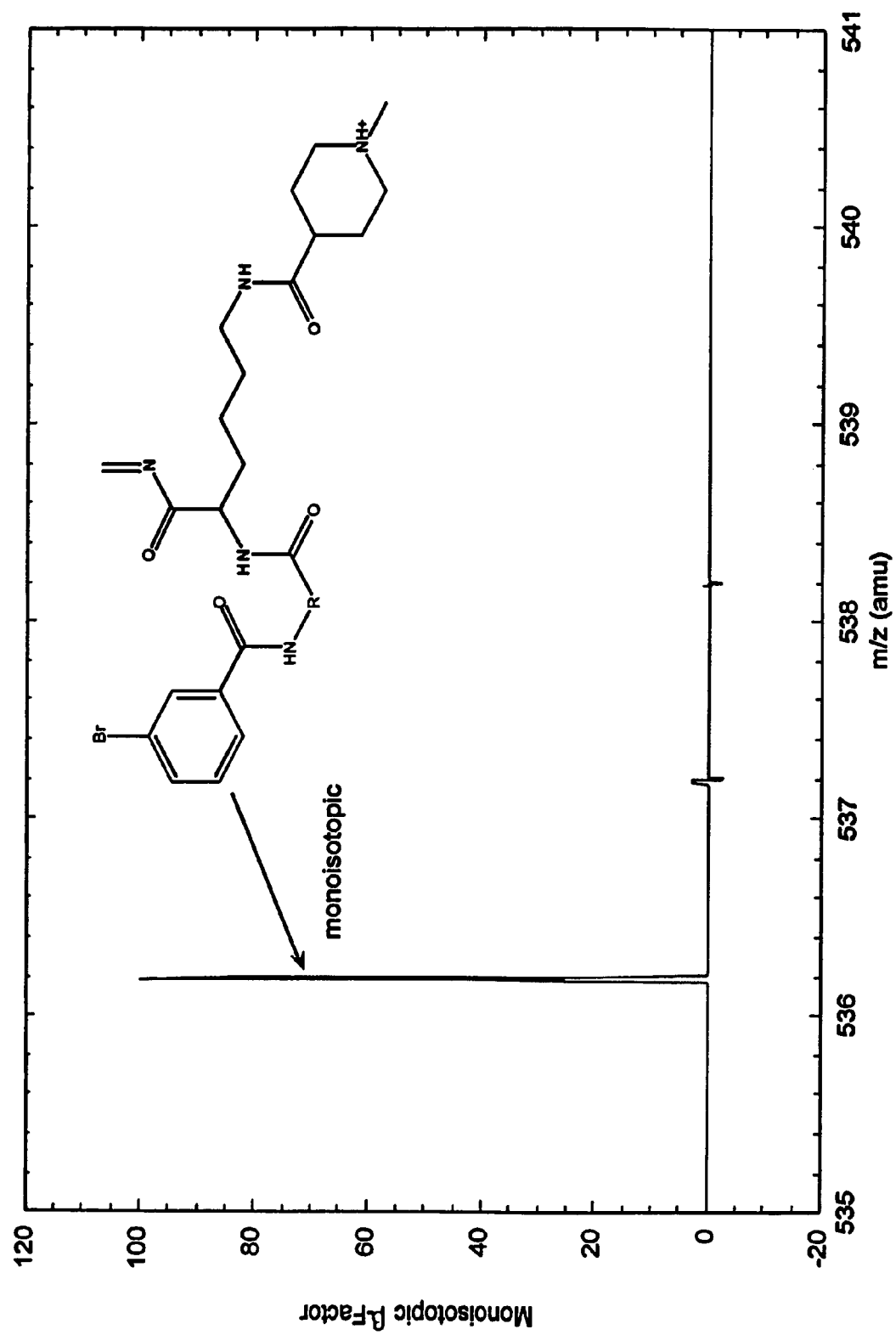
FIG. 11C shows the isotope-resolved mass spectrum.

The relative abundance of the lower mass peak was replaced with the β-factor from this calculation. The resulting deconvolved and peak-qualified mass spectra of the mass tag region are shown in FIG. 11B. Finally, the isotope series in the β-Factor spectrum (FIG. 11C) was further deconvolved to a single monoisotopic peak using algorithms generally known in the art as implemented in the BioSpec Data Explorer software (version 4.0, Applied Biosystems, Framingham, Mass.).

Example 7

This example illustrates the conjugation of a mass-defect label, the N-hydroxysuccinimide (NHS) ester of 5-bromonicotinic acid, to horse apomyoglobin (Myo).

Myo (sequencing grade) (Cat #A8673), 5-bromonicotinic acid (5-BrNA) (Cat # 228435), sodium dodecyl sulfate (SDS) (Cat # L6026), and urea (Cat # U0631) were purchased from Sigma-Aldrich and used as supplied. Anhydrous dimethylsulfoxide (DMSO) (Cat # 20864), 1-ethyl-3-(3-dimethylaminopropyl)-carbodiimide hydrochloride (EDC) (Cat # 22980)), and NHS (Cat # 24500) were purchased from Pierce and used as supplied.

The NHS-ester of 5-BrNA was prepared in situ by dissolving 20.8 mg 5-BrNA, 52.7 mg NHS, and 154.1 mg EDC in 0.657 mL DMSO. The sample was briefly sonicated in a bath sonicator to quickly dissolve all the solids. The mixture was incubated overnight at 4° C. Mass spectral analysis of the resulting mixture indicated 93% conversion of the 5-BrNA into the NHS ester (NHS-5-BrNA) by standard addition.

Myo was denatured by heating at 95° C. for 20 min at a concentration of 5.35 mg/mL in 5% (w/v) aqueous SDS solution. After cooling to ambient temperature, Myo was diluted to 1.07 mg/mL in 80 mM sodium phosphate buffer, pH 7.0, containing final concentrations of 1% (w/v) SDS and 6.4 M urea. Myo was labeled with NHS-5-BrNA by adding 0.353 mL (50 μmol) NHS-5-BrNA prepared as described above to 2 mL (2.14 mg) of the denatured myoglobin. The sample was incubated overnight at ambient temperature in the dark. The sample was then extensively dialyzed with 50% (v/v) aqueous acetic acid to remove urea and SDS, which has a deleterious effect on electrospray mass spectral analysis. Loss of protein was evident during the extensive dialysis but was not quantified. After the final dialysis, the sample was dried to completion in a speed vac (Savant).

Example 8

This example illustrates the generation of sequencing mass spectral fragment ion species from 5-BrNA labeled myoglobin (prepared as described in Example 7) by IMLS that are shifted from the periodic chemical noise.

A sample was prepared for mass spectrometry by dissolving the dried 5-BrNA labeled myoglobin (Example 7) in 0.1 mL of a 50% aqueous acetonitrile solution containing 1% by volume acetic acid. The labeled protein was subjected to in-source fragmentation in an electrospray-time-of-flight mass spectrometer (Mariner™, PE Biosystems, Inc.) as described by Schneider et al. (WO 00/63683, Oct. 26, 2000). The mass spectrometer settings were optimized and the instrument was calibrated immediately prior to injecting the sample according to the manufacturer's instructions. The sample was infused continuously via a 50 μm I.D. capillary into the electrospray source at a rate of 1 μL/min. The nozzle potential was set at 300 V to induce in-source fragmentation. Spectra were accumulated and summed for 345 s in the range of 50–2000 mass-to-charge units.

Figure 12A:
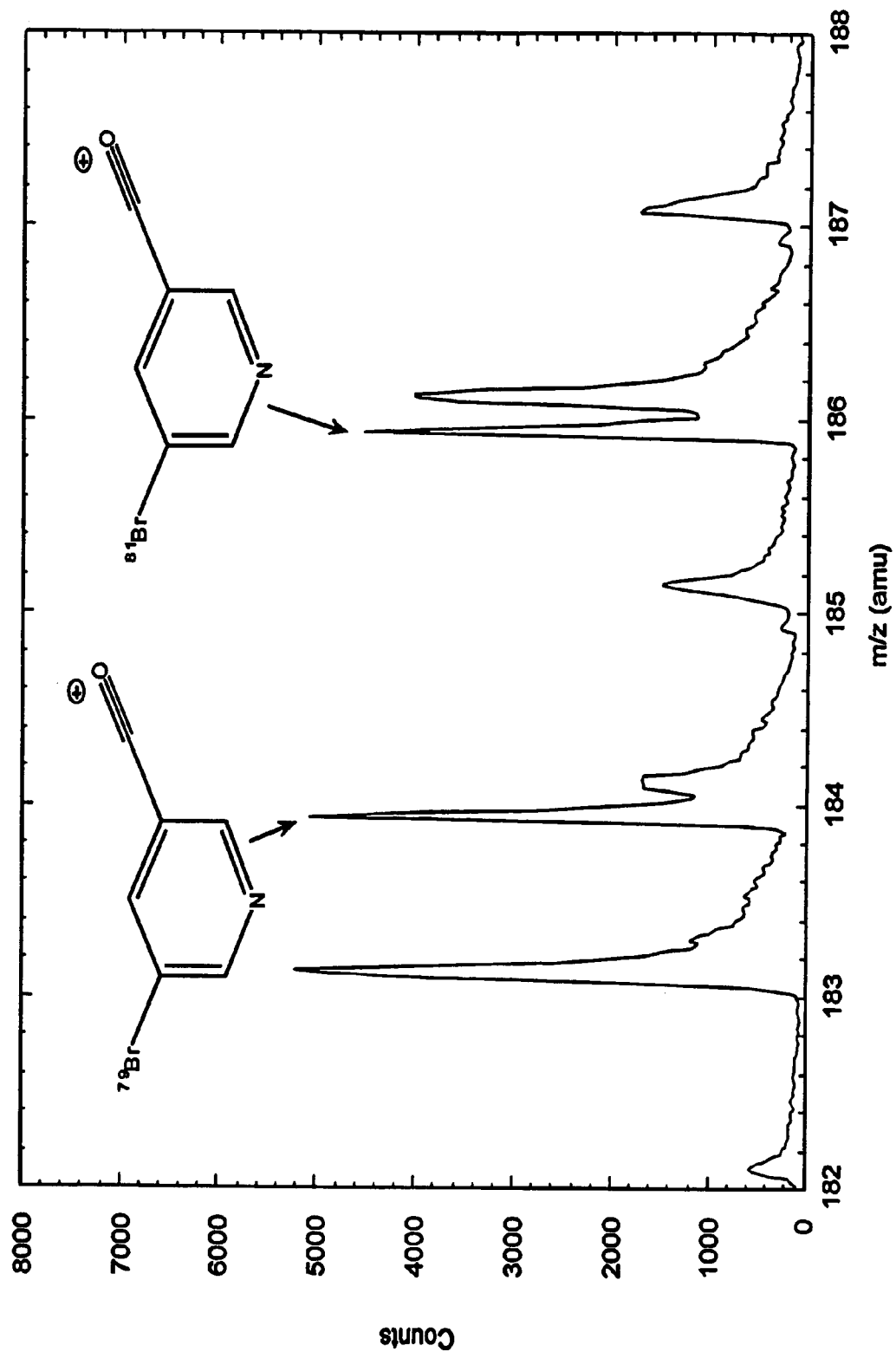
FIG. 12A shows the resolution of b-ion fragments from other chemical noise in the mass spectrum.

Examination of the raw mass spectral data showed clear evidence of the singly-charged b-type ion of the label itself (monoisotopic mass 183.94) that is shifted ~0.15 amu to the left of peaks that are part of the periodic chemical noise appearing on a period of ~1 amu (see FIG. 12A). The identity of this peak is corroborated by the appearance of a second peak (185.94) that is ~2 amu upstream of the first peak, which corresponds to the labeled fragment ion that incorporates the higher-mass isotope of bromine ($^{81}$Br). The relative intensities of these two peaks are nearly equivalent, reflecting the ~1:1 natural abundance of bromine isotopes.

This illustrates the utility of generating label-specific fragment ions incorporating mass defect elements (e.g., bromine) that can be resolved from chemical noise generated from proteins (which are composed of elements that do not exhibit strong mass defects) during IMLS.

Figure 12B:
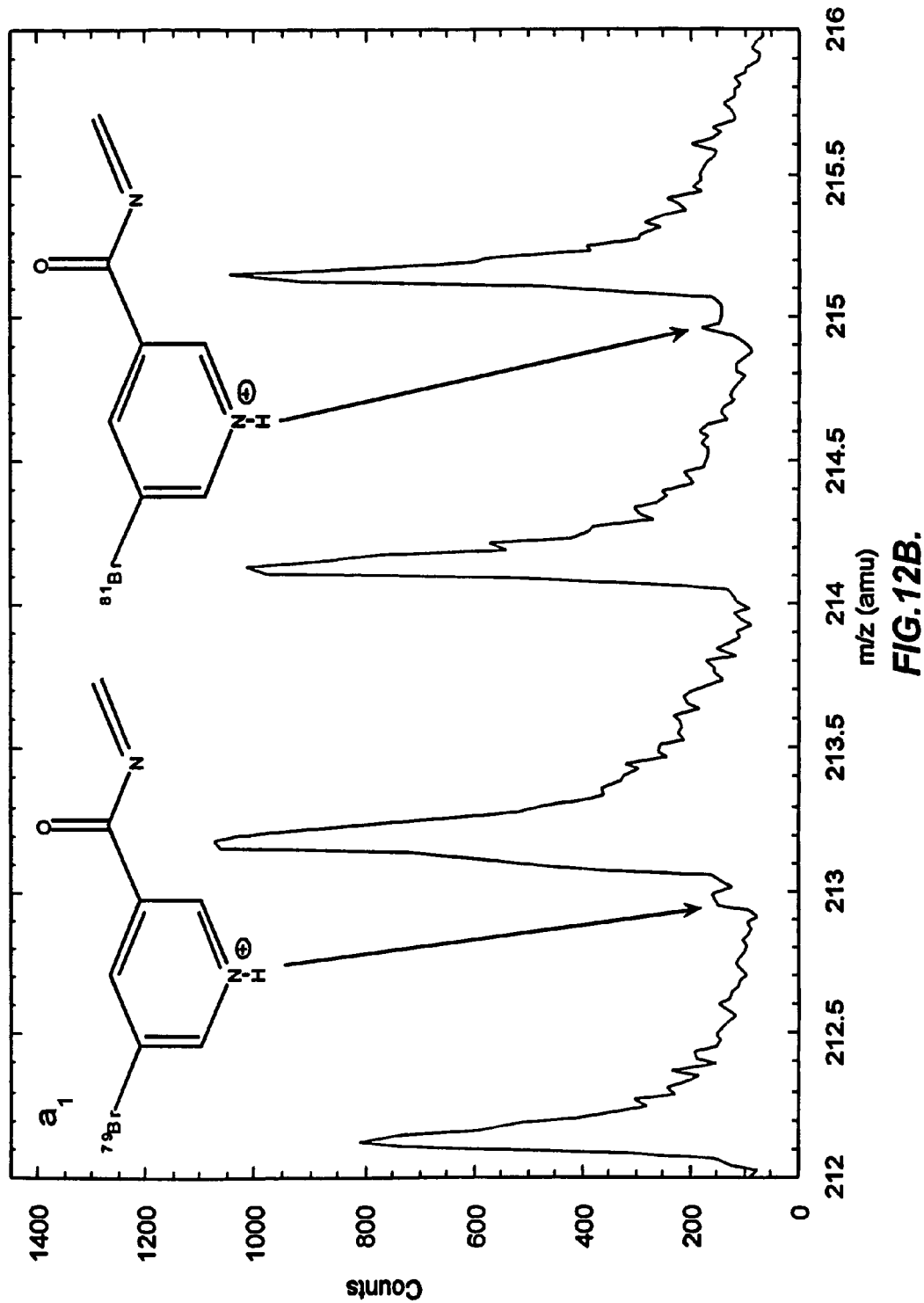
FIG. 12B shows the resolution of a-ion fragments from other chemical noise in the mass spectrum.
Figure 12C:
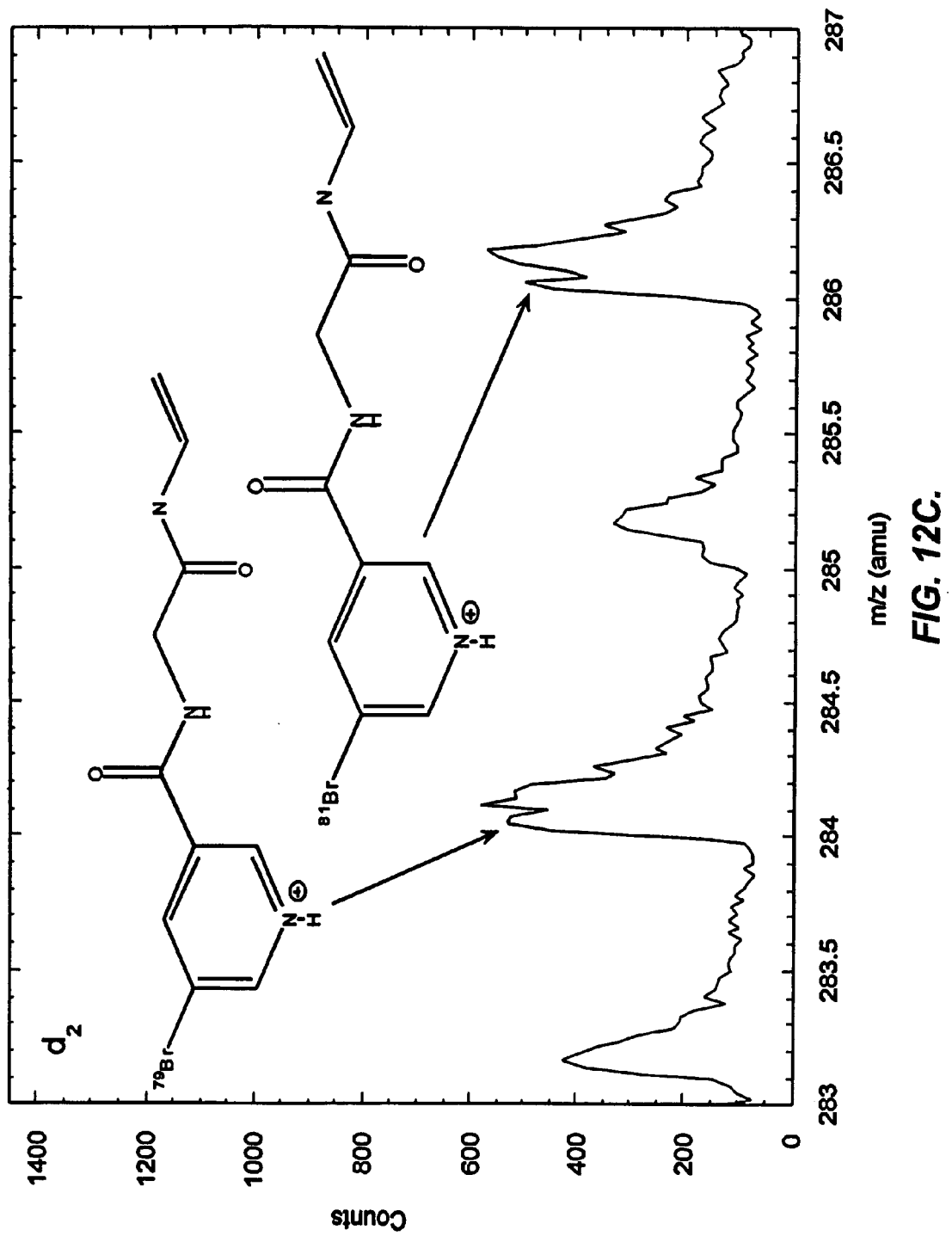
FIG. 12C shows the resolution of d-ion fragments from other chemical noise in the mass spectrum.

The spectral data were examined for evidence of mass defect-shifted peaks that correspond to fragment ions of the myoglobin N-terminus. The singly-charged $a_1$ ion doublet (glycine) is apparent at 212.97 and 214.96 m/z (see FIG. 12B). Furthermore, a doublet corresponding to the calculated masses of the $d_2$ ion (glycine-leucine) (284.05 and 286.05 m/z) is apparent (see FIG. 12C). Thus, sequencing ions are generated. The generally low abundance of sequencing ion peaks observed with this label is a result of the high intensity of the ion generated of the label itself which is highly stabilized by conjugation of the label carbonyl with the pydridyl ring (see FIG. 12A). Generation of this highly conjugated species will lead to preferential cleavage of the label amide linkage over the protein amide backbone, leading to a loss of significant sequencing ions. As a result, it would be preferable to separate the label carbonyl from the aromatic ring by one or more methylene groups to make the label amide linkage of similar bond energy to that of the protein amide backbone.

Example 9

This example illustrates the conjugation of a mass-defect label, the N-hydroxysuccinimide (NHS) ester of 5-bromo-3-pyridylacetic acid (5-Br-3-PAA), to horse apomyoglobin (Myo).

5-Br-3-PAA (Cat # 13579) was purchased from Lancaster Synthesis and used as supplied. Myo (sequencing grade) (Cat #A8673), sodium dodecyl sulfate (SDS) (Cat # L6026), and urea (Cat # U0631) were purchased from Sigma-Aldrich and used as supplied. Anhydrous dimethylsulfoxide (DMSO) (Cat # 20864), 1-ethyl-3-(3-dimethylaminopropyl)-carbodiimide hydrochloride (EDC) (Cat # 22980)), and NHS (Cat # 24500) were purchased from Pierce and used as supplied.

The NHS-ester of 5-Br-3-PAA (NHS-5-Br-3-PAA) was prepared in situ by dissolving 12.7 mg 5-Br-3-PAA, 7.4 mg NHS, and 12.5 mg EDC in 0.235 mL DMSO. The mixture was incubated for 24 h at ambient temperature in the dark. Mass spectral analysis of the resulting mixture indicated 53% conversion of the 5-Br-3-PAA by standard addition. Since conversion was not near completion, additional NHS (7.2 mg) and EDC (7.5 mg) were added and incubated for another 24 h. Mass spectral analysis of the resulting mixture after this second incubation period indicated 93% conversion of the starting material.

Myo was denatured by heating 1.89 mg in 0.54 mL 5% (w/v) aqueous SDS solution at 95° C. for 20 min. After cooling to ambient temperature, 1.89 mL of 9M urea in 20 mM sodium phosphate buffer, pH 7.0, was added to the sample. NHS-5-Br-3-PAA (0.24 mL, ~19 mM final concentration) was added to the denatured myoglobin. The sample was incubated overnight at ambient temperature in the dark. The reaction mixture was spin dialyzed against 25 mM Tris, pH 8.3 buffer containing 0.1% (w/v) SDS to remove urea and NHS-5-Br-3-PAA reaction by-products. The final retentate (~0.6 mL) containing the labeled myoglobin was subjected to a chloroform extraction procedure to remove bound SDS (Puchades et al. (1999), *Rap. Comm. Mass. Spec.* 13, 344–349). To the sample, 2.4 mL methanol, 0.6 mL chloroform, and 1.8 mL water were added. The sample was mixed by inverting the tube once. The sample was centrifuged (3743 g, 20 min, ambient temperature) to aid in phase separation, and most of the top layer was discarded. Methanol (1.8 mL) was added to the remaining lower phase and the protein that had precipitated at the interface. The tube was vortexed vigorously and the precipitated protein was pelleted by centrifugation (3743 g, 40 min, ambient temperature). The supernatant was decanted and discarded and the residual protein pellet was dried with a stream of nitrogen gas. The dried labeled Myo was resuspended in 0.4 mL 10% (v/v) aqueous acetic acid solution. The protein concentration (2.6 mg/mL) was measured by BCA assay using BSA as a standard.

Example 10

This example illustrates the generation of sequencing mass defect spectral fragment ion species from 5-Br-3-PAA labeled myoglobin (prepared in Example 9) by IMLS that are shifted from the periodic chemical noise.

A sample was prepared for mass spectrometry by dissolving 5-Br-3-PAA labeled myoglobin (150 µg) in 0.5 mL of a 50% aqueous acetonitrile solution containing 1.2% by volume acetic acid. The labeled protein was subjected to in-source fragmentation in an electrospray-time-of-flight mass spectrometer (Mariner™, PE Biosystems, Inc.) as described by Schneider et al. (WO 00/63683, Oct. 26, 2000). The mass spectrometer settings were optimized and the instrument was calibrated immediately prior to injecting the sample according to the manufacturer's recommendations. The sample was infused continuously via a 50 µm I.D. capillary into the electrospray source at a rate of 1.2 µL/min. The nozzle potential was set at 225 V to induce in-source fragmentation. Spectra were accumulated and summed for 180 s in the range of 50–2000 mass-to-charge units.

Figure 13A:
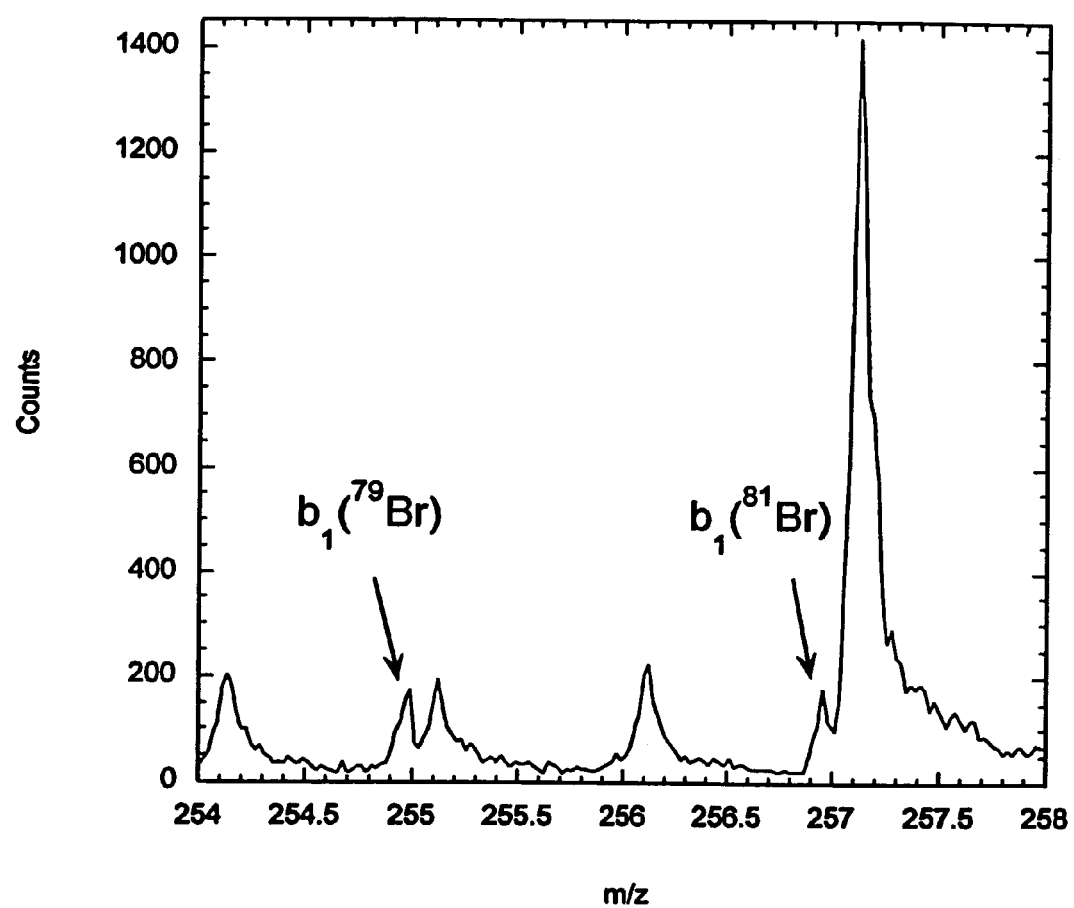
FIG. 13A shows the doublets of bromine isotope pairs that are shifted from the periodic noise that correspond to masses of the single-charged b ion of the label.
Figure 13B:
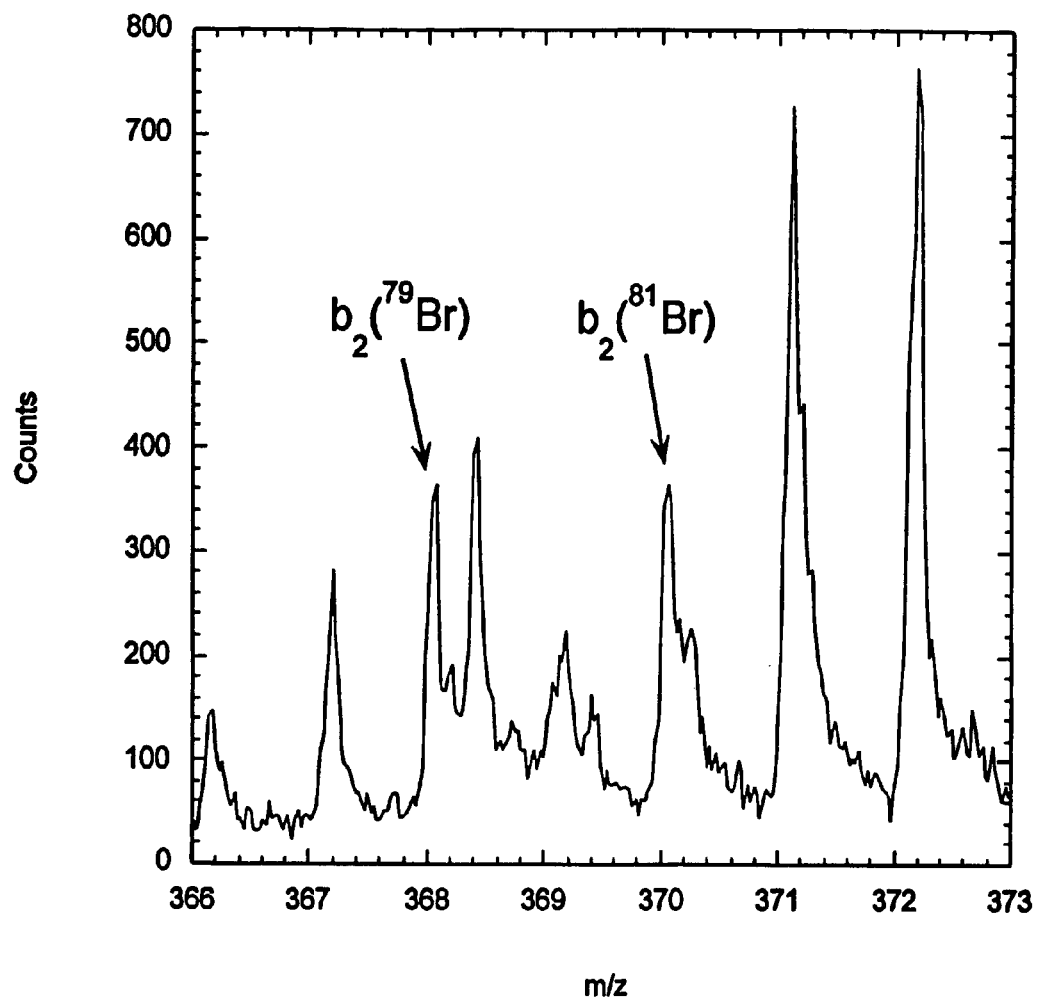
FIG. 13B shows the doublets of bromine isotope pairs that are shifted from the periodic noise that correspond to masses of the single-charged b1 ion of the N-terminus of labeled myoglobin.
Figure 14A:
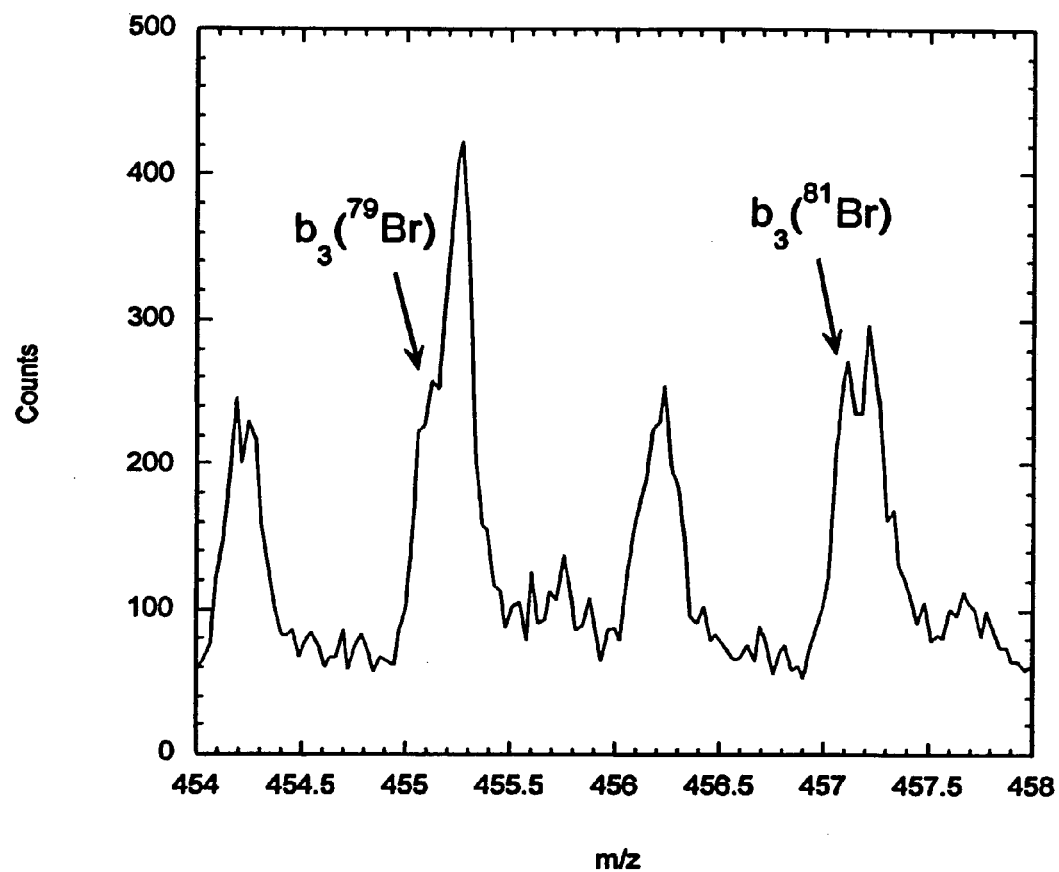
FIG. 14A and FIG. 14B shows the doublets of bromine isotope pairs that are shifted from the periodic species corresponding to the single-charged $a_1$ ion.
Figure 14B:
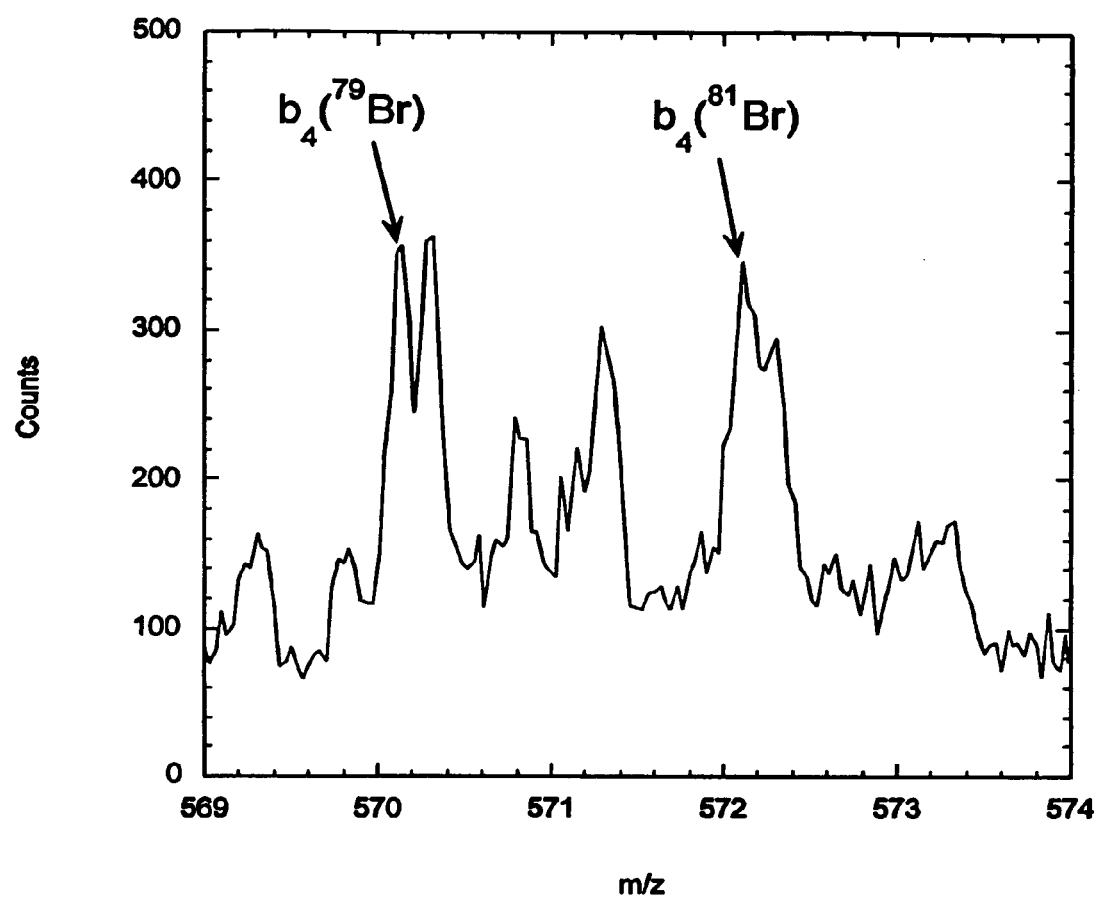
Figure 15A:
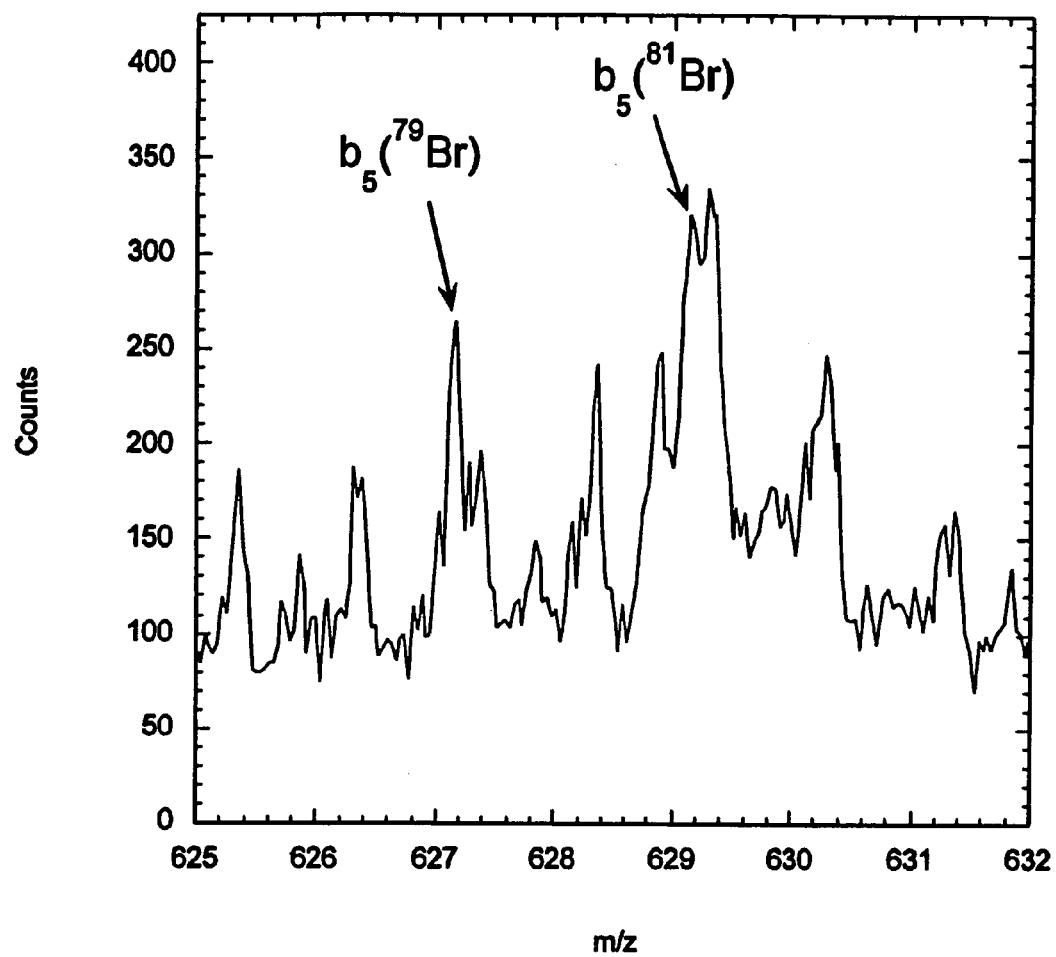
FIG. 15A and FIG. 15B shows the doublets of bromine isotope pairs that are shifted from the periodic species corresponding to the single-charged $d_{a2}$ ion.
Figure 15B:
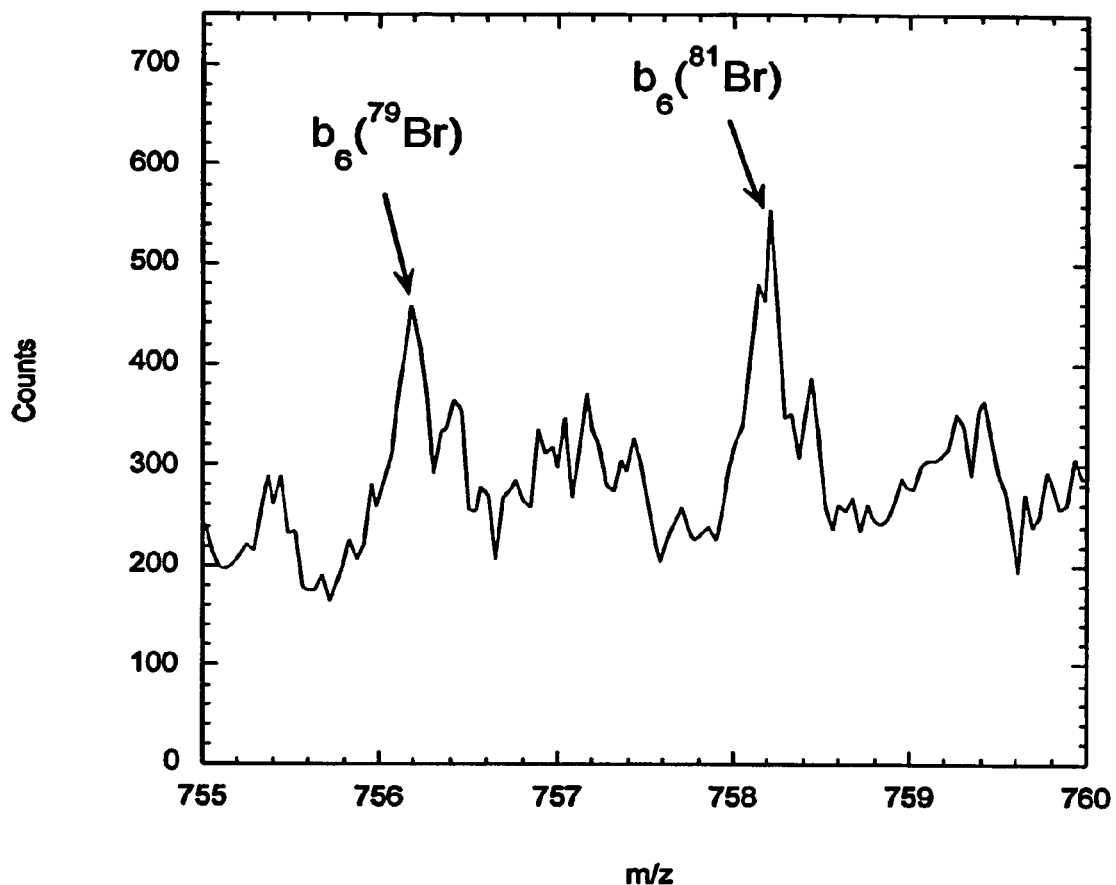

Examination of the raw mass spectral data shows clear evidence of the singly-charged $b_1$–$b_6$ ions derived from the N-terminus of the labeled myoglobin (FIGS. 13A–B, FIGS. 14A & B, and FIGS. 15A & B). Doublet peaks that correspond to b ions incorporating either $^{79}$Br or $^{81}$Br atoms (reflecting the ~50:50 natural abundance of bromine) are shifted by their mass defect (~0.15) to the left of the chemical noise that is apparent on a periodic frequency of ~1 amu. Thus, unlike the limited sequencing ions that were produced by the 5-BrNA labeled myoglobin (discussed in Examples 1 and 2), this labeled myoglobin, with an intervening methylene unit between the label carbonyl and the pyridine ring, produces a complete mass ladder of b ions through the first six N-terminal residues. This is most likely a result of the amide linkage of 5-Br-3-PAA being more similar to the protein backbone amide linkages in terms of cleavability compared to that of 5-BrNA, which appears to be more susceptible to cleavage.

Example 11

This example describes one method for the IMLS of apomyoglobin labeled with 4-bromobenzaldehyde.

N-terminal labeling of proteins with aldehydes followed by stabilization with reducing agents results in labels with secondary amine attachments. This attachment is more energetically stable than the corresponding amide. Therefore, during IMLS, the label should show minimal fragmentation compared to the peptide amide bonds and thus should produce more abundant fragment ions of interest. In addition, the generation of a basic site directly from the chemistry provides a "soft" charge moiety that renders the incorporation of a charged moiety in the label before attachment unnecessary.

4-Bromobenzaldehyde is available from Sigma-Aldrich. The aldehyde can be added to an aqueous buffered solution of denatured myoglobin in a manner similar to the conditions described in Example 10 for labeling of myoglobin with the NHS ester of 5-bromonicotinic acid. Upon reaction completion, the labeled myoglobin is stabilized by reduction of the generated imines with sodium cyanoborohydride. This reducing agent selectively reduces imine-like double bonds and does not reduce other functional groups commonly found in peptides and proteins. The resulting label chemical linkage is a secondary amine. The labeled protein is then purified by dialysis or gel filtration. The labeled protein is dissolved in an MS compatible buffer system and IMLS is performed in the manner as described in Example 10.

Example 12

This example illustrates the IMLS of ubiquitin labeled with 5-bromonicotinic acid.

Ubiquitin is labeled with 5-bromonicotinic acid according to the procedure outlined in Example 7 for apomyoglobin. Labeled ubiquitin is subjected to in-source fragmentation in the mass spectrometer as described in Example 8, and the spectra are analyzed for the presence of N-terminal fragment ions containing the label.

Example 13

This example illustrates the IMLS of Apomyoglobin labeled with 6-Bromo-2-hydroxy-quinoline-4-carboxylic acid (BHQC)

The NHS ester of BHQC is prepared according to the procedure described in Example 7 for preparing the NHS ester of 5-bromonicotinic acid. Apomyoglobin is labeled with BHQC using a procedure similar to that described in Example 7. Labeled apomyoglobin is subjected to in-source fragmentation in the mass spectrometer as described in Example 10. The mass spectral data are analyzed for labeled N-terminal fragment ions.

Example 14

This example illustrates the IMLS of ubiquitin labeled with 6-bromo-2-hydroxy-quinoline-4-carboxylic acid (BHQC).

Ubiquitin can be labeled with BHQC according to the procedure outlined in Example 13 for apomyoglobin. Labeled ubiquitin is then subjected to in-source fragmentation in the mass spectrometer as described in Example 10. The mass spectral data are subsequently analyzed for labeled N-terminal fragment ions.

Example 15

This example illustrates the use of the automated deconvolution and sequencing algorithms of this invention to find the N-terminal sequence of 5-Br-3-PAA-labeled myoglobin fragmented in-source in an ESI-TOF mass spectrometer as described in Example 5.

Figure 16:
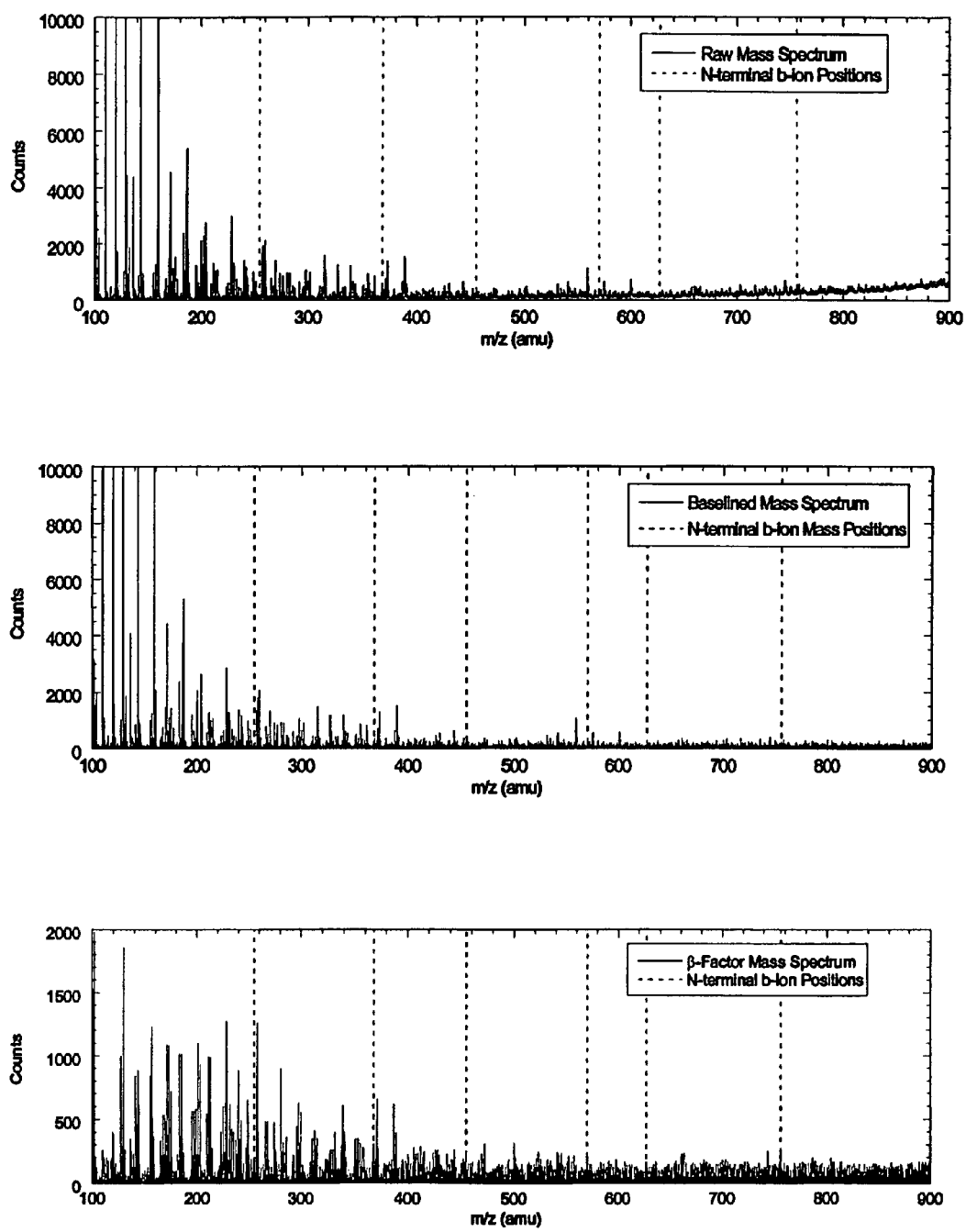
FIG. 16 shows the raw, baselined, and β-factor mass spectrum of 5-Br-3-PAA-labeled myoglobin fragmented in-source in an ESI-TOF mass spectrometer.

The raw data used to generate the mass spectrum from Example 5 is exported in ASCII format from the data acquisition system. The natural period of the chemical noise is determined from this raw data using the "deconvolver" code shown in the appendix and is determined to be 1.000575 amu. Using this natural period the spectrum is baselined (output file *.bsl) to correct for instrument error, which is always positive in MS (FIG. 16). Baselining means that the minimum data value in each 1.000575 amu block of data is adjusted to zero by subtracting through every data point in the block of data. The baselined data file is subsequently processed with the "betafactor" as a way to qualify mass defect (Br-containing) peaks, which should always have a matching [$^{81}$Br] peak 1.997954 amu upstream from the [$^{79}$Br] peak (FIG. 16). The resulting *.bfc file is then processed through the "sequencer" code (see, co-pending application Ser. No. 60/242,398 filed Oct. 19, 2001, entitled "Methods for Determining Protein and Peptide Terminal Sequences", the disclosure of which is incorporated herein by reference), with the true N-terminal myoglobin sequence (5-Br-3-PAA-GLSDGE; SEQ ID NO:1) being the top ranked solution through the first four residues. In this example the "sequencer" code was limited search for the first charge state of b-ions.

Figure 17:
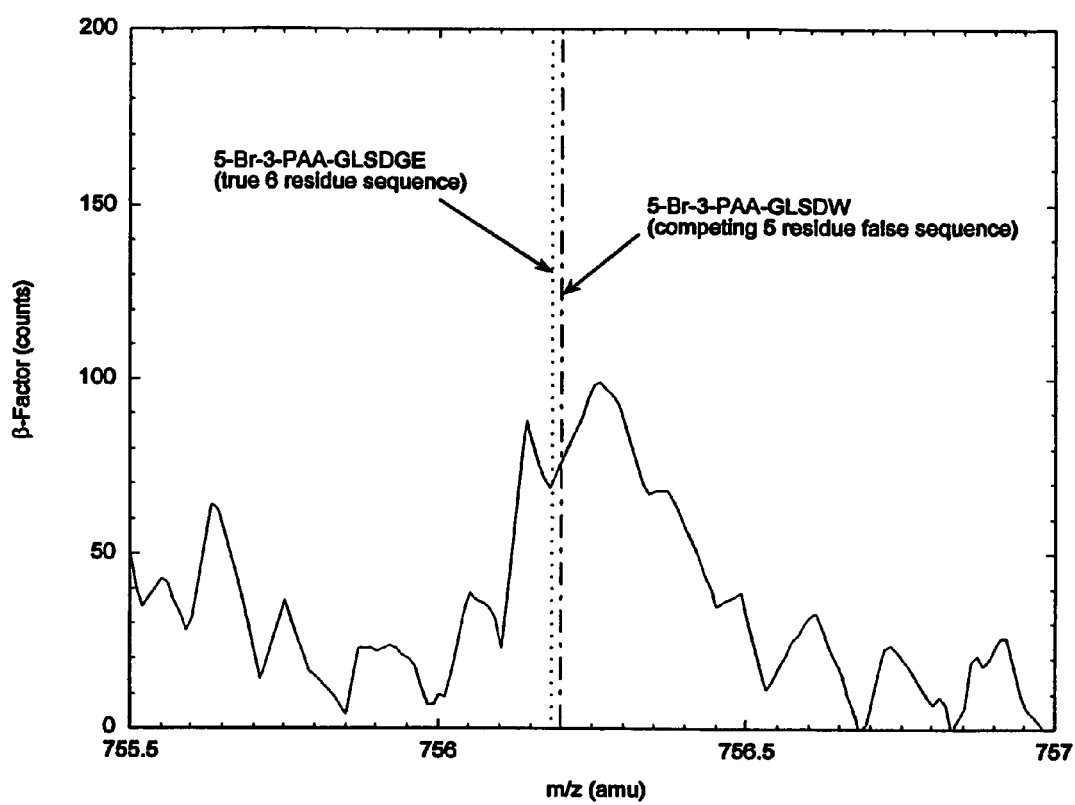
FIG. 17 shows the result of using "sequencer" code to determine the sequence of the first five residues in 5-Br-3-PAA-labeled myoglobin (SEQ ID NOS:1 and 2).

When the "sequencer" code is run to determine the sequence of the first five residues, the sequence GLSDW (SEQ ID NO:8), which yields a theoretical mass of 756.1993 overlaps (FIG. 17) the peak corresponding to the mass defect position of the sixth residue of the true sequence (GLSDGE (SEQ ID NO:9) at 756.1840). This results in GLSDW (SEQ ID NO:8) being the top ranked sequence at five residues. However, when "sequencer" is run through six residues the true sequence GLSDGE (SEQ ID NO:9) becomes top ranked again because GLSDW (SEQ ID NO:8) fails to propagate a competing sequence at the sixth residue. This shows the advantage of a cumulative probability algorithm.

Example 16

Figure 18A:
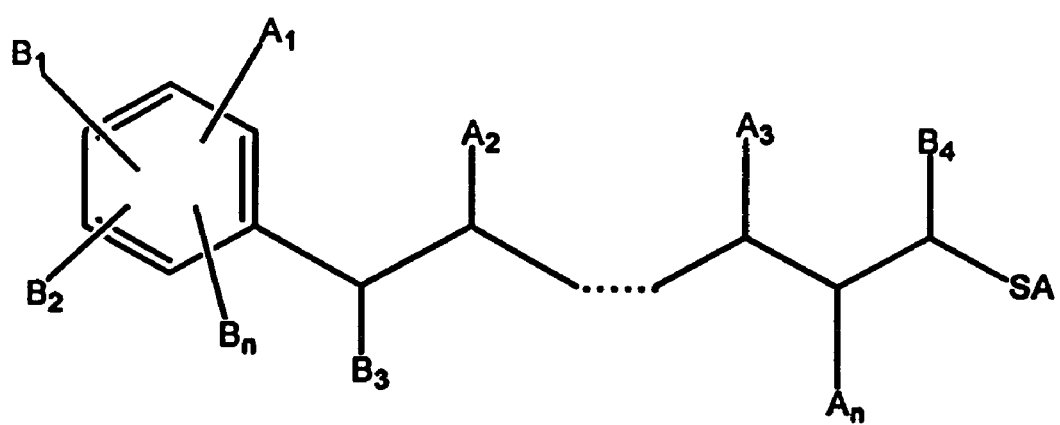
FIG. 18 illustrates a general formula for a mass defect label containing a combination of ionizable groups ($A_1 \ldots A_n$), mass defect elements ($B_1 \ldots B_n$), and a core succinic anhydride reactive moiety (SA) (FIG. 18a) as well as an overall synthetic scheme for a $\{(A_1 \ldots A_n)\text{-}(B_1 \ldots B_n)\text{-}SA\}$ mass defect label (FIG. 18b).

This example illustrates the synthesis of a generic mass-defect label that incorporates a mass-defect element of this invention (i.e., bromine), an ionizable group (i.e., pyridyl) and a succinic anhydride linking moiety for attachment to the N-terminus or other desired primary or secondary amino group of a polypeptide or other species. It has been demonstrated that succinic anhydride, and ostensibly its derivatives, react with nearly quantitative efficiency towards polypeptide amino groups (see, Munchbach et al., *Anal. Chem.* 72: 4047–4057 (2000)). Other comparable aliphatic/aromatic species can be readily synthesized that contain any combination of ionizable groups ($A_1 \ldots A_n$), mass defect elements ($B_1 \ldots B_n$), and a core succinic anhydride reactive moiety (SA) (see FIG. 18a).

Figure 18B:
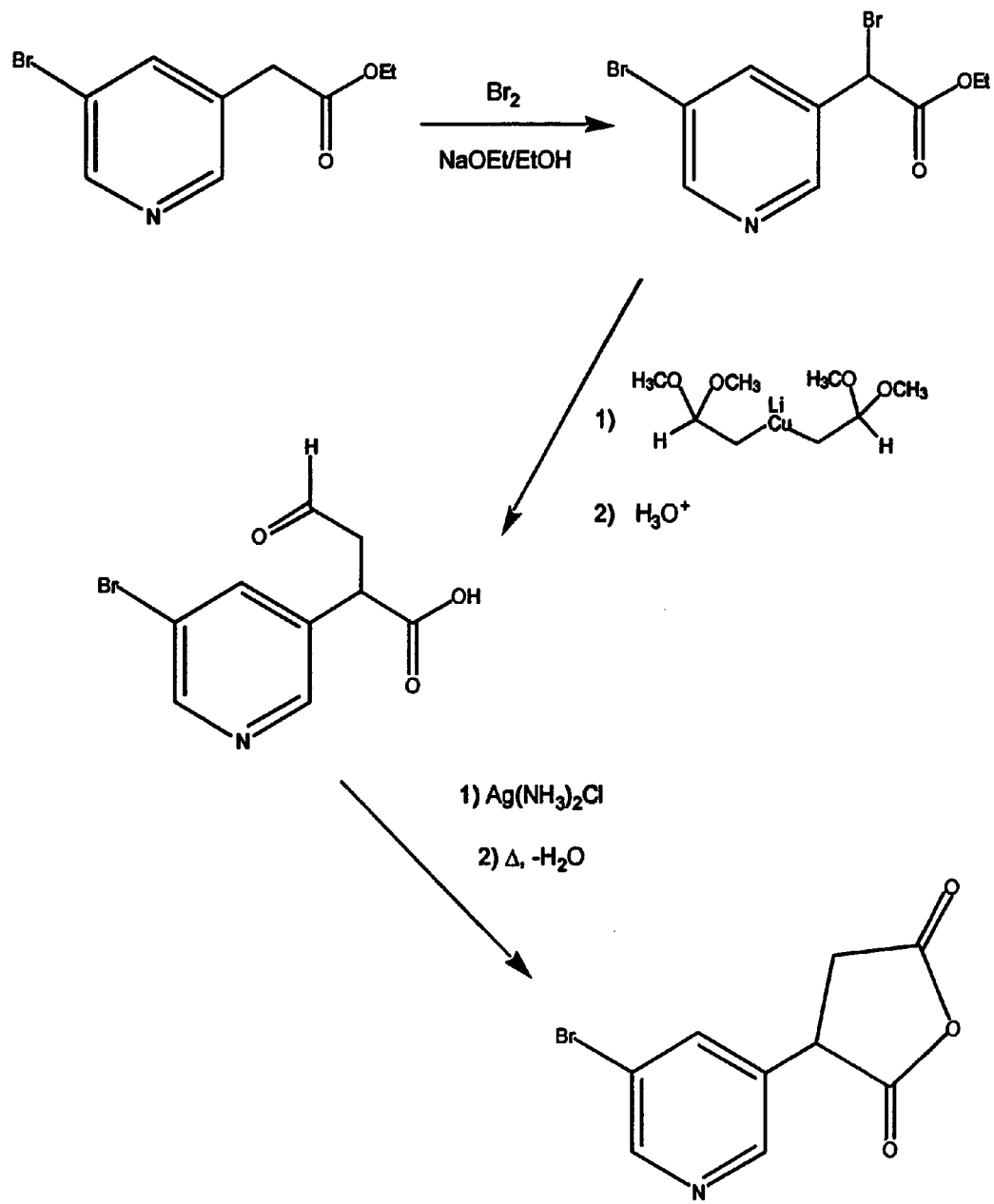

As an exemplary strategy, FIG. 18b outlines an overall synthetic scheme for a {($A_1 \ldots A_n$)-($B_1 \ldots B_n$)-SA} mass defect label. In this scheme, 5-bromo-3-pyridyl acetic acid (Lancaster, Cat #13579) is initially converted to the ethyl ester by reaction with ethanol in the presence of an acid catalyst with removal of water. The resulting ester is then α-brominated by reaction with elemental bromine in a basic solution of sodium ethoxide in ethanol. The brominated α-carbon is then selectively reacted in an anhydrous organic solvent such as tetrahydrofuran with lithium di-(bromoacetaldehyde dimethyl acetal)cuprate which is prepared by reaction of commercially-available bromoacetaldehyde dimethyl acetal (Aldrich, Cat #242500) with lithium to form the organolithium species that is converted into the cuprate by reaction with Cu(II)I. The resulting product is treated with aqueous acid to remove the acetal moiety and hydrolyze the ester back to the free acid. The liberated aldehyde is oxidized to the corresponding carboxylic acid by standard oxidizing agents (e.g., Ag$^+$), and the synthesis is completed by cyclization and dehydration of the two generated carboxylic acid groups to form the desired succininic anhydride derivative.

Example 17

Figure 19:
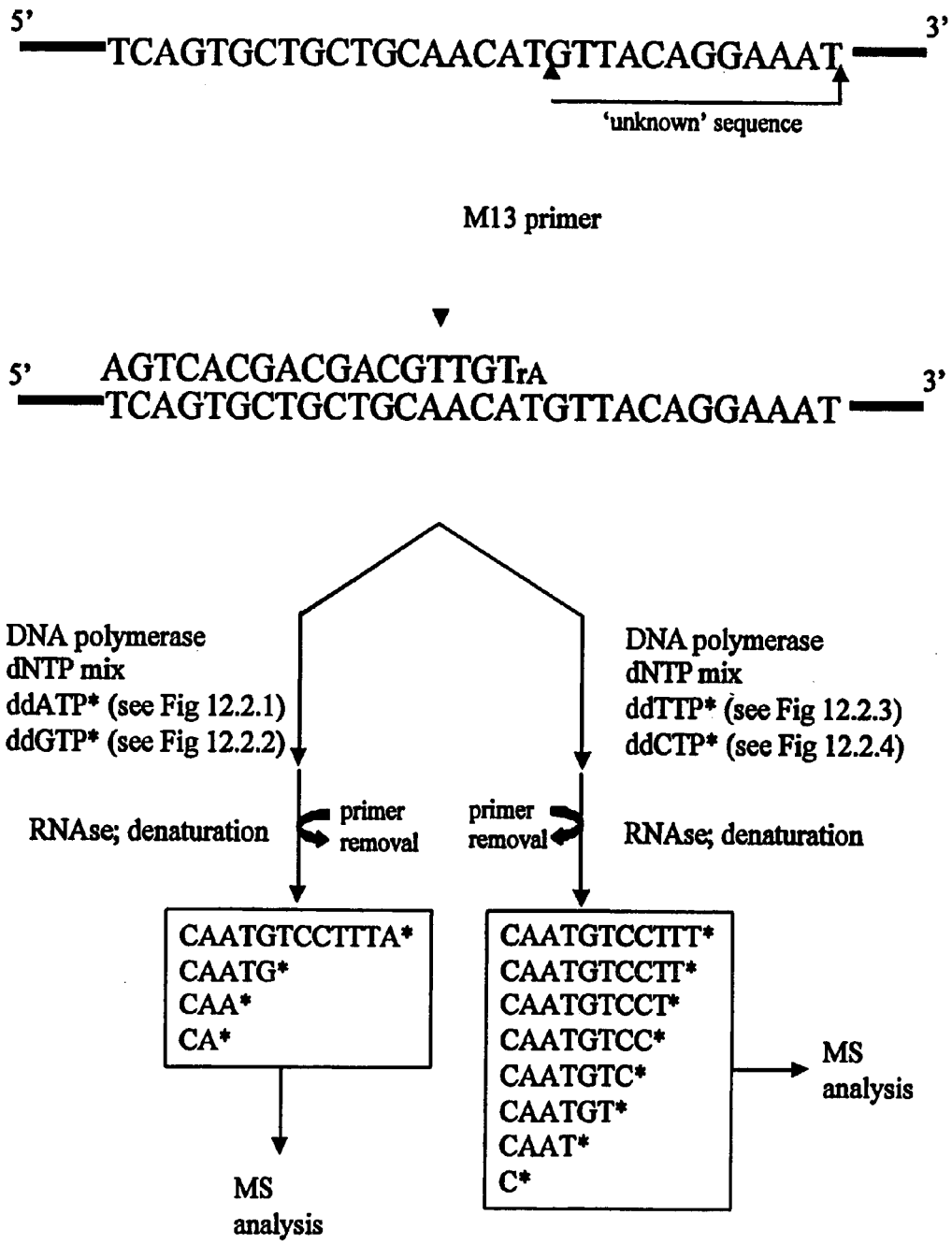
FIG. 19 illustrates an exemplary sequencing technique using the methods described by Sanger in combination with the labeling strategy provided herein (SEQ ID NOS:3–7).
Figure 20A:
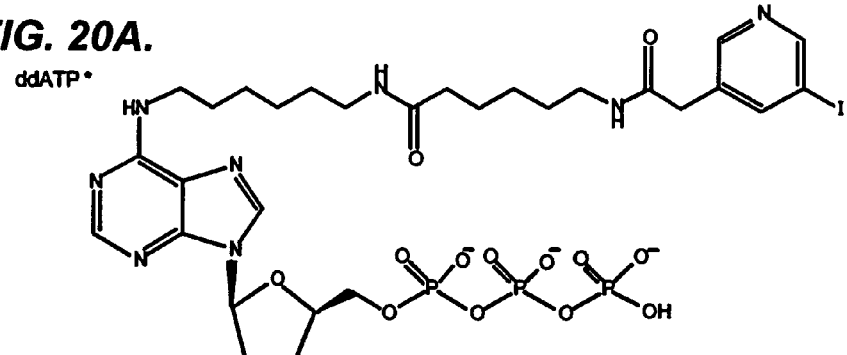
FIG. 20 illustrates labeled bases that can be used in the sequencing methods provided herein.
Figure 20B:
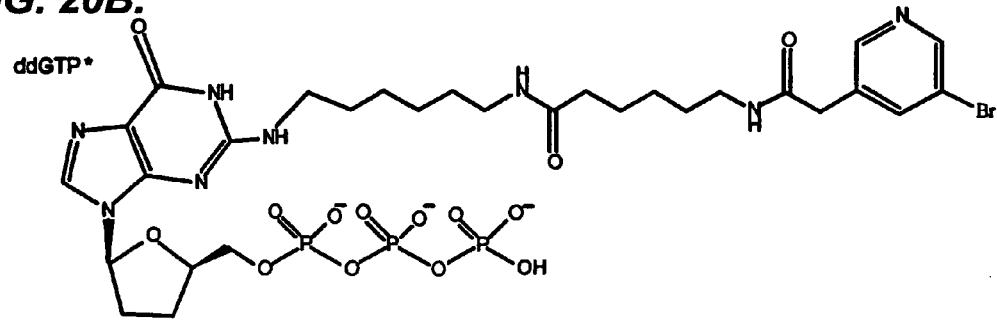
Figure 20C:
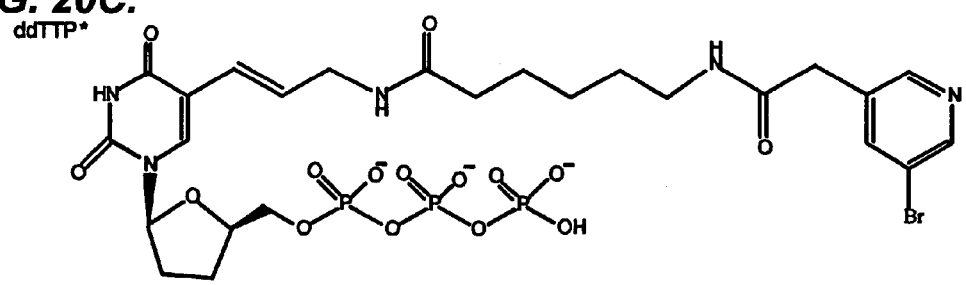
Figure 20D:
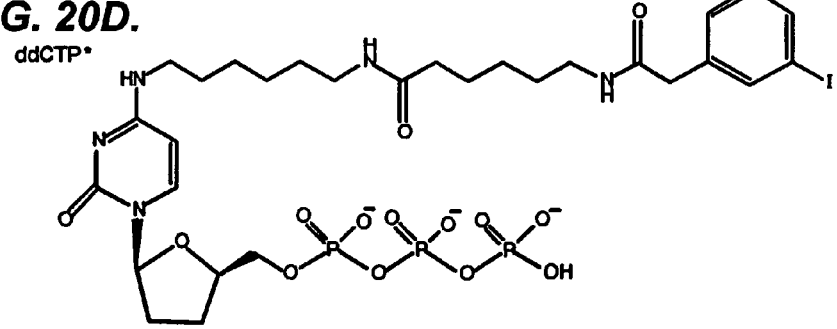

This example illustrates the use of mass defect labels in DNA sequencing applications. The scheme presented (FIG. 19) represents an exemplary sequencing technique using the method of Sanger; however, similar methodology could be applied to other DNA sequencing strategies such as Maxam-Gilbert or PCR or other strategies known to those skilled in the art.

Briefly, an M13 plasmid carrying a cloned unknown DNA sequence (e.g., d(GTTACAGGAAAT) (SEQ ID NO:10)) is initially hybridized with an M13 origin of replication primer (3'-d(AGTCACGACGACGTTGT)rA-5'; SEQ ID NO:4) that is labeled at the 5' end with rA to make the primer selectively cleavable by RNAse (Integrated DNA Technologies, Inc., Coralville, Iowa). The reaction volume is divided in half and transferred to two tubes. In one tube, polymerase, dNTPs, dGTP, and mass-defect-labeled ddATP* (see FIG. 20a) and ddGTP* (see FIG. 20b) are added. To the other tube, polymerase, dNTPs, and mass-defect-labeled ddTTP* (see FIG. 20c) and ddCTP* (see FIG. 20d) are added. The modified ddNTPs shown in FIG. 20 are exemplary and are prepared according to standard procedures (see, Kricka, L. J., NONISOTOPIC DNA PROBE TECHNIQUES, Academic Press, New York (1992); Keller, G. H. and Manak, M. M., DNA PROBES, Stockton, N.Y. (1989)). Many other modified ddNTPs are useful which contain purine and pyrimidine bases derivatized with mass defect label moieties and separated by a large assortment of crosslinkers with different lengths and/or compositions. DNA replication and chain extension is initiated by incubation at 37° C. Mass ladders are produced by chain termination with the ddNTPs. A denaturation and cleavage step with RNAse at the end of the reaction removes the chain-terminated product from the template and frees the primer that can be selectively removed by hybridization. The DNA fragments are dissolved in a mass spectrometer-compatible buffer and flown in an ESI-TOF mass spectrometer in negative ion mode. The peaks corresponding to a series of multiply-charged ions for each fragment are deconvolved using standard algorithms supplied by the instrument manufacturer (Applied Biosystems) to generate spectra containing only the zero-charge masses. The zero-charge spectra are subsequently centroided also using the instrument supplier's algorithms.

Figure 21:
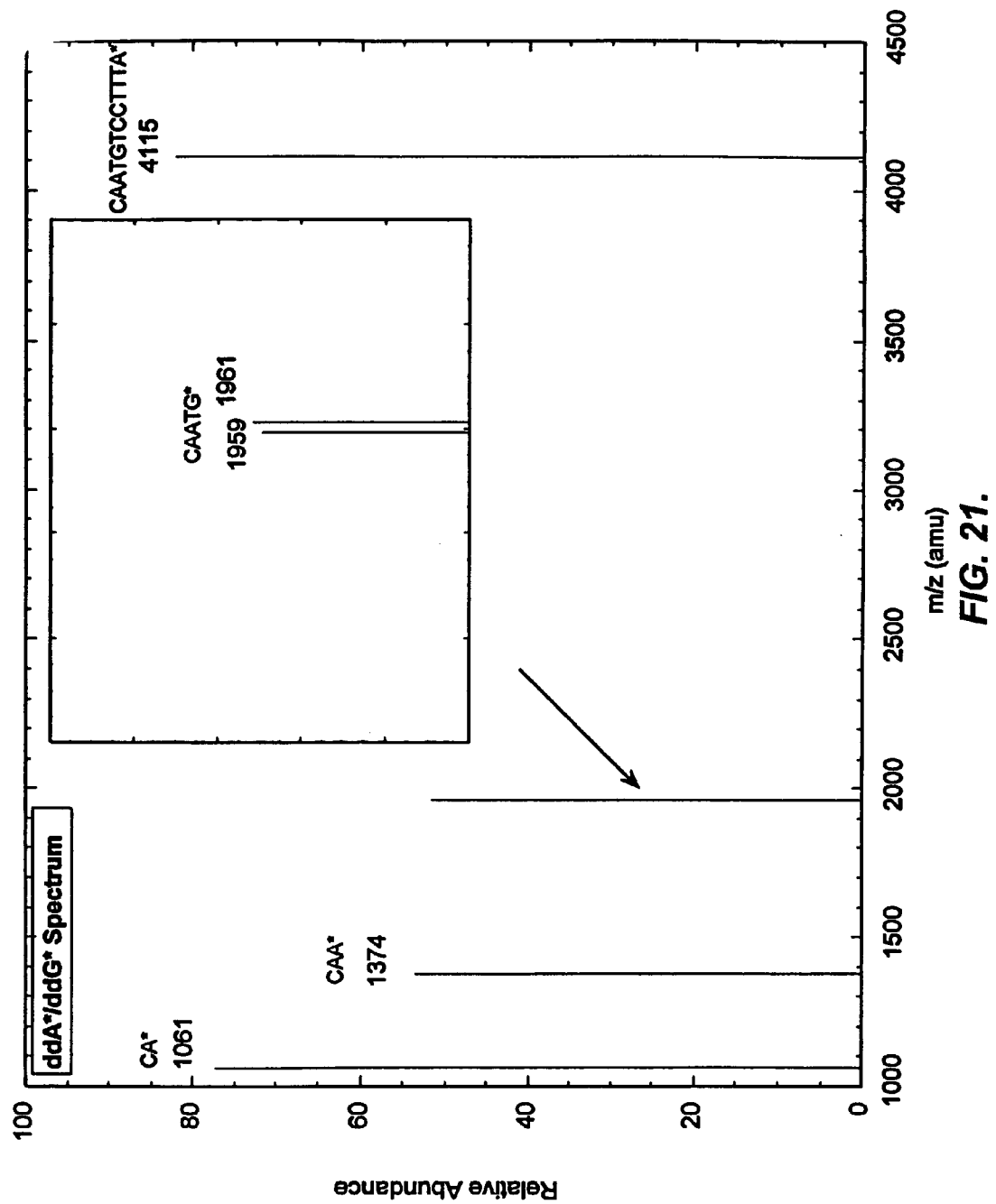
FIG. 21 illustrates a ddA*/ddG* mass spectrum (SEQ ID NO:5) (see Example 18).
Figure 22:
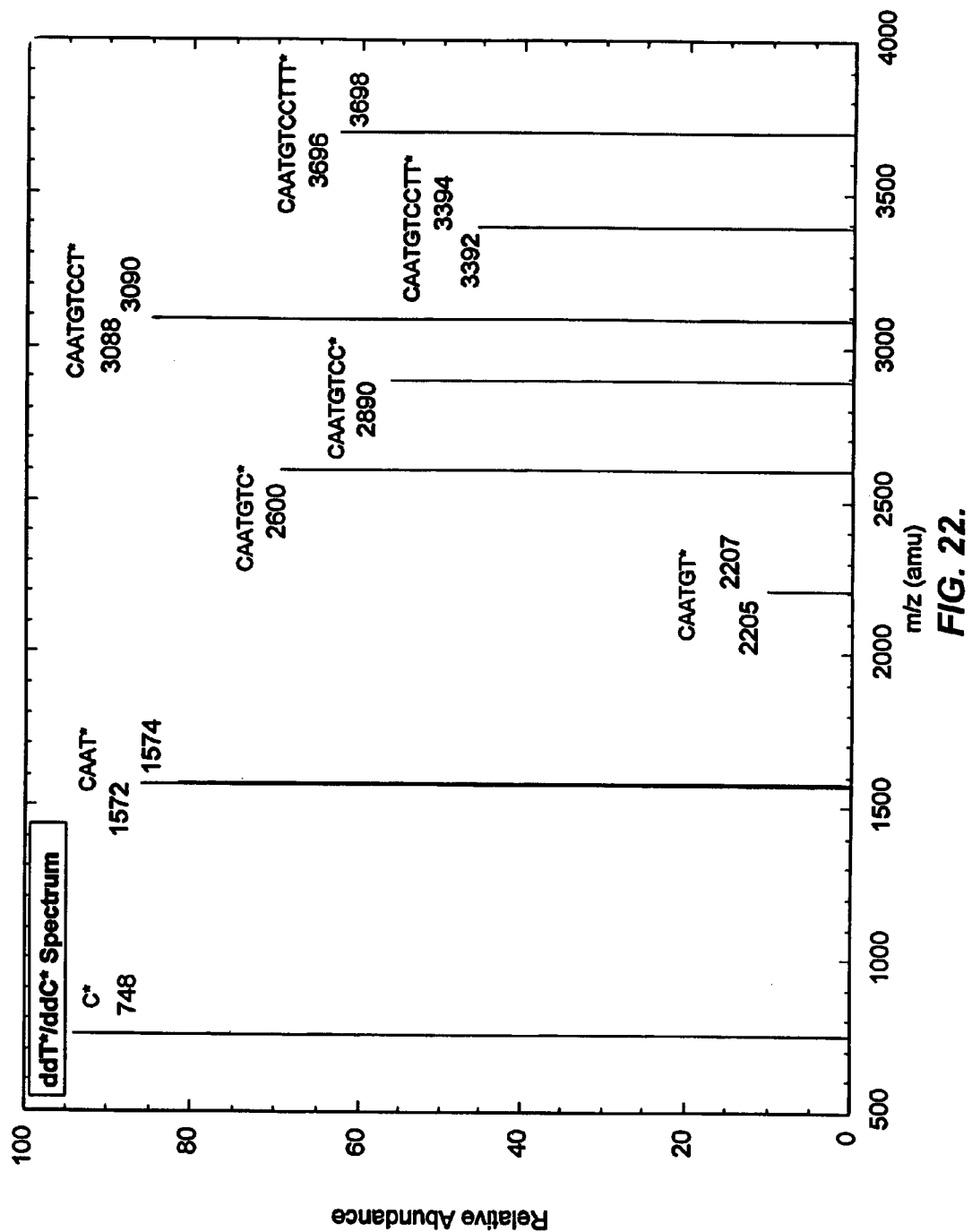
FIG. 22 illustrates a ddT*/ddC* mass spectrum (SEQ ID NOS:5 and 6) (see Example 18).

The mass spectral data are analyzed as follows. The spectrum from the ddA*- and ddG*-containing sample is deconvolved and chemical noise is eliminated, leaving only peaks that have incorporated bromine or iodine atoms (FIG. 21). The spectrum from the ddT*- and ddC*-containing sample is similarly treated (FIG. 22). Looking at both deconvolved spectra, the highest mass fragment is found (4114.733) in the ddA*/ddG* spectrum (FIG. 21). This fragment can also be identified as the fragment that contains an iodine mass element as there is no isotopic pair; therefore, the last nucleotide in the "unknown" sequence is A. The mass fragment with the next lower mass is a doublet at 3695.611 and 3697.609 which is found in the ddT*/ddC* spectrum (FIG. 22). The doublet indicates incorporation of a bromine atom, and, therefore, the next nucleotide in the sequence is T. This process is repeated until the last peak is found, in this case, a singlet peak at 748.1850 in the ddT*/ddC* spectrum corresponding, therefore, to C. Thus, the sequence ATTTCCTGTAAC (SEQ ID NO:11) is determined, and when inverted and the nucleotide complements are substituted, the "unknown" sequence GTTACAGGAAAT (SEQ ID NO:10) is determined.

In this example, a DNA segment of ~4000 MW is sequenced which is within the specifications for this invention. Since the ability to distinguish mass defect species incorporating one mass-defect atom degrades at masses over 5000, larger DNA segments than the example presented here can be sequenced by either using more mass defect elements in the terminating ddNTPs, or, alternatively, by using the method of the "rolling primer." With the "rolling primer" method, a shorter segment of the desired DNA to be sequenced is obtained using the above procedure, and a new primer is made from this deduced sequence to continue sequencing along the larger DNA strand. In the end, the shorter fragments can be placed end-to-end to reveal the sequence of the unknown DNA.

Example 18

In this example we use the mass defect label (5-Br-3-PAA) to sequence bovine ubiquitin (Sigma-Aldrich). Ubiquitin was labeled by the same procedure described in Example 7 for myoglobin, except that the protein labeling step was conducted in 100% acetonitrile. The labeled ubiquitin sample was prepared and introduced to an ESI-TOF mass spectrometer as described in Example 8. The resulting mass spectrum was deconvolved and sequenced as described in Example 10.

The true ubiquitin N-terminal sequence (MQIFVK (SEQ ID NO:12), obtained from GenBank) was correctly determined when "sequencer" was run to two, three, and four residues. The correct sequence ranked second out of 19 competing possibilities at the first residue. The correct sequence was also ranked second (to MQIFR (SEG ID NO:13)) at the fifth residue.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for discriminating between the mass of a labeled molecule or labeled molecule fragment and a mass of an unlabeled molecule or unlabeled molecule fragment in a sample, wherein the mass of the labeled molecule or labeled molecule fragment and the mass of the unlabeled molecule or unlabeled molecule fragment differ by less than one (1) amu, the method comprising the steps of:
   (a) accumulating a mass spectrum of said labeled molecule or labeled molecule fragment and said unlabeled molecule or unlabeled molecule fragment using a mass spectrometer, wherein the labeled molecule or labeled molecule fragment is labeled with a labeling moiety, said labeling moiety comprising at least one mass defect element having an atomic number from 17 to 77; and
   (b) discriminating between the mass of the labeled molecule or labeled molecule fragment and the mass of the unlabeled molecule or unlabeled molecule fragment in said mass spectrum based on the nuclear binding energy of the labeling moiety.

2. The method of claim 1, wherein said labeling moiety comprises at least one mass defect element of atomic number 35 to 63.

3. The method of claim 2, wherein said labeling moiety comprises at least one mass defect element of atomic number 39 to 58.

4. The method of claim 2, wherein said labeling moiety comprises at least one mass defect element selected from the group consisting of bromine, iodine, europium and yttrium.

5. The method of claim 4, wherein said mass defect element is europium.

6. The method of claim 4, wherein said mass defect element is yttrium.

7. The method of claim 4, wherein said mass defect element is bromine.

8. The method of claim 4, wherein said mass defect element is iodine.

9. The method of claim 1, wherein said labeled molecule is a labeled oligomer and said labeled molecule fragment is a labeled oligomer fragment.

10. The method of claim 9, wherein said labeled oligomer is selected from the group consisting of a labeled protein, labeled oligonucleotide, labeled oligosaccharide, labeled lipid, and labeled polymer of synthetic origin and said labeled oligomer fragment is selected from the group consisting of a labeled protein fragment, labeled oligonucleotide fragment, labeled oligosaccharide fragment, labeled lipid fragment, and labeled polymer of synthetic origin fragment.

11. The method of claim 10, wherein said labeled polymer of synthetic origin is a member selected from the group consisting of a labeled acrylate, labeled methacrylate, labeled nylon, labeled polyester, labeled polyimide, labeled nitrile rubber, and labeled polyolefin, labeled acrylate fragment, labeled methacrylate fragment, labeled nylon fragment, labeled polyester fragment, labeled polyimide fragment, labeled nitrile rubber fragment, and labeled polyolefin fragment.

12. The method of claim 9, wherein said labeled oligomer is a labeled oligonucleotide and said labeled oligomer fragment is a labeled oligonucleotide fragment.

13. The method of claim 9, wherein said labeled oligomer fragment produced using an enzymatic, chemolytic or mass spectrometric fragmentation method.

14. The method of claim 13, wherein said mass spectrometer fragmentation method is selected from the group consisting of in-source collision-induced dissociation, and collision cell collision-induced dissociation.

15. The method of claim 1, wherein several labeled molecules, each labeled with a different number of mass defect elements are mixed prior to said accumulation of the mass spectrum.

16. The method of claim 1, wherein several labeled molecules, each with a different number of stable isotopes, are mixed prior to said accumulation of the mass spectrum.

17. The method of claim 16, wherein the stable isotope is independently selected from the group consisting of isotopes of H, C, N, O, Cl, Br, and S.

18. The method of claim 16, wherein the stable isotope is independently selected from $^{79}$Br and $^{81}$Br.

19. The method of claim 1, wherein said sample comprises a complex mixture of molecules generated as a combinatorial library.

* * * * *